United States Patent [19]
Miyazaki et al.

[11] Patent Number: 6,130,187

[45] Date of Patent: *Oct. 10, 2000

[54] BENZOFURAN-7-YL URACIL DERIVATIVES AND HERBICIDES

[75] Inventors: Masahiro Miyazaki; Takeshi Deguchi; Takayoshi Takehi; Masatoshi Tamaru, all of Iwata-gun; Yoshihiro Yamaji, Ogasa-gun; Ryo Hanai, Ogasa-gun; Sota Uotsu, Ogasa-gun; Hideo Sadohara, Niiza, all of Japan

[73] Assignees: Kumiai Chemical Industry Co., Ltd.; Ihara Chemical Industry Co., Ltd., both of Tokyo, Japan

[*] Notice: This patent is subject to a terminal disclaimer.

[21] Appl. No.: 09/117,539

[22] PCT Filed: Feb. 7, 1997

[86] PCT No.: PCT/JP97/00320

§ 371 Date: Aug. 5, 1998

§ 102(e) Date: Aug. 5, 1998

[87] PCT Pub. No.: WO97/29105

PCT Pub. Date: Aug. 14, 1997

[30] Foreign Application Priority Data

Feb. 9, 1996 [JP] Japan ..................... 8-048327

[51] Int. Cl.⁷ ............... C07D 405/10; A01N 43/54
[52] U.S. Cl. ....................... 504/243; 544/310
[58] Field of Search .............. 504/243; 544/311, 544/312, 313, 314, 310

[56] References Cited

U.S. PATENT DOCUMENTS 5,521,147  5/1996  Theodoridis .............. 544/310

FOREIGN PATENT DOCUMENTS

| | | |
|---|---|---|
| 0 255 047 | 2/1988 | European Pat. Off. . |
| 0 271 170 | 6/1988 | European Pat. Off. . |
| 0 561 319 | 9/1993 | European Pat. Off. . |
| 0 617 033 | 9/1994 | European Pat. Off. . |
| 5-25165 | 2/1993 | Japan . |
| 06/ 321941 | 11/1994 | Japan . |
| 1035091 | 7/1966 | United Kingdom . |
| WO 93/15074 | 8/1993 | WIPO . |
| WO 95/05079 | 2/1995 | WIPO . |
| WO 95/05080 | 2/1995 | WIPO . |

*Primary Examiner*—John M. Ford
*Attorney, Agent, or Firm*—Oblon, Spivak, McClelland, Maier & Neustadt, P.C.

[57] ABSTRACT

A benzofuran-7-yl uracil derivative represented by the general formula (1):

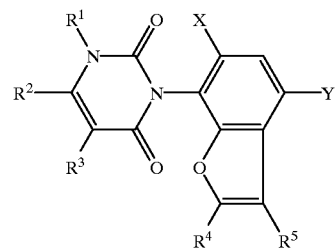

(1)

(wherein each of X and Y is a hydrogen atom, a halogen atom or the like, $R^1$ is a hydrogen atom, an alkyl group or the like, $R^2$ is a haloalkyl group or the like, $R^3$ is a hydrogen atom, a halogen atom or the like, each of $R^4$ and $R^5$ which are independent of each other, is a hydrogen atom, an alkyl group, a haloalkyl group, a halogen atom, a cyano group, a phenyl group, a benzyl group, a nitro group or the like), and a herbicide containing it as an active ingredient.

The compound of the present invention represented by the general formula (1) exhibits excellent herbicidal effects against various weeds which cause trouble in upland fields, such as, broad leaved weeds, gramineous weeds and perennial or annual cyperaceous weeds, over a wide range from the pre-emergence to the growing stage. It can further control annual weeds and perennial weeds growing in paddy fields.

11 Claims, No Drawings

BENZOFURAN-7-YL URACIL DERIVATIVES AND HERBICIDES

This is a 371 0f PCT/JP97/00320, filed Feb. 7,1997.

TECHNICAL FIELD

The present invention relates to novel benzofuran-7-yl uracil derivatives and herbicides containing them as active ingredients.

BACKGROUND ART

The specification of JP-A-5-262765 and the specification of JP-A-5-25165 disclose some benzofuran derivatives, the specification of JP-A-63-156787 discloses some benzopyran derivatives and benzofuran derivatives, and the specification of European Patent 626962 discloses benzothiophene derivatives and benzofuran derivatives, as they are useful as active ingredients for herbicides.

Herbicides to be used for useful crop plants, are desired to be agents which can be applied to soil or foliage and provide adequate herbicidal effects at low doses and which exhibit selectivity between crop plants and weeds. However, the herbicidal effects and the selectivity between crop plants and weeds, are influenced by the nature of soil, and phytotoxicity may sometimes be brought about to crop plants after the application, irrespective of soil treatment. From such a viewpoint, the compound disclosed in the above literatures can not necessarily be said to be satisfactory.

Under these circumstances, the present inventors have studied the herbicidal effects and the selectivity between crop plants and weeds and as a result, have found that novel benzofuran-7-yl uracil derivatives have excellent herbicidal effects and selectivity between crop plants and weeds, and have accomplished the present invention.

DISCLOSURE OF THE INVENTION

Namely, the present invention provides a benzofuran-7-yl uracil derivative represented by the general formula (1):

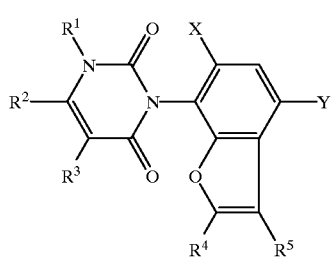

(1)

[wherein X is a hydrogen atom or a halogen atom, Y is a hydrogen atom, a halogen atom, a cyano group, an alkyl group, a haloalkyl group, an alkoxy group or a haloalkoxy group, $R^1$ is a hydrogen atom, an alkyl group, an amino group or a haloalkyl group, $R^2$ is an alkyl group or a haloalkyl group, $R^3$ is a hydrogen atom, a halogen atom, an alkyl group or a haloalkyl group, each of $R^4$ and $R^5$ which are the same or different, is a hydrogen atom, an alkyl group, a cycloalkyl group, an alkenyl group, an alkynyl group, a haloalkyl group, an alkoxy group, a haloalkoxy group, an alkenyloxy group, an alkynyloxy group, an alkoxycarbonylalkoxy group, an alkylthio group, a haloalkylthio group, an alkenylthio group, an alkynylthio group, an alkoxycarbonylalkylthio group, an alkylsulfonyl group, a haloalkylsulfonyl group, a phenylsulfonyl group which may be substituted, a halogen atom, a hydroxyiminoalkyl group, a hydroxyiminohaloalkyl group, an alkoxyiminoalkyl group, an alkoxyiminohaloalkyl group, an alkyliminoalkyl group, a phenyliminoalkyl group which may be substituted, a hydrazonoalkyl group, an alkylhydrazonoalkyl group, a phenylhydrazonoalkyl group which may be substituted, a cyano group, a carbamoyl group (having the same or different hydrogen atoms, alkyl groups, acyl groups, haloalkylcarbonyl groups, alkylsulfonyl groups, haloalkylsulfonyl groups or phenyl groups which may be substituted, substituted on the nitrogen atom), a phenyl group which may be substituted, a benzyl group which may be substituted, a cyanoalkyl group, a carbamoylalkyl group, a thiocyanoalkyl group, a nitro group, a hydroxyamino group, an oxiranyl group which may be substituted by an alkyl group, an amino group (having the same or different hydrogen atoms, alkyl groups, haloalkyl groups, alkenyl groups, alkynyl groups, cycloalkyl groups, alkylsulfonyl groups, haloalkylsulfonyl groups, phenylsulfonyl groups which may be substituted, acyl groups, haloalkylcarbonyl groups or benzoyl groups which may be substituted, substituted on the nitrogen atom), or a group represented by the general formula:

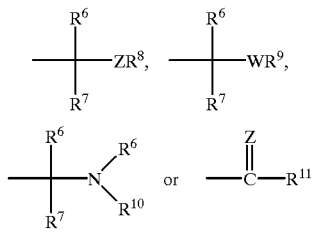

(wherein Z is an oxygen atom or a sulfur atom, W is a group of —SO— or a group of —$SO_2$—, $R^6$ is a hydrogen atom or an alkyl group, $R^7$ is a hydrogen atom, an alkyl group, a cycloalkyl group, an alkenyl group, an alkynyl group, a haloalkyl group, an alkoxyalkyl group or an alkylthioalkyl group, or $R^6$ and $R^7$ bond to each other to form a 3- to 8-membered (carbon) ring together with the carbon atom to which they are bonded, $R^8$ is a hydrogen atom, an alkyl group, a cycloalkyl group, a haloalkyl group, an alkoxycarbonylalkyl group, a hydroxycarbonylalkyl group, a monoalkylcarbamoylalkyl group, a dialkylcarbamoylalkyl group, an acyl group, an alkylsulfonyl group, a haloalkylsulfonyl group, a haloalkylcarbonyl group, a monoalkylcarbamoyl group, a monoalkylthiocarbamoyl group, a dialkylcarbamoyl group, a dialkylthiocarbamoyl group or a benzoyl group which may be substituted, $R^9$ is a hydrogen atom, an alkyl group, a cycloalkyl group, a haloalkyl group, an alkoxycarbonylalkyl group, a hydroxycarbonylalkyl group, a monoalkylcarbamoylalkyl group or a dialkylcarbamoylalkyl group, $R^{10}$ is a hydrogen atom, an alkyl group, an acyl group, an alkylsulfonyl group, a haloalkylsulfonyl group or a haloalkylcarbonyl group, $R^{11}$ is a hydrogen atom, an alkyl group, a cycloalkyl group, an alkenyl group, an alkynyl group, a haloalkyl group, an alkoxyalkyl group, an alkylthioalkyl group, a phenyl group which may be substituted, an alkoxy group, a haloalkoxy group, a benzyloxy group which may be substituted, a phenoxy group which may be substituted, or a hydroxyl group)], and a herbicide containing it as an active ingredient.

In this specification, alkyl in an alkyl group, an alkylthio group, an alkoxyalkyl group, an alkylthioalkyl group, an alkoxycarbonylalkylthio group, an alkyliminoalkyl group, a cyanoalkyl group, a carbamoylalkyl group, a thiocyanoalkyl group, an oxiranyl group which may be substituted by an alkyl group, an alkoxycarbonylalkyl group, a hydroxycarbonylalkyl group, a monoalkylcarbamoylalkyl group, a dialkylcarbamoylalkyl group, a hydroxyiminoalkyl group, an alkoxyiminoalkyl group, a phenyliminoalkyl group which may be substituted, a hydrazonoalkyl group, an alkylhydrazonoalkyl group, a phenylhydrazonoalkyl group which may be substituted and an alkylsulfonyl group, represents a $C_{1-6}$ straight chain or branched chain alkyl group, and, for example, a methyl group, an ethyl group, a n-propyl group, an isopropyl group, a n-butyl group, an isobutyl group, a sec-butyl group, a t-butyl group, a n-pentyl group, an isopentyl group, a neopentyl group, a n-hexyl group, an isohexyl group or a 3,3-dimethylbutyl group, may be mentioned.

Haloalkyl in a haloalkyl group, a haloalkylsulfonyl group, a haloalkylcarbonyl group, a hydroxyiminohaloalkyl group and an alkoxyiminohaloalkyl group, represents a $C_{1-4}$ straight chain or branched chain alkyl group substituted by halogen atom(s), and, for example, a chloromethyl group, a difluoromethyl group, a trifluoromethyl group or a pentafluoroethyl group, may be mentioned.

The halogen atom represents a fluorine atom, a chlorine atom, a bromine atom or an iodine atom.

Alkoxy in an alkoxy group, an alkoxyalkyl group, an alkoxycarbonylalkoxy group, an alkoxycarbonylalkylthio group, an alkoxyiminoalkyl group, an alkoxyiminohaloalkyl group and an alkoxycarbonylalkyl group, represents a $C_{1-6}$ straight chain or branched chain alkoxy group, and, for example, a methoxy group, an ethoxy group, a n-propoxy group, an isopropoxy group, a n-butoxy group, an isobutoxy group, a sec-butoxy group, a t-butoxy group, a n-pentyloxy group, an isopentyloxy group, a neopentyloxy group, a n-hexyloxy group, an isohexyloxy group or a 3,3-dimethylbutoxy group, may be mentioned.

The haloalkoxy group represents a $C_{1-4}$ straight chain or branched chain alkoxy group which is substituted by halogen atom(s), and, for example, a chloromethoxy group, a difluoromethoxy group, a trifluoromethoxy group or a pentafluoroethoxy group, may be mentioned.

The acyl group represents a $C_{1-6}$ straight chain or branched chain aliphatic acyl group, and, for example, a formyl group, an acetyl group, a propionyl group, a butyryl group or a pivaloyl group, may be mentioned.

Alkenyl in an alkenyl group, an alkenyloxy group and an alkenylthio group, represents a $C_{2-6}$ straight chain or branched chain alkenyl group, and, for example, a vinyl group, a propenyl group, an isopropenyl group, a butenyl group, a pentenyl group or a hexenyl group, may be mentioned.

Alkynyl in an alkynyl group, an alkynyloxy group and an alkynylthio group, represents a $C_{2-6}$ straight chain or branched chain alkynyl group, and, for example, an ethynyl group, a propynyl group, a butynyl group, a pentynyl group, a hexynyl group, a 3,3-dimethyl-1-butynyl group, a 4-methyl-1-pentynyl group or a 3-methyl-1-pentynyl group, may be mentioned.

The cycloalkyl group represents a $C_{3-8}$ cycloalkyl group, and, for example, a cyclopropyl group or a cyclohexyl group, may be mentioned.

The phenyl ring in a phenylsulfonyl group which may be substituted, a phenyliminoalkyl group which may be substituted, a phenylhydrazonoalkyl group which may be substituted, a phenoxy group which may be substituted, a benzyloxy group which may be substituted, a benzoyl group which may be substituted, a phenyl group which may be substituted, and a benzyl group which may be substituted, includes one substituted by a substituent such as a halogen atom, an alkyl group, an alkoxy group, a haloalkyl group, a haloalkoxy group, a nitro group or a cyano group.

Now, specific examples of the compounds of the present invention will be disclosed in Tables 1 to 24. However, the compounds of the present invention are not limited to such compounds. Further, the Compound Nos. will be referred to in the subsequent description.

TABLE 1

| Comp. Nos. | X | Y | $R^1$ | $R^2$ | $R^3$ | $R^4$ | $R^5$ | m.p. (° C.) RI* $n_D^{20}$ |
|---|---|---|---|---|---|---|---|---|
| 1 | F | Cl | $CH_3$ | $CF_3$ | H | H | H | 127–128 |
| 2 | F | Cl | $CH_3$ | $CF_3$ | H | $CH_3$ | H | 196–197 |
| 3 | F | Cl | $CH_3$ | $CF_3$ | H | $C_2H_5$ | H | 142–143 |
| 4 | F | Cl | $CH_3$ | $CF_3$ | H | $C_3H_7$ | H | 88–89 |
| 5 | F | Cl | $CH_3$ | $CF_3$ | H | $C_3H_7$-i | H | |
| 6 | F | Cl | $CH_3$ | $CF_3$ | H | $C_4H_9$ | H | 1.5375 |
| 7 | F | Cl | $CH_3$ | $CF_3$ | H | $C_4H_9$-i | H | 1.5358 |
| 8 | F | Cl | $CH_3$ | $CF_3$ | H | $CH_2Br$ | H | 168–172 |
| 9 | F | Cl | $CH_3$ | $CF_3$ | H | $CHBr_2$ | H | 126–128 |
| 10 | F | Cl | $CH_3$ | $CF_3$ | H | $CBr_3$ | H | Unmeasurable |
| 11 | F | Cl | $CH_3$ | $CF_3$ | H | $CHF_2$ | H | |
| 12 | F | Cl | $CH_3$ | $CF_3$ | H | $CH_2OH$ | H | 198–199 |
| 13 | F | Cl | $CH_3$ | $CF_3$ | H | $CH(CH_3)OH$ | H | 154–157 |
| 14 | F | Cl | $CH_3$ | $CF_3$ | H | $CH_2OCH_3$ | H | 1.5389 |

TABLE 1-continued

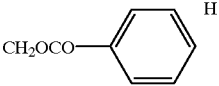

| Comp. Nos. | X | Y | $R^1$ | $R^2$ | $R^3$ | $R^4$ | $R^5$ | m.p. (° C.) RI* $n_D^{20}$ |
|---|---|---|---|---|---|---|---|---|
| 15 | F | Cl | $CH_3$ | $CF_3$ | H | $CH_2OC_2H_5$ | H | 1.5379 |
| 16 | F | Cl | $CH_3$ | $CF_3$ | H | $CH_2OCOCH_3$ | H | 1.5347 |
| 17 | F | Cl | $CH_3$ | $CF_3$ | H | $CH_2OCOC_2H_5$ | H | |
| 18 | F | Cl | $CH_3$ | $CF_3$ | H | $CH(CH_3)OCOCH_3$ | H | |
| 19 | F | Cl | $CH_3$ | $CF_3$ | H | $CH_2OCO$-phenyl | H | 160–162 |
| 20 | F | Cl | $CH_3$ | $CF_3$ | H | $CH_2SCH_3$ | H | Unmeasurable |
| 21 | F | Cl | $CH_3$ | $CF_3$ | H | $CH_2SO_2CH_3$ | H | 209–211 |
| 22 | F | Cl | $CH_3$ | $CF_3$ | H | $CH_2SC_2H_5$ | H | 1.5629 |
| 23 | F | Cl | $CH_3$ | $CF_3$ | H | $CH_2SO_2C_2H_5$ | H | 212–215 |
| 24 | F | Cl | $CH_3$ | $CF_3$ | H | $CH_2N(CH_3)_2$ | H | |
| 25 | F | Cl | $CH_3$ | $CF_3$ | H | $CH_2N(C_2H_5)_2$ | H | 1.5331 |
| 26 | F | Cl | $CH_3$ | $CF_3$ | H | Cl | H | 180–182 |
| 27 | F | Cl | $CH_3$ | $CF_3$ | H | Br | H | |

*RI: Refractive index

TABLE 2

| Comp. Nos. | X | Y | $R^1$ | $R^2$ | $R^3$ | $R^4$ | $R^5$ | m.p. (° C.) RI* $n_D^{20}$ |
|---|---|---|---|---|---|---|---|---|
| 28 | F | Cl | $CH_3$ | $CF_3$ | H | $COCH_3$ | H | 193–194 |
| 29 | F | Cl | $CH_3$ | $CF_3$ | H | $COC_2H_5$ | H | Unmeasurable |
| 30 | F | Cl | $CH_3$ | $CF_3$ | H | $COC_3H_7$ | H | Unmeasurable |
| 31 | F | Cl | $CH_3$ | $CF_3$ | H | $COC_3H_7$-i | H | 128–129 |
| 32 | F | Cl | $CH_3$ | $CF_3$ | H | CO-(2-chlorophenyl) | H | |
| 33 | F | Cl | $CH_3$ | $CF_3$ | H | CHO | H | 180–183 |
| 34 | F | Cl | $CH_3$ | $CF_3$ | H | CH=NOH | H | |
| 35 | F | Cl | $CH_3$ | $CF_3$ | H | $CH=NOCH_3$ | H | Unmeasurable |
| 36 | F | Cl | $CH_3$ | $CF_3$ | H | $C(CH_3)=NOH$ | H | 263–266 |
| 37 | F | Cl | $CH_3$ | $CF_3$ | H | $C(CH_3)=NOCH_3$ | H | 176–178 |
| 38 | F | Cl | $CH_3$ | $CF_3$ | H | $C(CH_3)=NOC_2H_5$ | H | |
| 39 | F | Cl | $CH_3$ | $CF_3$ | H | $C(CH_3)=NCH_3$ | H | |
| 40 | F | Cl | $CH_3$ | $CF_3$ | H | $C(CH_3)=NNHCH_3$ | H | |
| 41 | F | Cl | $CH_3$ | $CF_3$ | H | CN | H | |
| 42 | F | Cl | $CH_3$ | $CF_3$ | H | COOH | H | 267–268 (decomposed) |
| 43 | F | Cl | $CH_3$ | $CF_3$ | H | $COOCH_3$ | H | 194–196 |
| 44 | F | Cl | $CH_3$ | $CF_3$ | H | $COOC_2H_5$ | H | 1.5453 |
| 45 | F | Cl | $CH_3$ | $CF_3$ | H | $COOC_3H_7$-i | H | Unmeasurable |
| 46 | F | Cl | $CH_3$ | $CF_3$ | H | $COOC_5H_{11}$ | H | |

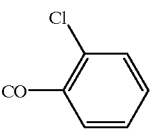

TABLE 2-continued

| Comp. Nos. | X | Y | R¹ | R² | R³ | R⁴ | R⁵ | m.p. (° C.) RI* $n_D^{20}$ |
|---|---|---|---|---|---|---|---|---|
| 47 | F | Cl | CH₃ | CF₃ | H | COO-C₆H₅ | H | |
| 48 | F | Cl | CH₃ | CF₃ | H | COOCH₂-C₆H₅ | H | |
| 49 | F | Cl | CH₃ | CF₃ | H | CONH₂ | H | |
| 50 | F | Cl | CH₃ | CF₃ | H | CONHCH₃ | H | |
| 51 | F | Cl | CH₃ | CF₃ | H | CON(CH₃)₂ | H | |
| 52 | F | Cl | CH₃ | CF₃ | H | CONHC₂H₅ | H | |
| 53 | F | Cl | CH₃ | CF₃ | H | CONH-C₆H₅ | H | |
| 54 | F | Cl | CH₃ | CF₃ | H | CONH-C₆H₄-CH₃ | H | |
| 55 | F | Cl | CH₃ | CF₃ | H | CONH-C₆H₄-Cl | H | |
| 56 | F | Cl | CH₃ | CF₃ | H | CONH-C₆H₄-OCH₃ | H | |
| 57 | F | Cl | CH₃ | CF₃ | H | CH₃-C₆H₄- | H | |
| 58 | F | Cl | CH₃ | CF₃ | H | CH₂-C₆H₅ | H | |
| 59 | F | Cl | CH₃ | CF₃ | H | NO₂ | H | |

TABLE 3

| Comp. Nos. | X | Y | R¹ | R² | R³ | R⁴ | R⁵ | m.p. (° C.) RI $n_D^{20}$ |
|---|---|---|---|---|---|---|---|---|
| 60 | F | Cl | CH₃ | CF₃ | H | NH₂ | H | |
| 61 | F | Cl | CH₃ | CF₃ | H | NHCOCH₃ | H | |
| 62 | F | Cl | CH₃ | CF₃ | H | NHCOCH₂Cl | H | |
| 63 | F | Cl | CH₃ | CF₃ | H | NHCOCF₃ | H | |
| 64 | F | Cl | CH₃ | CF₃ | H | NHCO-C₆H₅ | H | |

TABLE 3-continued

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 65 | F | Cl | $CH_3$ | $CF_3$ | H | $NHSO_2CH_3$ | H | |
| 66 | F | Cl | $CH_3$ | $CF_3$ | H | $NHSO_2CF_3$ | H | |
| 67 | F | Cl | $CH_3$ | $CF_3$ | H | $NHSO_2CH_2Cl$ | H | |
| 68 | F | Cl | $CH_3$ | $CF_3$ | H | $NHSO_2CHF_2$ | H | |
| 69 | F | Cl | $CH_3$ | $CF_3$ | H | $NHSO_2$-phenyl | H | |
| 70 | F | Cl | $CH_3$ | $CF_3$ | H | $CH_3$ | $CH_3$ | 181–183 |
| 71 | F | Cl | $CH_3$ | $CF_3$ | H | $CH_3$ | $C_2H_5$ | 130–131 |
| 72 | F | Cl | $CH_3$ | $CF_3$ | H | $CH_3$ | $C_3H_7$ | 1.5287 |
| 73 | F | Cl | $CH_3$ | $CF_3$ | H | $CH_3$ | $C_3H_7$-i | |
| 74 | F | Cl | $CH_3$ | $CF_3$ | H | $CH_3$ | $C_4H_9$ | 1.5398 |
| 75 | F | Cl | $CH_3$ | $CF_3$ | H | $CH_3$ | phenyl | 195–197 |
| 76 | F | Cl | $CH_3$ | $CF_3$ | H | $CH_3$ | $SCH_3$ | |
| 77 | F | Cl | $CH_3$ | $CF_3$ | H | $CH_3$ | Br | |
| 78 | F | Cl | $CH_3$ | $CF_3$ | H | $CH_3$ | Cl | 157–160 |
| 79 | F | Cl | $CH_3$ | $CF_3$ | H | $CH_3$ | $CH_2OH$ | 97–100 |
| 80 | F | Cl | $CH_3$ | $CF_3$ | H | $CH_3$ | $CH_2OCOCH_3$ | 168–170 |
| 81 | F | Cl | $CH_3$ | $CF_3$ | H | $CH_3$ | $CH_2OCH_3$ | |
| 82 | F | Cl | $CH_3$ | $CF_3$ | H | $CH_3$ | $CH_2OC_2H_5$ | |
| 83 | F | Cl | $CH_3$ | $CF_3$ | H | $CH_3$ | $CH_2SCH_3$ | 157–158 |
| 84 | F | Cl | $CH_3$ | $CF_3$ | H | $CH_3$ | $CH_2SO_2CH_3$ | 209–211 |
| 85 | F | Cl | $CH_3$ | $CF_3$ | H | $CH_3$ | $CH_2N(CH_3)_2$ | |
| 86 | F | Cl | $CH_3$ | $CF_3$ | H | $CH_3$ | COOH | 217–220 |
| 87 | F | Cl | $CH_3$ | $CF_3$ | H | $CH_3$ | $COOCH_3$ | 1.5440 |
| 88 | F | Cl | $CH_3$ | $CF_3$ | H | $CH_3$ | $COOC_2H_5$ | 1.5489 |
| 89 | F | Cl | $CH_3$ | $CF_3$ | H | $CH_3$ | $COOC_3H_7$-i | 154–156 |
| 90 | F | Cl | $CH_3$ | $CF_3$ | H | $CH_3$ | $COOC_5H_{11}$ | 1.5299 |
| 91 | F | Cl | $CH_3$ | $CF_3$ | H | $CH_3$ | CHO | 148–150 |
| 92 | F | Cl | $CH_3$ | $CF_3$ | H | $CH_3$ | CH=NOH | 82–84 |

TABLE 4

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 93 | F | Cl | $CH_3$ | $CF_3$ | H | $CH_3$ | $CH=NOCH_3$ | 1.5483 |
| 94 | F | Cl | $CH_3$ | $CF_3$ | H | $CH_3$ | CN | |
| 95 | F | Cl | $CH_3$ | $CF_3$ | H | $CH_3$ | $CONH_2$ | 102–105 |
| 96 | F | Cl | $CH_3$ | $CF_3$ | H | $CH_3$ | $CONHCH_3$ | |
| 97 | F | Cl | $CH_3$ | $CF_3$ | H | $CH_3$ | $CONHC_2H_5$ | |
| 98 | F | Cl | $CH_3$ | $CF_3$ | H | $CH_3$ | $CON(CH_3)_2$ | 90–93 |
| 99 | F | Cl | $CH_3$ | $CF_3$ | H | $CH_3$ | CONH-phenyl | |
| 100 | F | Cl | $CH_3$ | $CF_3$ | H | $CH_3$ | CONH-(4-Cl-phenyl) | |
| 101 | F | Cl | $CH_3$ | $CF_3$ | H | $CH_3$ | $COCH_3$ | 138–140 |
| 102 | F | Cl | $CH_3$ | $CF_3$ | H | $CH_3$ | $COC_2H_5$ | 1.5496 |
| 103 | F | Cl | $CH_3$ | $CF_3$ | H | $CH_3$ | $COCH_2Cl$ | 77–80 |
| 104 | F | Cl | $CH_3$ | $CF_3$ | H | $CH_3$ | $COCF_3$ | |

TABLE 4-continued

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 105 | F | Cl | $CH_3$ | $CF_3$ | H | $CH_3$ | $SO_2CH_3$ | |
| 106 | F | Cl | $CH_3$ | $CF_3$ | H | $CH_3$ | $SO_2CF_3$ | |
| 107 | F | Cl | $CH_3$ | $CF_3$ | H | $CH_3$ | $SO_2CH_2Cl$ | |
| 108 | F | Cl | $CH_3$ | $CF_3$ | H | $CH_3$ | $SO_2CHF_2$ | |
| 109 | F | Cl | $CH_3$ | $CF_3$ | H | $CH_3$ | $CH(CH_3)OH$ | |
| 110 | F | Cl | $CH_3$ | $CF_3$ | H | $CH_3$ | $C(CH_3)=NOH$ | 108–111 |
| 111 | F | Cl | $CH_3$ | $CF_3$ | H | $CH_3$ | $C(CH_3)=NOCH_3$ | 65–67 |
| 112 | F | Cl | $CH_3$ | $CF_3$ | H | $CH_3$ | $C(CH_3)=NOC_2H_5$ | |
| 113 | F | Cl | $CH_3$ | $CF_3$ | H | $CH_3$ | $C(CH_3)=NCH_3$ | |
| 114 | F | Cl | $CH_3$ | $CF_3$ | H | $CH_3$ | $C(CH_3)=NNHCH_3$ | 187–190 |
| 115 | F | Cl | $CH_3$ | $CF_3$ | H | $CH_3$ | 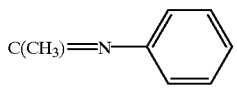 | |
| 116 | F | Cl | $CH_3$ | $CF_3$ | H | $CH_3$ | 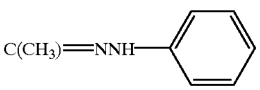 | 117–120 |
| 117 | F | Cl | $CH_3$ | $CF_3$ | H | $CH_3$ | 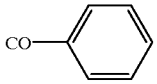 | 192–194 |
| 118 | F | Cl | $CH_3$ | $CF_3$ | H | $CH_3$ | 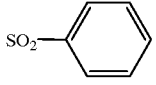 | |
| 119 | F | Cl | $CH_3$ | $CF_3$ | H | $CH_3$ | $NO_2$ | Unmeasurable |
| 120 | F | Cl | $CH_3$ | $CF_3$ | H | $CH_3$ | $NH_2$ | |
| 121 | F | Cl | $CH_3$ | $CF_3$ | H | $CH_3$ | $NHSO_2CH_3$ | |
| 122 | F | Cl | $CH_3$ | $CF_3$ | H | $CH_3$ | $NHSO_2CF_3$ | |
| 123 | F | Cl | $CH_3$ | $CF_3$ | H | $CH_3$ | $NHSO_2CH_2Cl$ | |
| 124 | F | Cl | $CH_3$ | $CF_3$ | H | $CH_3$ | $NHSO_2CHF_2$ | |
| 125 | F | Cl | $CH_3$ | $CF_3$ | H | $CH_3$ | $NHCOCH_3$ | 209–211 |

TABLE 5

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 126 | F | Cl | $CH_3$ | $CF_3$ | H | $CH_3$ | $NHCOCF_3$ | |
| 127 | F | Cl | $CH_3$ | $CF_3$ | H | $CH_3$ | $NHCOCH_2Cl$ | |
| 128 | F | Cl | $CH_3$ | $CF_3$ | H | $CH_3$ | 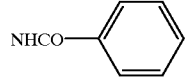 | |
| 129 | F | Cl | $CH_3$ | $CF_3$ | H | $CH_3$ | 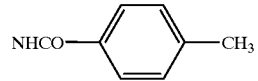 | |
| 130 | F | Cl | $CH_3$ | $CF_3$ | H | $CH_3$ | 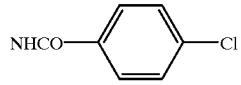 | |

TABLE 5-continued

| Comp. Nos. | X | Y | R¹ | R² | R³ | R⁴ | R⁵ | m.p. (° C.) RI $n_D^{20}$ |
|---|---|---|---|---|---|---|---|---|
| 131 | F | Cl | $CH_3$ | $CF_3$ | H | $CH_3$ | NHCO-C₆H₄-OCH₃ (4-methoxyphenyl) | |
| 132 | F | Cl | $CH_3$ | $CF_3$ | H | $CH_3$ | NHSO₂-C₆H₅ | |
| 133 | F | Cl | $CH_3$ | $CF_3$ | H | $CH_3$ | NHSO₂-C₆H₄-CH₃ (4-methylphenyl) | |
| 134 | F | Cl | $CH_3$ | $CF_3$ | H | $CH_3$ | NHSO₂-C₆H₄-Cl (4-chlorophenyl) | |
| 135 | F | Cl | $CH_3$ | $CF_3$ | H | $CH_3$ | NHSO₂-C₆H₄-OCH₃ (4-methoxyphenyl) | |
| 136 | F | Cl | $CH_3$ | $CF_3$ | H | $C_2H_5$ | $CH_3$ | |
| 137 | F | Cl | $CH_3$ | $CF_3$ | H | $C_2H_5$ | $CH_2OH$ | |
| 138 | F | Cl | $CH_3$ | $CF_3$ | H | $C_2H_5$ | $CH_2OCOCH_3$ | |
| 139 | F | Cl | $CH_3$ | $CF_3$ | H | $C_2H_5$ | $CH_2OCH_3$ | |
| 140 | F | Cl | $CH_3$ | $CF_3$ | H | $C_2H_5$ | COOH | 114–116 |
| 141 | F | Cl | $CH_3$ | $CF_3$ | H | $C_2H_5$ | CHO | Unmeasurable |
| 142 | F | Cl | $CH_3$ | $CF_3$ | H | $C_2H_5$ | $COOCH_3$ | 1.5341 |
| 143 | F | Cl | $CH_3$ | $CF_3$ | H | $C_2H_5$ | $COOC_3H_7$-i | 1.5229 |
| 144 | F | Cl | $CH_3$ | $CF_3$ | H | $C_2H_5$ | CH=NOCH₃ | |
| 145 | F | Cl | $CH_3$ | $CF_3$ | H | $C_2H_5$ | CH=NNHCH₃ | |
| 146 | F | Cl | $CH_3$ | $CF_3$ | H | $C_2H_5$ | Cl | |
| 147 | F | Cl | $CH_3$ | $CF_3$ | H | $C_2H_5$ | $COCH_3$ | 1.5503 |
| 148 | F | Cl | $CH_3$ | $CF_3$ | H | $C_2H_5$ | C(CH₃)=NOH | |
| 149 | F | Cl | $CH_3$ | $CF_3$ | H | $C_2H_5$ | C(CH₃)=NOCH₃ | |
| 150 | F | Cl | $CH_3$ | $CF_3$ | H | $C_2H_5$ | C(CH₃)=NNHCH₃ | |
| 151 | F | Cl | $CH_3$ | $CF_3$ | H | $C_2H_5$ | C(CH₃)=NNH-C₆H₅ | |
| 152 | F | Cl | $CH_3$ | $CF_3$ | H | $C_2H_5$ | $COC_2H_5$ | 139–140 |
| 153 | F | Cl | $CH_3$ | $CF_3$ | H | $C_2H_5$ | $COC_3H_7$-i | 115–117 |
| 154 | F | Cl | $CH_3$ | $CF_3$ | H | $C_2H_5$ | CO-C₆H₅ | |
| 155 | F | Cl | $CH_3$ | $CF_3$ | H | $C_2H_5$ | $NO_2$ | |
| 156 | F | Cl | $CH_3$ | $CF_3$ | H | $C_2H_5$ | $NH_2$ | |
| 157 | F | Cl | $CH_3$ | $CF_3$ | H | $C_2H_5$ | $NHCOCH_3$ | |
| 158 | F | Cl | $CH_3$ | $CF_3$ | H | $C_2H_5$ | $NHSO_2CH_3$ | |

TABLE 6

| Comp. Nos. | X | Y | R¹ | R² | R³ | R⁴ | R⁵ | m.p. (° C.) RI $n_D^{20}$ |
|---|---|---|---|---|---|---|---|---|
| 159 | | | CH₃ | CF₃ | H | C₂H₅ | NHSO₂CF₃ | |
| 160 | | | CH₃ | CF₃ | H | C₂H₅ | 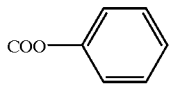 | |
| 161 | | | CH₃ | CF₃ | H | C₂H₅ | 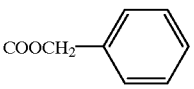 | |
| 162 | F | Cl | CH₃ | CF₃ | H | C₂H₅ | CONHCH₃ | |
| 163 | F | Cl | CH₃ | CF₃ | H | C₂H₅ | CON(CH₃)₂ | |
| 164 | F | Cl | CH₃ | CF₃ | H | C₃H₇ | CH₃ | |
| 165 | F | Cl | CH₃ | CF₃ | H | C₃H₇ | COCH₃ | 1.5362 |
| 166 | F | Cl | CH₃ | CF₃ | H | C₃H₇ | COOCH₃ | 103–104 |
| 167 | F | Cl | CH₃ | CF₃ | H | C₃H₇ | CH₂OCH₃ | |
| 168 | F | Cl | CH₃ | CF₃ | H | C₃H₇-i | CH₃ | |
| 169 | F | Cl | CH₃ | CF₃ | H | C₃H₇-i | COCH₃ | |
| 170 | F | Cl | CH₃ | CF₃ | H | C₃H₇-i | COOCH₃ | |
| 171 | F | Cl | CH₃ | CF₃ | H | C₃H₇-i | CH₂OCH₃ | |
| 172 | F | Cl | H | CF₃ | H | CH₃ | H | 172–174 |
| 173 | F | Cl | C₂H₅ | CF₃ | H | CH₃ | H | |
| 174 | F | Cl | C₃H₇ | CF₃ | H | CH₃ | H | |
| 175 | F | Cl | CH₂Cl | CF₃ | H | CH₃ | H | |
| 176 | F | Cl | CHF₂ | CF₃ | H | CH₃ | H | |
| 177 | F | Cl | H | CF₃ | CH₃ | CH₃ | H | |
| 178 | F | Cl | H | CF₃ | CH₂Cl | CH₃ | H | |
| 179 | F | Cl | H | CF₃ | Cl | CH₃ | H | |
| 180 | F | Cl | H | CF₃ | Br | CH₃ | H | |
| 181 | F | Cl | H | CH₃ | H | CH₃ | H | |
| 182 | F | Cl | CH₃ | CH₃ | H | CH₃ | H | |
| 183 | F | Cl | CHF₂ | CH₃ | H | CH₃ | H | |
| 184 | F | Cl | H | CH₃ | Cl | CH₃ | H | |
| 185 | F | Cl | H | CH₂Cl | H | CH₃ | H | |
| 186 | F | Cl | CH₃ | CH₂Cl | H | CH₃ | H | |
| 187 | F | Cl | H | CF₃ | H | C₂H₅ | H | 154–155 |
| 188 | F | Cl | H | CF₃ | CH₃ | C₂H₅ | H | |
| 189 | F | Cl | H | CF₃ | Cl | C₂H₅ | H | |
| 190 | F | Cl | CH₂Cl | CF₃ | H | C₂H₅ | H | |
| 191 | F | Cl | CHF₂ | CF₃ | H | C₂H₅ | H | |

TABLE 7

| Comp. Nos. | X | Y | R¹ | R² | R³ | R⁴ | R⁵ | m.p. (° C.) RI $n_D^{20}$ |
|---|---|---|---|---|---|---|---|---|
| 192 | F | Cl | CHF₂ | CF₃ | H | C₂H₅ | COOCH₃ | |
| 193 | F | Cl | CHF₂ | CF₃ | H | C₂H₅ | H | |
| 194 | F | Cl | CH₃ | CF₃ | Cl | C₂H₅ | H | |
| 195 | H | Cl | CH₃ | CF₃ | H | H | H | 142–144 |
| 196 | H | Cl | CH₃ | CF₃ | H | CH₃ | H | 206–207 |
| 197 | H | Cl | CH₃ | CF₃ | H | C₂H₅ | H | 159–160 |
| 198 | H | Cl | CH₃ | CF₃ | H | C₃H₇ | H | 159–161 |
| 199 | H | Cl | CH₃ | CF₃ | H | C₃H₇-i | H | |
| 200 | H | Cl | CH₃ | CF₃ | H | C₄H₉ | H | 101–102 |
| 201 | H | Cl | CH₃ | CF₃ | H | C₄H₉-i | H | 129–131 |
| 202 | H | Cl | CH₃ | CF₃ | H | CH₂Br | H | 200–202 |
| 203 | H | Cl | CH₃ | CF₃ | H | CHBr₂ | H | |
| 204 | H | Cl | CH₃ | CF₃ | H | CBr₃ | H | |
| 205 | H | Cl | CH₃ | CF₃ | H | CHF₂ | H | |
| 206 | H | Cl | CH₃ | CF₃ | H | CH₂OH | H | 179–181 |
| 207 | H | Cl | CH₃ | CF₃ | H | CH(CH₃)OH | H | 85–86 |
| 208 | H | Cl | CH₃ | CF₃ | H | CH₂OCH₃ | H | 141–143 |
| 209 | H | Cl | CH₃ | CF₃ | H | CH₂OC₂H₅ | H | 93–96 |

TABLE 7-continued

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 210 | H | Cl | $CH_3$ | $CF_3$ | H | $CH_2OCOCH_3$ | H | 135–138 |
| 211 | H | Cl | $CH_3$ | $CF_3$ | H | $CH_2OCOC_2H_5$ | H | |
| 212 | H | Cl | $CH_3$ | $CF_3$ | H | $CH(CH_3)OCOCH_3$ | H | |
| 213 | H | Cl | $CH_3$ | $CF_3$ | H | $CH_2OCO\text{-}C_6H_5$ | H | 180–182 |
| 214 | H | Cl | $CH_3$ | $CF_3$ | H | $CH_2SCH_3$ | H | |
| 215 | H | Cl | $CH_3$ | $CF_3$ | H | $CH_2SO_2CH_3$ | H | |
| 216 | H | Cl | $CH_3$ | $CF_3$ | H | $CH_2SC_2H_5$ | H | |
| 217 | H | Cl | $CH_3$ | $CF_3$ | H | $CH_2SO_2C_2H_5$ | H | |
| 218 | H | Cl | $CH_3$ | $CF_3$ | H | $CH_2NHCH_3$ | H | |
| 219 | H | Cl | $CH_3$ | $CF_3$ | H | $CH_2N(C_2H_5)_2$ | H | 1.5420 |
| 220 | H | Cl | $CH_3$ | $CF_3$ | H | Cl | H | |
| 221 | H | Cl | $CH_3$ | $CF_3$ | H | Br | H | |
| 222 | H | Cl | $CH_3$ | $CF_3$ | H | $COCH_3$ | H | 181–182 |
| 223 | H | Cl | $CH_3$ | $CF_3$ | H | $COC_2H_5$ | H | |
| 224 | H | Cl | $CH_3$ | $CF_3$ | H | $COC_3H_7$ | H | |

TABLE 8

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 225 | H | Cl | $CH_3$ | $CF_3$ | H | $COC_3H_7\text{-}i$ | H | |
| 226 | H | Cl | $CH_3$ | $CF_3$ | H | $CO\text{-}C_6H_5$ | H | |
| 227 | H | Cl | $CH_3$ | $CF_3$ | H | CHO | H | 233–235 |
| 228 | H | Cl | $CH_3$ | $CF_3$ | H | $CH(OCH_3)_2$ | H | 1.5416 |
| 229 | H | Cl | $CH_3$ | $CF_3$ | H | CH=NOH | H | |
| 230 | H | Cl | $CH_3$ | $CF_3$ | H | $CH=NOCH_3$ | H | 179–181 |
| 231 | H | Cl | $CH_3$ | $CF_3$ | H | $CH=NNHCH_3$ | H | Unmeasurable |
| 232 | H | Cl | $CH_3$ | $CF_3$ | H | $C(CH_3)=NOH$ | H | |
| 233 | H | Cl | $CH_3$ | $CF_3$ | H | $C(CH_3)=NOCH_3$ | H | 172–176 |
| 234 | H | Cl | $CH_3$ | $CF_3$ | H | $C(CH_3)=NOC_2H_5$ | H | |
| 235 | H | Cl | $CH_3$ | $CF_3$ | H | $C(CH_3)=NCH_3$ | H | |
| 236 | H | Cl | $CH_3$ | $CF_3$ | H | $C(CH_3)=NNHCH_3$ | H | |
| 237 | H | Cl | $CH_3$ | $CF_3$ | H | CN | H | |
| 238 | H | Cl | $CH_3$ | $CF_3$ | H | COOH | H | 270–273 |
| 239 | H | Cl | $CH_3$ | $CF_3$ | H | $COOCH_3$ | H | 137–138 |
| 240 | H | Cl | $CH_3$ | $CF_3$ | H | $COOC_2H_5$ | H | 116–117 |
| 241 | H | Cl | $CH_3$ | $CF_3$ | H | $COOC_3H_7\text{-}i$ | H | 144–145 |
| 242 | H | Cl | $CH_3$ | $CF_3$ | H | $COOC_5H_{11}$ | H | |
| 243 | H | Cl | $CH_3$ | $CF_3$ | H | $COO\text{-}C_6H_4\text{-}OCH_3$ | H | |
| 244 | H | Cl | $CH_3$ | $CF_3$ | H | $COOCH_2\text{-}C_6H_5$ | H | |
| 245 | H | Cl | $CH_3$ | $CF_3$ | H | $CONH_2$ | H | 273–275 |
| 246 | H | Cl | $CH_3$ | $CF_3$ | H | $CONHCH_3$ | H | 287–288 |
| 247 | H | Cl | $CH_3$ | $CF_3$ | H | $CON(CH_3)_2$ | H | Unmeasurable |
| 248 | H | Cl | $CH_3$ | $CF_3$ | H | $CONHC_2H_5$ | H | 225–226 |

TABLE 8-continued

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 249 | H | Cl | $CH_3$ | $CF_3$ | H | NHCO—C$_6$H$_5$ | H | 289–290 |
| 250 | H | Cl | $CH_3$ | $CF_3$ | H | CONH—C$_6$H$_4$—CH$_3$ | H | 294–296 |
| 251 | H | Cl | $CH_3$ | $CF_3$ | H | CONH—C$_6$H$_4$—Cl | H | >300 |
| 252 | H | Cl | $CH_3$ | $CF_3$ | H | CONH—C$_6$H$_4$—OCH$_3$ | H | 254–256 |
| 253 | H | Cl | $CH_3$ | $CF_3$ | H | CONH—(2-Cl-C$_6$H$_4$) | H | 177–180 |
| 254 | H | Cl | $CH_3$ | $CF_3$ | H | —C$_6$H$_4$—Cl | H | |
| 255 | H | Cl | $CH_3$ | $CF_3$ | H | —CH$_2$—C$_6$H$_4$—CH$_3$ | H | |
| 256 | H | Cl | $CH_3$ | $CF_3$ | H | $NO_2$ | H | |

TABLE 9

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 257 | H | Cl | $CH_3$ | $CF_3$ | H | $NH_2$ | H | |
| 258 | H | Cl | $CH_3$ | $CF_3$ | H | $NHCOCH_3$ | H | |
| 259 | H | Cl | $CH_3$ | $CF_3$ | H | $NHCOCH_2Cl$ | H | |
| 260 | H | Cl | $CH_3$ | $CF_3$ | H | $NHCOCF_3$ | H | |
| 261 | H | Cl | $CH_3$ | $CF_3$ | H | $NHSO_2CH_3$ | H | |
| 262 | H | Cl | $CH_3$ | $CF_3$ | H | $NHSO_2CF_3$ | H | |
| 263 | H | Cl | $CH_3$ | $CF_3$ | H | $NHSO_2CH_2Cl$ | H | |
| 264 | H | Cl | $CH_3$ | $CF_3$ | H | $NHSO_2CHF_2$ | H | |
| 265 | H | Cl | $CH_3$ | $CF_3$ | H | $CH_3$ | $CH_3$ | 152–153 |
| 266 | H | Cl | $CH_3$ | $CF_3$ | H | $CH_3$ | $C_2H_5$ | 141–142 |
| 267 | H | Cl | $CH_3$ | $CF_3$ | H | $CH_3$ | $C_3H_7$ | 1.5461 |
| 268 | H | Cl | $CH_3$ | $CF_3$ | H | $CH_3$ | $C_3H_7$-i | |
| 269 | H | Cl | $CH_3$ | $CF_3$ | H | $CH_3$ | $C_4H_9$ | 1.5557 |
| 270 | H | Cl | $CH_3$ | $CF_3$ | H | $CH_3$ | $C_6H_5$ | Unmeasurable |

TABLE 9-continued

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 271 | H | Cl | $CH_3$ | $CF_3$ | H | $CH_3$ | $SCH_3$ | |
| 272 | H | Cl | $CH_3$ | $CF_3$ | H | $CH_3$ | Br | 1.5632 |
| 273 | H | Cl | $CH_3$ | $CF_3$ | H | $CH_3$ | Cl | |
| 274 | H | Cl | $CH_3$ | $CF_3$ | H | $CH_3$ | $CH_2OH$ | |
| 275 | H | Cl | $CH_3$ | $CF_3$ | H | $CH_3$ | $CH_2OCOCH_3$ | |
| 276 | H | Cl | $CH_3$ | $CF_3$ | H | $CH_3$ | $CH_2OCH_3$ | |
| 277 | H | Cl | $CH_3$ | $CF_3$ | H | $CH_3$ | $CH_2OC_2H_5$ | |
| 278 | H | Cl | $CH_3$ | $CF_3$ | H | $CH_3$ | $CH_2SCH_3$ | |
| 279 | H | Cl | $CH_3$ | $CF_3$ | H | $CH_3$ | $CH_2SO_2CH_3$ | |
| 280 | H | Cl | $CH_3$ | $CF_3$ | H | $CH_3$ | $CH_2N(CH_3)_2$ | |
| 281 | H | Cl | $CH_3$ | $CF_3$ | H | $CH_3$ | COOH | |
| 282 | H | Cl | $CH_3$ | $CF_3$ | H | $CH_3$ | $COOCH_3$ | |
| 283 | H | Cl | $CH_3$ | $CF_3$ | H | $CH_3$ | $COOC_2H_5$ | |
| 284 | H | Cl | $CH_3$ | $CF_3$ | H | $CH_3$ | $COOC_3H_7$-i | |
| 285 | H | Cl | $CH_3$ | $CF_3$ | H | $CH_3$ | $COOC_5H_{11}$ | |
| 286 | H | Cl | $CH_3$ | $CF_3$ | H | $CH_3$ | CHO | |
| 287 | H | Cl | $CH_3$ | $CF_3$ | H | $CH_3$ | CH=NCH | |
| 288 | H | Cl | $CH_3$ | $CF_3$ | H | $CH_3$ | CH=NOCH$_3$ | |
| 289 | H | Cl | $CH_3$ | $CF_3$ | H | $CH_3$ | $COCH_3$ | 172–174 |

TABLE 10

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 290 | H | Cl | $CH_3$ | $CF_3$ | H | $CH_3$ | $COC_2H_5$ | |
| 291 | H | Cl | $CH_3$ | $CF_3$ | H | $CH_3$ | $COCH_2Cl$ | |
| 292 | H | Cl | $CH_3$ | $CF_3$ | H | $CH_3$ | $COCF_3$ | |
| 293 | H | Cl | $CH_3$ | $CF_3$ | H | $CH_3$ | $SO_2CH_3$ | |
| 294 | H | Cl | $CH_3$ | $CF_3$ | H | $CH_3$ | $SO_2CF_3$ | |
| 295 | H | Cl | $CH_3$ | $CF_3$ | H | $CH_3$ | $SO_2CH_2Cl$ | |
| 296 | H | Cl | $CH_3$ | $CF_3$ | H | $CH_3$ | $SO_2CHF_2$ | |
| 297 | H | Cl | $CH_3$ | $CF_3$ | H | $CH_3$ | $CH(CH_3)OH$ | |
| 298 | H | Cl | $CH_3$ | $CF_3$ | H | $CH_3$ | $C(CH_3)$=NOH | 248–250 |
| 299 | H | Cl | $CH_3$ | $CF_3$ | H | $CH_3$ | $C(CH_3)$=NOCH$_3$ | 167–168 |
| 300 | H | Cl | $CH_3$ | $CF_3$ | H | $CH_3$ | $C(CH_3)$=NOC$_2$H$_5$ | |
| 301 | H | Cl | $CH_3$ | $CF_3$ | H | $CH_3$ | 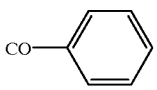 | 203–205 |
| 302 | H | Cl | $CH_3$ | $CF_3$ | H | $CH_3$ | 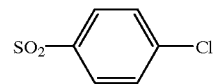 | |
| 303 | H | Cl | $CH_3$ | $CF_3$ | H | $CH_3$ | $NO_2$ | 174–175 |
| 304 | H | Cl | $CH_3$ | $CF_3$ | H | $CH_3$ | $NH_2$ | |
| 305 | H | Cl | $CH_3$ | $CF_3$ | H | $CH_3$ | NHOH | 134–136 |
| 306 | H | Cl | $CH_3$ | $CF_3$ | H | $CH_3$ | $NHSO_2CH_3$ | |
| 307 | H | Cl | $CH_3$ | $CF_3$ | H | $CH_3$ | $NHSO_2CF_3$ | |
| 308 | H | Cl | $CH_3$ | $CF_3$ | H | $CH_3$ | $NHSO_2CH_2Cl$ | |
| 309 | H | Cl | $CH_3$ | $CF_3$ | H | $CH_3$ | $NHSO_2CHF_2$ | |
| 310 | H | Cl | $CH_3$ | $CF_3$ | H | $CH_3$ | $NHCOCH_3$ | 290–292 |
| 311 | H | Cl | $CH_3$ | $CF_3$ | H | $CH_3$ | $NHCOCF_3$ | |
| 312 | H | Cl | $CH_3$ | $CF_3$ | H | $CH_3$ | $NHCOCH_2Cl$ | |
| 313 | H | Cl | $CH_3$ | $CF_3$ | H | $CH_3$ | 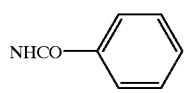 | |

TABLE 10-continued

| Comp. Nos. | X | Y | R¹ | R² | R³ | R⁴ | R⁵ | m.p. (° C.) RI $n_D^{20}$ |
|---|---|---|---|---|---|---|---|---|
| 314 | H | Cl | $CH_3$ | $CF_3$ | H | $CH_3$ | NHCO—C₆H₄—CH₃ (4-) | |
| 315 | H | Cl | $CH_3$ | $CF_3$ | H | $CH_3$ | NHCO—C₆H₄—Cl (4-) | |
| 316 | H | Cl | $CH_3$ | $CF_3$ | H | $CH_3$ | NHCO—C₆H₄—OCH₃ (4-) | |
| 317 | H | Cl | $CH_3$ | $CF_3$ | H | $CH_3$ | NHSO₂—C₆H₅ | |
| 318 | H | Cl | $CH_3$ | $CF_3$ | H | $CH_3$ | NHSO₂—C₆H₄—CH₃ (4-) | |
| 319 | H | Cl | $CH_3$ | $CF_3$ | H | $CH_3$ | NHSO₂—C₆H₄—Cl (4-) | |
| 320 | H | Cl | $CH_3$ | $CF_3$ | H | $CH_3$ | NHSO₂—C₆H₄—OCH₃ (4-) | |
| 321 | H | Cl | $CH_3$ | $CF_3$ | H | $C_2H_5$ | $CH_3$ | |
| 322 | H | Cl | $CH_3$ | $CF_3$ | H | $C_2H_5$ | $CH_2OH$ | |

TABLE 11

| Comp. Nos. | X | Y | R¹ | R² | R³ | R⁴ | R⁵ | m.p. (° C.) RI $n_D^{20}$ |
|---|---|---|---|---|---|---|---|---|
| 323 | H | Cl | $CH_3$ | $CF_3$ | H | $C_2H_5$ | $CH_2OCOCH_3$ | |
| 324 | H | Cl | $CH_3$ | $CF_3$ | H | $C_2H_5$ | $CH_2OCH_3$ | |
| 325 | H | Cl | $CH_3$ | $CF_3$ | H | $C_2H_5$ | CHO | 122–124 |
| 326 | H | Cl | $CH_3$ | $CF_3$ | H | $C_2H_5$ | COOH | |
| 327 | H | Cl | $CH_3$ | $CF_3$ | R | $C_2H_5$ | $COOCH_3$ | |
| 328 | H | Cl | $CH_3$ | $CF_3$ | H | $C_2H_5$ | $COOC_3H_7$-i | |
| 329 | H | Cl | $CH_3$ | $CF_3$ | H | $C_2H_5$ | Cl | |
| 330 | H | Cl | $CH_3$ | $CF_3$ | H | $C_2H_5$ | $COCH_3$ | 1.5662 |
| 331 | H | Cl | $CH_3$ | $CF_3$ | H | $C_2H_5$ | $C(CH_3)=NOH$ | 102–105 |
| 332 | H | Cl | $CH_3$ | $CF_3$ | H | $C_2H_5$ | $C(CH_3)=NOCH_3$ | 1.5442 |
| 333 | H | Cl | $CH_3$ | $CF_3$ | H | $C_2H_5$ | $COC_2H_5$ | |
| 334 | H | Cl | $CH_3$ | $CF_3$ | H | $C_2H_5$ | $COC_3H_7$-i | Unmeasurable |
| 335 | H | Cl | $CH_3$ | $CF_3$ | H | $C_2H_5$ | CO—C₆H₅ | |
| 336 | H | Cl | $CH_3$ | $CF_3$ | H | $C_2H_5$ | $CH_2SCH_3$ | |
| 337 | H | Cl | $CH_3$ | $CF_3$ | H | $C_2H_5$ | $CH_2SO_2CH_3$ | |

TABLE 11-continued

| Comp. Nos. | X | Y | R¹ | R² | R³ | R⁴ | R⁵ | m.p. (° C.) RI $n_D^{20}$ |
|---|---|---|---|---|---|---|---|---|
| 338 | H | Cl | CH₃ | CF₃ | H | C₂H₅ | CONHCH₃ | |
| 339 | H | Cl | CH₃ | CF₃ | H | C₂H₅ | CON(CH₃)₂ | |
| 340 | H | Cl | CH₃ | CF₃ | H | C₂H₅ | CONH–C₆H₅ | |
| 341 | H | Cl | CH₃ | CF₃ | H | C₃H₇ | CH₃ | |
| 342 | H | Cl | CH₃ | CF₃ | H | C₃H₇ | COCH₃ | |
| 343 | H | Cl | CH₃ | CF₃ | H | C₃H₇ | COOCH₃ | |
| 344 | H | Cl | CH₃ | CF₃ | H | C₃H₇ | CH₂OCH₃ | |
| 345 | H | Cl | CH₃ | CF₃ | H | C₃H₇-i | CH₃ | |
| 346 | H | Cl | CH₃ | CF₃ | H | C₃H₇-i | COCH₃ | |
| 347 | H | Cl | CH₃ | CF₃ | H | C₃H₇-i | COOCH₃ | |
| 348 | H | Cl | CH₃ | CF₃ | H | C₃H₇-i | CH₂OCH₃ | |
| 349 | H | Cl | CH₃ | CF₃ | H | C₄H₉ | COCH₃ | 1.5449 |
| 350 | H | Cl | CH₃ | CF₃ | H | CH₂Br | Br | 188–191 |
| 351 | H | Cl | H | CF₃ | H | CH₃ | H | |
| 352 | H | Cl | C₂H₅ | CF₃ | H | CH₃ | H | |
| 353 | H | Cl | C₃H₇ | CF₃ | H | CH₃ | H | |
| 354 | H | Cl | CH₂Cl | CF₃ | H | CH₃ | H | |
| 355 | H | Cl | CHF₂ | CF₃ | H | CH₃ | H | |

TABLE 12

| Comp. Nos. | X | Y | R¹ | R² | R³ | R⁴ | R⁵ | m.p. (° C.) RI $n_D^{20}$ |
|---|---|---|---|---|---|---|---|---|
| 356 | H | Cl | H | CF₃ | CH₃ | CH₃ | H | |
| 357 | H | Cl | H | CF₃ | CH₂Cl | CH₃ | H | |
| 358 | H | Cl | H | CF₃ | Cl | CH₃ | H | |
| 359 | H | Cl | H | CF₃ | Br | CH₃ | H | |
| 360 | H | Cl | H | CH₃ | H | CH₃ | H | |
| 361 | H | Cl | CH₃ | CH₃ | H | CH₃ | H | |
| 362 | H | Cl | CHF₂ | CH₃ | H | CH₃ | H | |
| 363 | H | Cl | H | CH₃ | Cl | CH₃ | H | |
| 364 | H | Cl | H | CH₂Cl | H | CH₃ | H | |
| 365 | H | Cl | CH₃ | CH₂Cl | H | CH₃ | H | |
| 366 | H | Cl | H | CF₃ | H | C₂H₅ | H | |
| 367 | H | Cl | H | CF₃ | CH₃ | C₂H₅ | H | |
| 368 | H | Cl | H | CF₃ | Cl | C₂H₅ | H | |
| 369 | H | Cl | CH₂Cl | CF₃ | H | C₂H₅ | H | |
| 370 | H | Cl | CHF₂ | CF₃ | H | C₂H₅ | H | |
| 371 | H | Cl | CHF₂ | CF₃ | H | C₂H₅ | COOCH₃ | |
| 372 | H | Cl | CHF₂ | CF₃ | H | C₂H₅ | H | |
| 373 | H | Cl | CH₃ | CF₃ | Cl | C₂H₅ | H | |
| 374 | F | F | CH₃ | CF₃ | H | H | H | 151–152 |
| 375 | F | F | CH₃ | CF₃ | H | CH₃ | H | 176–178 |
| 376 | F | F | CH₃ | CF₃ | H | CH₃ | COCH₃ | Unmeasurable |
| 377 | F | F | CH₃ | CF₃ | H | CH₃ | COOCH₃ | |
| 378 | F | F | CH₃ | CF₃ | H | CH₃ | CH₂OH | |
| 379 | F | F | CH₃ | CF₃ | H | C₂H₅ | H | 156–158 |
| 380 | F | F | CH₃ | CF₃ | H | C₂H₅ | COCH₃ | |
| 381 | F | F | CH₃ | CF₃ | H | C₂H₅ | COOCH₃ | |
| 382 | F | F | CH₃ | CF₃ | H | C₂H₅ | CH₂OH | |
| 383 | F | F | CH₃ | CF₃ | H | C₃H₇ | H | 137–140 |
| 384 | F | F | CH₃ | CF₃ | H | C₃H₇-i | H | |
| 385 | Cl | H | CH₃ | CF₃ | H | CH₃ | H | |
| 386 | F | H | CH₃ | CF₃ | H | CH₃ | H | |
| 387 | F | CN | CH₃ | CF₃ | H | CH₃ | H | |
| 388 | F | CH₃ | CH₃ | CF₃ | H | CH₃ | H | |

TABLE 13

| Comp. Nos. | X | Y | R¹ | R² | R³ | R⁴ | R⁵ | m.p. (° C.) RI $n_D^{20}$ |
|---|---|---|---|---|---|---|---|---|
| 389 | F | CF₃ | CH₃ | CF₃ | H | CH₃ | H | |
| 390 | F | OCH₃ | CH₃ | CF₃ | H | CH₃ | H | |
| 391 | F | OCHF₂ | CH₃ | CF₃ | H | CH₃ | H | |
| 392 | F | Cl | CH₃ | CF₃ | H | CH₂Cl | H | 181–182 |
| 393 | F | Cl | CH₃ | CF₃ | H | CH(CH₃)Cl | H | 1.5639 |
| 394 | F | Cl | CH₃ | CF₃ | H | CH(CH₃)Br | H | 1.5562 |
| 395 | F | Cl | CH₃ | CF₃ | H | CH(CH₃)OCH₃ | H | |
| 396 | F | Cl | CH₃ | CF₃ | H | CH(C₂H₅)Cl | H | |
| 397 | F | Cl | CH₃ | CF₃ | H | CO—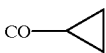 | H | 85–87 |
| 398 | F | Cl | CH₃ | CF₃ | H | COC₄H₉-n | H | 95–97 |
| 399 | F | Cl | CH₃ | CF₃ | H | COCH₂Cl | H | |
| 400 | F | Cl | CH₃ | CF₃ | H | COCH₂Br | H | 105–106 |
| 401 | F | Cl | CH₃ | CF₃ | H | CH(OH)C₂H₅ | H | Unmeasurable |
| 402 | F | Cl | CH₃ | CF₃ | H | CH(OH)C₃H₇ | H | 66–67 |
| 403 | F | Cl | CH₃ | CF₃ | H | CH(OH)C₃H₇-i | H | |
| 404 | F | Cl | CH₃ | CF₃ | H | CH(OH)C≡CH | H | 143–144 |
| 405 | F | Cl | CH₃ | CF₃ | H | CH(OH)CH=CH₂ | H | 87–88 |
| 406 | F | Cl | CH₃ | CF₃ | H | CH₂SC₃H₇ | H | 1.5656 |
| 407 | F | Cl | CH₃ | CF₃ | H | CH₂SO₂C₃H₇ | H | 156–157 |
| 408 | F | Cl | CH₃ | CF₃ | H | CH₂SC₃H₇-i | H | |
| 409 | F | Cl | CH₃ | CF₃ | H | CH₂SO₂C₃H₇-i | H | 125–127 |
| 410 | F | Cl | CH₃ | CF₃ | H | CH₂SC₄H₉ | H | 1.5512 |
| 411 | F | Cl | CH₃ | CF₃ | H | CH₂SO₂C₄H₉ | H | 103–104 |
| 412 | F | Cl | CH₃ | CF₃ | H | CH=CH₂ | H | 108–109 |
| 413 | F | Cl | CH₃ | CF₃ | H | C≡H | H | |
| 414 | F | Cl | CH₃ | CF₃ | H | CH₂SO₂CH₂CF₃ | H | |
| 415 | F | Cl | CH₃ | CF₃ | H |  | H | |
| 416 | F | Cl | CH₃ | CF₃ | H | CH₃ | OCH₂CF₃ | |
| 417 | F | Cl | CH₃ | CF₃ | H | CH₃ | CO— | 154–156 |
| 418 | F | Cl | CH₃ | CF₃ | H | CH₃ | CO—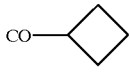 | 116–117 |
| 419 | F | Cl | CH₃ | CF₃ | H | CH₃ | COC₃H₇ | 124–126 |
| 420 | F | Cl | CH₃ | CF₃ | H | CH₃ | COC₃H₇-i | 1.5344 |
| 421 | F | Cl | CH₃ | CF₃ | H | CH₃ | COC₄H₉ | 104–105 |

TABLE 14

| Comp. Nos. | X | Y | R¹ | R² | R³ | R⁴ | R⁵ | m.p. (° C.) RI $n_D^{20}$ |
|---|---|---|---|---|---|---|---|---|
| 422 | F | Cl | CH₃ | CF₃ | H | CH₃ | COCH₂Br | 1.5650 |
| 423 | F | Cl | CH₃ | CF₃ | H | CH₃ | CH₂Cl | 177–179 |
| 424 | F | Cl | CH₃ | CF₃ | H | CH₃ | CH(CH₃)OH | 1.5345 |
| 425 | F | Cl | CH₃ | CF₃ | H | CH₃ | C(C₃H₇)=NOCH₃ | 1.5397 |
| 426 | F | Cl | CH₃ | CF₃ | H | CH₃ | C(CH₂Cl)=NOH | 107–109 |
| 427 | F | Cl | CH₃ | CF₃ | H | CH₃ | OCH₃ | 57–60 |
| 428 | F | Cl | CH₃ | CF₃ | H | CH₃ | OC₂H₅ | |
| 429 | F | Cl | CH₃ | CF₃ | H | CH₃ | OC₃H₇ | |
| 430 | F | Cl | CH₃ | CF₃ | H | CH₃ | OC₃H₇-i | |
| 431 | F | Cl | CH₃ | CF₃ | H | CH₃ | CH(CH₃)OCH₃ | |
| 432 | F | Cl | CH₃ | CF₃ | H | C₂H₅ | COOC₂H₅ | 133–135 |
| 433 | F | Cl | CH₃ | CF₃ | H | C₂H₅ | COOC₃H₇ | 124–125 |

TABLE 14-continued

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 434 | F | Cl | $CH_3$ | $CF_3$ | H | $C_2H_5$ | $COOC_4H_9$ | |
| 435 | F | Cl | $CH_3$ | $CF_3$ | H | $C_2H_5$ | $COC_3H_7$ | 1.5420 |
| 436 | F | Cl | $CH_3$ | $CF_3$ | H | $C_2H_5$ | CO—△ | 128–129 |
| 437 | F | Cl | $CH_3$ | $CF_3$ | H | $C_2H_5$ | $CH(CH_3)OH$ | |
| 438 | F | Cl | $CH_3$ | $CF_3$ | H | $C_2H_5$ | $CH(CH_3)OCH_3$ | |
| 439 | F | Cl | $CH_3$ | $CF_3$ | H | $C_3H_7$ | COOH | 147–148 |
| 440 | F | Cl | $CH_3$ | $CF_3$ | H | $C_3H_7$ | $CONH_2$ | 187–188 |
| 441 | F | Cl | $CH_3$ | $CF_3$ | H | $C_3H_7$ | $CONHCH_3$ | 198–200 |
| 442 | F | Cl | $CH_3$ | $CF_3$ | H | $C_3H_7$ | $CON(CH_3)_2$ | 1.5336 |
| 443 | F | Cl | $CH_3$ | $CF_3$ | H | $C_3H_7$ | $COOC_3H_7$-i | 1.5290 |
| 444 | F | Cl | $CH_3$ | $CF_3$ | H | $C_3H_7$ | $COC_2H_5$ | 1.5441 |
| 445 | F | Cl | $CH_3$ | $CF_3$ | H | $C_3H_7$ | $COC_3H_7$ | 1.5401 |
| 446 | F | Cl | $CH_3$ | $CF_3$ | H | $C_3H_7$ | $COC_3H_7$-i | Unmeasurable |
| 447 | F | Cl | $CH_3$ | $CF_3$ | H | $C_3H_7$ | $COCH_2Cl$ | 129–130 |
| 448 | F | Cl | $CH_3$ | $CF_3$ | H | $C_3H_7$ | $COCH_2Br$ | 110–111 |
| 449 | F | Cl | $CH_3$ | $CF_3$ | H | $C_3H_7$ | $CH_2OH$ | 1.5255 |
| 450 | F | Cl | $CH_3$ | $CF_3$ | H | $C_3H_7$ | CHO | 123–124 |
| 451 | F | Cl | $CH_3$ | $CF_3$ | H | $C_3H_7$ | $C(CH_3)=NOC_3H_7$-i | 1.5304 |
| 452 | F | Cl | $CH_3$ | $CF_3$ | H | $C_3H_7$ | $C(CH_3)=NOCH_3$ | 1.5332 |
| 453 | F | Cl | $CH_3$ | $CF_3$ | H | $COCH_3$ | $CH_3$ | 117–118 |
| 454 | F | Cl | $CH_3$ | $CF_3$ | H | $COC_2H_5$ | $CH_3$ | 119–120 |

TABLE 15

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 455 | F | Cl | $CH_3$ | $CF_3$ | H | $COC_3H_7$ | $CH_3$ | 1.5498 |
| 456 | F | Cl | $CH_3$ | $CF_3$ | H | $CH(OH)CH_3$ | $CH_3$ | 130–131 |
| 457 | F | Cl | $CH_3$ | $CF_3$ | H | $CH(OH)C_2H_5$ | $CH_3$ | 141–142 |
| 458 | F | Cl | $CH_3$ | $CF_3$ | H | $CH(OH)C_3H_7$ | $CH_3$ | 1.5392 |
| 459 | F | Cl | $CH_3$ | $CF_3$ | H | $COCH_3$ | $C_2H_5$ | 170–171 |
| 460 | F | Cl | $CH_3$ | $CF_3$ | H | $COC_2H_5$ | $C_2H_5$ | Unmeasurable |
| 461 | F | Cl | $CH_3$ | $CF_3$ | H | $COC_3H_7$ | $C_2H_5$ | 116–117 |
| 462 | F | Cl | $CH_3$ | $CF_3$ | H | $CH(OH)CH_3$ | $C_2H_5$ | 122–123 |
| 463 | F | Cl | $CH_3$ | $CF_3$ | H | $CH(OH)C_2H_5$ | $C_2H_5$ | Unmeasurable |
| 464 | F | Cl | $CH_3$ | $CF_3$ | H | $CH(OH)C_3H_7$ | $C_2H_5$ | Unmeasurable |
| 465 | F | F | $CH_3$ | $CF_3$ | H | $CH_3$ | $C(CH_3)=NOCH_3$ | 114–116 |
| 466 | H | Cl | $CH_3$ | $CF_3$ | H | $C_2H_5$ | $NHCOCH_3$ | 156–158 |
| 467 | F | Cl | $CH_3$ | $CF_3$ | H | $CH(CH_3)SCH_3$ | H | 1.5394 |
| 468 | F | Cl | $CH_3$ | $CF_3$ | H | $CH(CH_3)SOCH_3$ | H | 84–86 |
| 469 | F | Cl | $CH_3$ | $CF_3$ | H | $CH(CH_3)SO_2CH_3$ | H | 182–183 |
| 470 | F | Cl | $CH_3$ | $CF_3$ | H | $CH(CH_3)SC_2H_5$ | H | 1.5540 |
| 471 | F | Cl | $CH_3$ | $CF_3$ | H | $CH(CH_3)SOC_2H_5$ | H | 53–54 |
| 472 | F | Cl | $CH_3$ | $CF_3$ | H | $CH(CH_3)SO_2C_2H_5$ | H | 73–75 |
| 473 | F | Cl | $CH_3$ | $CF_3$ | H | $CH(CH_3)SC_3H_7$ | H | 1.5325 |
| 474 | F | Cl | $CH_3$ | $CF_3$ | H | $CH(CH_3)SOC_3H_7$ | H | 1.5585 |
| 475 | F | Cl | $CH_3$ | $CF_3$ | H | $CH(CH_3)SO_2C_3H_7$ | H | 67–68 |
| 476 | F | Cl | $CH_3$ | $CF_3$ | H | $CH(CH_3)SC_3H_7$-i | H | 1.5461 |
| 477 | F | Cl | $CH_3$ | $CF_3$ | H | $CH(CH_3)SOC_3H_7$-i | H | 1.5470 |
| 478 | F | Cl | $CH_3$ | $CF_3$ | H | $CH(CH_3)SO_2C_3H_7$-i | H | 159–161 |
| 479 | F | Cl | $CH_3$ | $CF_3$ | H | $CH(CH_3)SC_4H_9$ | H | 1.5435 |
| 480 | F | Cl | $CH_3$ | $CF_3$ | H | $CH(CH_3)SOC_4H_9$ | H | 1.5472 |
| 481 | F | Cl | $CH_3$ | $CF_3$ | H | $CH(CH_3)SO_2C_4H_9$ | H | 125–126 |
| 482 | F | Cl | $CH_3$ | $CF_3$ | H | $CH(C_2H_5)SCH_3$ | H | 1.5540 |
| 483 | F | Cl | $CH_3$ | $CF_3$ | H | $CH(C_2H_5)SOCH_3$ | H | 83–85 |
| 484 | F | Cl | $CH_3$ | $CF_3$ | H | $CH(C_2H_5)SO_2CH_3$ | H | 83–86 |
| 485 | F | Cl | $CH_3$ | $CF_3$ | H | $CH(C_2H_5)SC_2H_5$ | H | 1.5562 |
| 486 | F | Cl | $CH_3$ | $CF_3$ | H | $CH(C_2H_5)SOC_2H_5$ | H | 1.5231 |
| 487 | F | Cl | $CH_3$ | $CF_3$ | H | $CH(C_2H_5)SO_2C_2H_5$ | H | 178–179 |

TABLE 16

| Comp. Nos. | X | Y | R¹ | R² | R³ | R⁴ | R⁵ | m.p. (° C.) RI $n_D^{20}$ |
|---|---|---|---|---|---|---|---|---|
| 488 | F | Cl | CH₃ | CF₃ | H | CH(C₂H₅)SC₃H₇ | H | |
| 489 | F | Cl | CH₃ | CF₃ | H | CH(C₂H₅)SOC₃H₇ | H | |
| 490 | F | Cl | CH₃ | CF₃ | H | CH(C₂H₅)SO₂C₃H₇ | H | |
| 491 | F | Cl | CH₃ | CF₃ | H | CH(C₂H₅)SC₃H₇-i | H | |
| 492 | F | Cl | CH₃ | CF₃ | H | CH(C₂H₅)SOC₃H₇-i | H | |
| 493 | F | Cl | CH₃ | CF₃ | H | CH(C₂H₅)SO₂C₃H₇-i | H | |
| 494 | F | Cl | CH₃ | CF₃ | H | CH(C₃H₇)SCH₃ | H | |
| 495 | F | Cl | CH₃ | CF₃ | H | CH(C₃H₇)SOCH₃ | H | |
| 496 | F | Cl | CH₃ | CF₃ | H | CH(C₃H₇)SO₂CH₃ | H | |
| 497 | F | Cl | CH₃ | CF₃ | H | CH(C₃H₇)SC₂H₅ | H | |
| 498 | F | Cl | CH₃ | CF₃ | H | CH(C₃H₇)SOC₂H₅ | H | |
| 499 | F | Cl | CH₃ | CF₃ | H | CH(C₃H₇)SO₂C₂H₅ | H | |
| 500 | F | Cl | CH₃ | CF₃ | H | CH(C₃H₇-i)SCH₃ | H | |
| 501 | F | Cl | CH₃ | CF₃ | H | CH(C₃H₇-i)SOCH₃ | H | 1.5281 |
| 502 | F | Cl | CH₃ | CF₃ | H | CH(C₃H₇-i)SO₂CH₃ | H | 149–150 |
| 503 | F | Cl | CH₃ | CF₃ | H | CH(C₃H₇-i)SC₂H₅ | H | |
| 504 | F | Cl | CH₃ | CF₃ | H | CH(C₃H₇-i)SOC₂H₅ | H | 1.5404 |
| 505 | F | Cl | CH₃ | CF₃ | H | CH(C₃H₇-i)SO₂C₂H₅ | H | 1.5390 |
| 506 | F | Cl | CH₃ | CF₃ | H | C(CH₃)₂SCH₃ | H | |
| 507 | F | Cl | CH₃ | CF₃ | H | C(CH₃)₂SOCH₃ | H | |
| 508 | F | Cl | CH₃ | CF₃ | H | C(CH₃)₂SO₂CH₃ | H | 227–230 |
| 509 | F | Cl | CH₃ | CF₃ | H | C(CH₃)(C₂H₅)SOCH₃ | H | |
| 510 | F | Cl | CH₃ | CF₃ | H | C(CH₃)(C₂H₅)SO₂CH₃ | H | 85–87 |
| 511 | F | Cl | CH₃ | CF₃ | H | C(CH₃)(C₃H₇)SO₂CH₃ | H | 92–93 |
| 512 | F | Cl | CH₃ | CF₃ | H | C(CH₃)(CH₂OCH₃)SOCH₃ | H | |
| 513 | F | Cl | CH₃ | CF₃ | H | C(CH₃)(CH₂OCH₃)SO₂CH₃ | H | 1.5365 |
| 514 | F | Cl | CH₃ | CF₃ | H | C(CH₃)(CH₂SCH₃)SO₂CH₃ | H | |
| 515 | F | Cl | CH₃ | CF₃ | H | CH(CH₃)SCF₃ | H | Unmeasurable |
| 516 | F | Cl | CH₃ | CF₃ | H | CH(CH₃)SOCF₃ | H | |
| 517 | F | Cl | CH₃ | CF₃ | H | CH(CH₃)SO₂CF₃ | H | |
| 518 | F | Cl | CH₃ | CF₃ | H | CH(CH₃)SCHF₂ | H | |
| 519 | F | Cl | CH₃ | CF₃ | H | CH(CH₃)SOCHF₂ | H | |
| 520 | F | Cl | CH₃ | CF₃ | H | CH(CH₃)SO₂CHF₂ | H | |

TABLE 17

| Comp. Nos. | X | Y | R¹ | R² | R³ | R⁴ | R⁵ | m.p. (° C.) RI $n_D^{20}$ |
|---|---|---|---|---|---|---|---|---|
| 521 | F | Cl | CH₃ | CF₃ | H | CH₂SCH₂COOCH₃ | H | 1.5390 |
| 522 | F | Cl | CH₃ | CF₃ | H | CH₂SOCH₂COOCH₃ | H | |
| 523 | F | Cl | CH₃ | CF₃ | H | CH₂SO₂CH₂COOCH₃ | H | |
| 524 | F | Cl | CH₃ | CF₃ | H | CH(CH₃)SCH₂COOCH₃ | H | 1.5411 |
| 525 | F | Cl | CH₃ | CF₃ | H | CH(CH₃)SC₃H₆Cl | H | |
| 526 | F | Cl | CH₃ | CF₃ | H | CH(CH₃)SOC₃H₆Cl | H | |
| 527 | F | Cl | CH₃ | CF₃ | H | CH(CH₃)SC₂H₄COOCH₃ | H | |
| 528 | F | Cl | CH₃ | CF₃ | H | CH(CH₃)SO₂C₂H₄COOCH₃ | H | |
| 529 | F | Cl | CH₃ | CF₃ | H | CH(CH₃)SCH₂CONHCH₃ | H | |
| 530 | F | Cl | CH₃ | CF₃ | H | CH(CH₃)SO₂CH₂CONHCH₃ | H | |
| 531 | F | Cl | CH₃ | CF₃ | H | CH(CH₃)SCH₂CON(CH₃)₂ | H | |
| 532 | F | Cl | CH₃ | CF₃ | H | CH(CH₃)SO₂CH₂CON(CH₃)₂ | H | |
| 533 | F | Cl | CH₃ | CF₃ | H | CH(CH₃)SCH₂COOH | H | |
| 534 | F | Cl | CH₃ | CF₃ | H | CH(CH₃)SOCH₂COOH | H | |
| 535 | F | Cl | CH₃ | CF₃ | H | CH(CH₃)SO₂CH₂COOH | H | |
| 536 | F | Cl | CH₃ | CF₃ | H | CH(CH₃)S—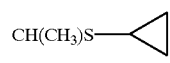 | H | |
| 537 | F | Cl | CH₃ | CF₃ | H | CH(CH₃)SO—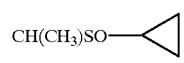 | H | |
| 538 | F | Cl | CH₃ | CF₃ | H | CH(CH₃)SO₂—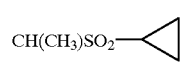 | H | |

TABLE 17-continued

| Comp. Nos. | X | Y | R¹ | R² | R³ | R⁴ | R⁵ | m.p. (° C.) RI $n_D^{20}$ |
|---|---|---|---|---|---|---|---|---|
| 539 | F | Cl | CH₃ | CF₃ | H | CH₂SOCH₃ | H | 127–129 |
| 540 | F | Cl | CH₃ | CF₃ | H | CH(CH₃)SH | H | |
| 541 | F | Cl | CH₃ | CF₃ | H | CH(CH₃)SCOCH₃ | H | |
| 542 | F | Cl | CH₃ | CF₃ | H | CH(CH₃)SCON(CH₃)₂ | H | |
| 543 | F | Cl | CH₃ | CF₃ | H | CH(CH₃)SCONHCH₃ | H | |
| 544 | F | Cl | CH₃ | CF₃ | H | CH(CH₃)SCSN(CH₃)₂ | H | |
| 545 | F | Cl | CH₃ | CF₃ | H | CH(CH₃)SCSNHCH₃ | H | |
| 546 | F | F | CH₃ | CF₃ | H | CH(CH₃)Br | H | 1.5389 |
| 547 | F | F | CH₃ | CF₃ | H | CH(CH₃)SCF₃ | H | 1.5140 |
| 548 | F | F | CH₃ | CF₃ | H | CH(CH₃)SCN | H | 1.5450 |
| 549 | F | Cl | CH₃ | CF₃ | H | C(CH₃)₂OH | H | 160–161 |
| 550 | F | F | CH₃ | CF₃ | H | CH(CH₃)SO₂CF₃ | H | |
| 551 | F | Cl | CH₃ | CF₃ | H | CH(CH₃)NHSO₂CF₃ | H | Unmeasurable |
| 552 | F | Cl | CH₃ | CF₃ | H | CH(CH₂Cl)SCH₃ | H | |
| 553 | F | Cl | CH₃ | CF₃ | H | CH(CH₂Cl)SOCH₃ | H | |

TABLE 18

| Comp. Nos. | X | Y | R¹ | R² | R³ | R⁴ | R⁵ | m.p. (° C.) RI $n_D^{20}$ |
|---|---|---|---|---|---|---|---|---|
| 554 | F | Cl | CH₃ | CF₃ | H | CH(CH₂Cl)SO₂CH₃ | H | |
| 555 | F | Cl | CH₃ | CF₃ | H | CH(CH=CH₂)SCH₃ | H | |
| 556 | F | Cl | CH₃ | CF₃ | H | CH(CH=CH₂)SOCH₃ | H | |
| 557 | F | Cl | CH₃ | CF₃ | H | CH(CH=CH₂)SO₂CH₃ | H | |
| 558 | F | Cl | CH₃ | CF₃ | H | CH(C≡CH)SCH₃ | H | |
| 559 | F | Cl | CH₃ | CF₃ | H | CH(C≡CH)SOCH₃ | H | |
| 560 | F | Cl | CH₃ | CF₃ | H | CH(C≡CH)SO₂CH₃ | H | |
| 561 | F | Cl | CH₃ | CF₃ | H | CH(-cyclopropyl)SCH₃ | H | |
| 562 | F | Cl | CH₃ | CF₃ | H | CH(-cyclopropyl)SOCH₃ | H | |
| 563 | F | Cl | CH₃ | CF₃ | H | CH(-cyclopropyl)SO₂CH₃ | H | |
| 564 | F | Cl | CH₃ | CF₃ | H | 1-(SO₂CH₃)cyclopropyl | H | |
| 565 | F | Cl | CH₃ | CF₃ | H | CH(CH₂OCH₃)SCH₃ | H | |
| 566 | F | Cl | CH₃ | CF₃ | H | CH(CH₂OCH₃)SO₂CH₃ | H | |
| 567 | F | Cl | CH₃ | CF₃ | H | CH(CH₂SCH₃)SCH₃ | H | |
| 568 | F | Cl | CH₃ | CF₃ | H | CH(CF₃)SCH₃ | H | |
| 569 | F | Cl | CH₃ | CF₃ | H | CH(CF₃)SOCH₃ | H | |
| 570 | F | Cl | CH₃ | CF₃ | H | CH(CF₃)SO₂CH₃ | H | |
| 571 | F | Cl | CH₃ | CF₃ | H | CH(CH₃)NHCH₃ | H | Unmeasurable |
| 572 | F | Cl | CH₃ | CF₃ | H | CH(CH₃)N(CH₃)₂ | H | 1.5341 |
| 573 | F | Cl | CH₃ | CF₃ | H | CH(CH₃)NHSO₂CF₃ | H | |
| 574 | F | Cl | CH₃ | CF₃ | H | CH(CH₃)NHSO₂CH₃ | H | |
| 575 | F | Cl | CH₃ | CF₃ | H | CH(CH₃)NHCOCH₃ | H | |
| 576 | F | Cl | CH₃ | CF₃ | H | CH(CH₃)NHCOCH₂Cl | H | |
| 577 | F | Cl | CH₃ | CF₃ | H | CH(CH₃)SCN | H | 60–63 |
| 578 | F | Cl | CH₃ | CF₃ | H | CH(-cyclopropyl)OH | H | 113–115 |
| 579 | F | Cl | CH₃ | CF₃ | H | CH(CH₂Cl)OH | H | |
| 580 | F | Cl | CH₃ | CF₃ | H | CH(CH₂Br)OH | H | |

TABLE 18-continued

| Comp. Nos. | X | Y | R¹ | R² | R³ | R⁴ | R⁵ | m.p. (° C.) RI $n_D^{20}$ |
|---|---|---|---|---|---|---|---|---|
| 581 | F | Cl | CH₃ | CF₃ | H | CH(CF₃)OH | H | |
| 582 | F | Cl | CH₃ | CF₃ | H | CH(CH₂OCH₃)OH | H | |
| 583 | F | Cl | CH₃ | CF₃ | H | CH(CH₂SCH₃)OH | H | |
| 584 | F | Cl | CH₃ | CF₃ | H | CH(CH₃)OCH₃ | H | 120–121 |
| 585 | F | Cl | CH₃ | CF₃ | H | CH(CH₃)OC₂H₅ | H | 1.5080 |

TABLE 19

| Comp. Nos. | X | Y | R¹ | R² | R³ | R⁴ | R⁵ | m.p. (° C.) RI $n_D^{20}$ |
|---|---|---|---|---|---|---|---|---|
| 586 | F | Cl | CH₃ | CF₃ | H | CH(CH₃)OC₃H₇ | H | 1.5241 |
| 587 | F | Cl | CH₃ | CF₃ | H | CH(CH₃)OCHF₂ | H | |
| 588 | F | Cl | CH₃ | CF₃ | H | CH(CH₃)OCH₂-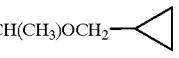 | H | |
| 589 | F | Cl | CH₃ | CF₃ | H | CH(CH₃)OCH₂COOCH₃ | H | |
| 590 | F | Cl | CH₃ | CF₃ | H | CH(CH₃)OCH₂CON(CH₃)₂ | H | |
| 591 | F | Cl | CH₃ | CF₃ | H | CH(CH₃)OCOCH₃ | H | 1.5251 |
| 592 | F | Cl | CH₃ | CF₃ | H | CH(CH₃)OCON(CH₃)₂ | H | 1.5937 |
| 593 | F | Cl | CH₃ | CF₃ | H | CH(CH₃)OCSN(CH₃)₂ | H | |
| 594 | F | Cl | CH₃ | CF₃ | H | CH(CH₃)OCONHCH₃ | H | |
| 595 | F | Cl | CH₃ | CF₃ | H | CH(CH₃)OCSNHCH₃ | H | |
| 596 | F | Cl | CH₃ | CF₃ | H | CH(CH₃)NH₂ | H | |
| 597 | F | Cl | CH₃ | CF₃ | H | CH(CH₃)CN | H | |
| 598 | F | Cl | CH₃ | CF₃ | H | CH(CH₃)CONH₂ | H | |
| 599 | F | Cl | CH₃ | CF₃ | H | CH(CH₃)OCH₂OCH₃ | H | |
| 600 | F | Cl | CH₃ | CF₃ | H | CH(CH₃)OCH₂SCH₃ | H | |
| 601 | F | Cl | CH₃ | CF₃ | H | COCH=CH₂ | H | |
| 602 | F | Cl | CH₃ | CF₃ | H | COC≡CH | H | |
| 603 | F | Cl | CH₃ | CF₃ | H | COCH₂OCH₃ | H | |
| 604 | F | Cl | CH₃ | CF₃ | H | COCH₂SCH₃ | H | |
| 605 | F | Cl | CH₃ | CF₃ | H | C₅H₁₁ | H | 1.5397 |
| 606 | F | Cl | CH₃ | CF₃ | H |  | H | 109–111 |
| 607 | F | Cl | CH₃ | CF₃ | H | 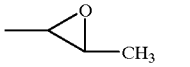 | H | 1.5389 |
| 608 | F | Cl | CH₃ | CF₃ | H | 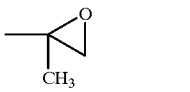 | H | |
| 609 | F | Cl | CH₃ | CF₃ | H | 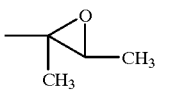 | H | |
| 610 | F | Cl | CH₃ | CF₃ | H | CH=CHCH₃ | H | 149–151 |
| 611 | F | Cl | CH₃ | CF₃ | H | C(CH₃)=CH₂ | H | 155–156 |
| 612 | F | Cl | CH₃ | CF₃ | H | C(CH₃)=CHCH₃ | H | 153–155 |
| 613 | F | Cl | CH₃ | CF₃ | H | C(C₂H₅)=CH₂ | H | |
| 614 | F | Cl | CH₃ | CF₃ | H | C(C₂H₅)=CHCH₃ | H | |

TABLE 20

| Comp. Nos. | X | Y | R¹ | R² | R³ | R⁴ | R⁵ | m.p. (° C.) RI $n_D^{20}$ |
|---|---|---|---|---|---|---|---|---|
| 615 | F | Cl | CH₃ | CF₃ | H | C(CH₃)=C(CH₃)₂ | H | |
| 616 | F | Cl | CH₃ | CF₃ | H | CH=C(CH₃)₂ | H | |
| 617 | F | Cl | CH₃ | CF₃ | H | CH₃ | CH₂Br | 181–183 |
| 618 | F | Cl | CH₃ | CF₃ | H | CH₃ | CH₂CN | 224–226 |
| 619 | F | Cl | CH₃ | CF₃ | H | CH₃ | CH₂CONH₂ | 127–129 |
| 620 | F | Cl | CH₃ | CF₃ | H | CH₃ | OCHF₂ | |
| 621 | F | Cl | CH₃ | CF₃ | H | CH₃ | OCH₂CH=CH₂ | |
| 622 | F | Cl | CH₃ | CF₃ | H | CH₃ | OCH₂C≡CH | 1.5331 |
| 623 | F | Cl | CH₃ | CF₃ | H | CH₃ | OCH₂COOCH₃ | 53–55 |
| 624 | F | Cl | CH₃ | CF₃ | H | CH₃ | OCH(CH₃)COOCH₃ | 71–73 |
| 625 | F | Cl | CH₃ | CF₃ | H | CH₃ | SCHF₂ | |
| 626 | F | Cl | CH₃ | CF₃ | H | CH₃ | SCH₂CH=CH₂ | |
| 627 | F | Cl | CH₃ | CF₃ | H | CH₃ | SCH₂C≡CH | |
| 628 | F | Cl | CH₃ | CF₃ | H | CH₃ | SCH₂COOC₂H₅ | |
| 629 | F | Cl | CH₃ | CF₃ | H | CH₃ | SCH(CH₃)COOCH₃ | |
| 630 | F | Cl | CH₃ | CF₃ | H | CH₃ | CO-cyclohexyl | 1.5275 |
| 631 | F | Cl | CH₃ | CF₃ | H | CH₃ | CSCH₃ | 1.5967 |
| 632 | F | Cl | CH₃ | CF₃ | H | CH₃ | COOCH₂-phenyl | 1.5331 |
| 633 | F | Cl | CH₃ | CF₃ | H | CH₃ | COOCH₂-C₆H₄-OCH₃ | |
| 634 | F | Cl | CH₃ | CF₃ | H | CH₃ | COOCH₂CH₂F | 109–110 |
| 635 | F | Cl | CH₃ | CF₃ | H | CH₃ | CH=CH₂ | 58–60 |
| 636 | F | Cl | CH₃ | CF₃ | H | CH₃ | CH=CHCH₃ | 1.5409 |
| 637 | F | Cl | CH₃ | CF₃ | H | CH₃ | methyloxirane | |
| 638 | F | Cl | CH₃ | CF₃ | H | CH₃ | 2,3-dimethyloxirane | 169–170 |
| 639 | F | Cl | CH₃ | CF₃ | H | C₂H₅ | COCH₂Br | 158–159 |
| 640 | F | Cl | CH₃ | CF₃ | H | C₃H₇ | COOC₂H₅ | 1.5140 |
| 641 | F | Cl | CH₃ | CF₃ | H | C₃H₇ | COOC₅H₁₁ | 1.5209 |
| 642 | F | Cl | CH₃ | CF₃ | H | C₃H₇ | COOCH₂-phenyl | 1.5485 |
| 643 | F | Cl | CH₃ | CF₃ | H | C₄H₉ | CHO | 128–130 |
| 644 | F | Cl | CH₃ | CF₃ | H | C₄H₉ | COOCH₃ | 1.5410 |
| 645 | F | Cl | CH₃ | CF₃ | H | C₄H₉ | COOH | 1.5342 |

TABLE 21

| Comp. Nos. | X | Y | $R^1$ | $R^2$ | $R^3$ | $R^4$ | $R^5$ | m.p. (°C.) RI $n_D^{20}$ |
|---|---|---|---|---|---|---|---|---|
| 646 | F | Cl | $CH_3$ | $CF_3$ | H | $C_4H_9$—i | CHO | 54–55 |
| 647 | F | Cl | $CH_3$ | $CF_3$ | H | $C_4H_9$—i | $COOCH_3$ | 62–63 |
| 648 | F | Cl | $CH_3$ | $CF_3$ | H | $C_4H_9$—i | COOH | 208–209 |
| 649 | F | Cl | $CH_3$ | $CF_3$ | H | $C_5H_{11}$ | CHO | Unmeasurable |
| 650 | F | Cl | $CH_3$ | $CF_3$ | H | $C_5H_{11}$ | $COOCH_3$ | 1.5271 |
| 651 | F | Cl | $CH_3$ | $CF_3$ | H | $C_5H_{11}$ | COOH | 1.5156 |
| 652 | F | Cl | $CH_3$ | $CF_3$ | H | $CH_2Br$ | $CH_2Br$ | 225–227 |
| 653 | F | Cl | $CH_3$ | $CF_3$ | H | $CH_2Br$ | $CHBr_2$ | 146–147 |
| 654 | F | Cl | $CH_3$ | $CF_3$ | H | $NO_2$ | $CH_3$ | 146–148 |
| 655 | F | Cl | $CH_3$ | $CF_3$ | H | H | $COOCH_3$ | 95–97 |
| 656 | F | Cl | $CH_3$ | $CF_3$ | H | $COCH_3$ | $COOCH_3$ | 91–93 |
| 657 | F | Cl | $CH_3$ | $CF_3$ | H | $CH(CH_3)OH$ | $COOCH_3$ | 95–97 |
| 658 | F | Cl | $CH_3$ | $CF_3$ | H | $CH(CH=CH_2)OH$ | $COOCH_3$ | 142–145 |
| 659 | F | Cl | $CH_3$ | $CF_3$ | H | $CH_2Br$ | $COOC_2H_5$ | 1.5535 |
| 660 | F | Cl | $CH_3$ | $CF_3$ | H | $CH_2SCH_3$ | $COOC_2H_5$ | 103–105 |
| 661 | F | Cl | $CH_3$ | $CF_3$ | H | $CH_2SO_2CH_3$ | $COOC_2H_5$ | 73–75 |
| 662 | F | Cl | $CH_3$ | $CF_3$ | H | $C(CH_3)_2SO_2CH_3$ | $COOC_2H_5$ | 182–183 |
| 663 | F | Cl | $CH_3$ | $CF_3$ | H | $CH_2SC_2H_5$ | $COOC_2H_5$ | 1.5481 |
| 664 | F | Cl | $CH_3$ | $CF_3$ | H | $CH_2SO_2C_2H_5$ | $COOC_2H_5$ | 57–59 |
| 665 | F | Cl | $CH_3$ | $CF_3$ | H | $CHBr_2$ | $COOC_2H_5$ | 112–114 |
| 666 | F | Cl | $CH_3$ | $CF_3$ | H | CHO | $COOC_2H_5$ | Unmeasurable |
| 667 | F | Cl | $CH_3$ | $CF_3$ | H | $CH(CH_3)OH$ | $COOC_2H_5$ | 1.5378 |
| 668 | F | Cl | $CH_3$ | $CF_3$ | H | $COCH_3$ | $COOC_2H_5$ | 1.5466 |
| 669 | F | Cl | $CH_3$ | $CF_3$ | H | $CH(CH_3)Br$ | $COOC_2H_5$ | 1.5300 |
| 670 | F | Cl | $CH_3$ | $CF_3$ | H | $CH(CH_3)Cl$ | $COOC_2H_5$ | Unmeasurable |
| 671 | F | Cl | $CH_3$ | $CF_3$ | H | $CH(CH_3)CN$ | $COOC_2H_5$ | 1.5348 |
| 672 | F | Cl | $CH_3$ | $CF_3$ | H | H | $COOC_2H_5$ | 1.5468 |
| 673 | F | Cl | $CH_3$ | $CF_3$ | H | $CH_2Cl$ | $CH_2Cl$ | 202–203 |
| 674 | F | Cl | $CH_3$ | $CF_3$ | H | $CH_2SCH_3$ | $CH_2SCH_3$ | 115–116 |
| 675 | F | Cl | $CH_3$ | $CF_3$ | H | $CH_2SO_2CH_3$ | $CH_2SO_2CH_3$ | 169–171 |
| 676 | F | F | $CH_3$ | $CF_3$ | H | $COCH_3$ | H | 204–205 |
| 677 | F | F | $CH_3$ | $CF_3$ | H | $COC_2H_5$ | H | 136–137 |
| 678 | F | F | $CH_3$ | $CF_3$ | H | $CH(CH_3)OCH_3$ | H | 1.5220 |

TABLE 22

| Comp. Nos. | X | Y | $R^1$ | $R^2$ | $R^3$ | $R^4$ | $R^5$ | m.p. (°C.) RI $n_D^{20}$ |
|---|---|---|---|---|---|---|---|---|
| 679 | F | F | $CH_3$ | $CF_3$ | H | $CH(CH_3)OC_2H_5$ | H | |
| 680 | F | F | $CH_3$ | $CF_3$ | H | $CH(CH_2H_5)OH$ | H | 137–138 |
| 681 | F | F | $CH_3$ | $CF_3$ | H | $CH(CH=CH_2)OH$ | H | 1.5090 |
| 682 | F | F | $CH_3$ | $CF_3$ | H | $CH(CH_3)SCH_3$ | H | 1.5415 |
| 683 | F | F | $CH_3$ | $CF_3$ | H | $CH(CH_3)SOCH_3$ | H | 45 |
| 684 | F | F | $CH_3$ | $CF_3$ | H | $CH(CH_3)SO_2CH_3$ | H | 79–80 |
| 685 | F | F | $CH_3$ | $CF_3$ | H | $C(CH_3)_2SO_2CH_3$ | H | 108–111 |
| 686 | F | F | $CH_3$ | $CF_3$ | H | $CH(CH_3)SC_2H_5$ | H | 1.5345 |
| 687 | F | F | $CH_3$ | $CF_3$ | H | $CH(CH_3)SOC_2H_5$ | H | |
| 688 | F | F | $CH_3$ | $CF_3$ | H | $CH(CH_3)SO_2C_2H_5$ | H | 72–73 |
| 689 | F | F | $CH_3$ | $CF_3$ | H | $CH(C_2H_5)SCH_3$ | H | 50 |
| 690 | F | F | $CH_3$ | $CF_3$ | H | $CH(C_2H_5)SOCH_3$ | H | 1.5251 |
| 691 | F | F | $CH_3$ | $CF_3$ | H | $CH(C_2H_5)SO_2CH_3$ | H | 1.5170 |
| 692 | F | F | $CH_3$ | $CF_3$ | H | $CH(C_2H_5)SC_2H_5$ | H | 1.5339 |
| 693 | F | F | $CH_3$ | $CF_3$ | H | $CH(C_2H_5)SOC_2H_5$ | H | 1.5325 |
| 694 | F | F | $CH_3$ | $CF_3$ | H | $CH(C_2H_5)SO_2C_2H_5$ | H | 1.5250 |
| 695 | F | F | $CH_3$ | $CF_3$ | H | $CH(CH_3)CN$ | H | 55 |
| 696 | F | F | $CH_3$ | $CF_3$ | H | $CH(CH_3)CONH_2$ | H | |
| 697 | F | F | $CH_3$ | $CF_3$ | H | $CH(CH_3)SH$ | H | |
| 698 | Cl | Cl | $CH_3$ | $CF_3$ | H | $CH_3$ | H | 136–137 |
| 699 | Cl | Cl | $CH_3$ | $CF_3$ | H | $C_2H_5$ | H | 148–149 |
| 700 | Cl | Cl | $CH_3$ | $CF_3$ | H | $C_3H_7$ | H | 114–115 |
| 701 | Cl | Cl | $CH_3$ | $CF_3$ | H | $C_3H_7$—i | H | 1.5435 |
| 702 | Cl | Cl | $CH_3$ | $CF_3$ | H | $CH_3$ | $COCH_3$ | 1.5542 |
| 703 | Cl | Cl | $CH_3$ | $CF_3$ | H | $C_2H_5$ | $COCH_3$ | 1.5495 |
| 704 | Cl | Cl | $CH_3$ | $CF_3$ | H | $C_3H_7$ | $COCH_3$ | 1.5487 |
| 705 | F | Br | $CH_3$ | $CF_3$ | H | H | H | 137–138 |
| 706 | F | Br | $CH_3$ | $CF_3$ | H | $CH_3$ | H | 183–184 |
| 707 | F | Br | $CH_3$ | $CF_3$ | H | $C_2H_5$ | H | 145–147 |

TABLE 22-continued

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 708 | F | Br | $CH_3$ | $CF_3$ | H | $C_3H_7$ | H | 1.5552 |
| 709 | F | Br | $CH_3$ | $CF_3$ | H | $COCH_3$ | H | 187–189 |
| 710 | F | Br | $CH_3$ | $CF_3$ | H | $COC_2H_5$ | H | 124–125 |
| 711 | F | Br | $CH_3$ | $CF_3$ | H | $CH(CH_3)OH$ | H | 144–146 |

TABLE 23

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 712 | F | Br | $CH_3$ | $CF_3$ | H | $CH(C_2H_5)OH$ | H | 1.5420 |
| 713 | F | Br | $CH_3$ | $CF_3$ | H | $CH(CH_3)OCH_3$ | H | 1.5322 |
| 714 | F | Br | $CH_3$ | $CF_3$ | H | $CH(CH_3)OC_2H_5$ | H | |
| 715 | F | Br | $CH_3$ | $CF_3$ | H | $CH(CH_3)SCH_3$ | H | |
| 716 | F | Br | $CH_3$ | $CF_3$ | H | $CH(CH_3)SOCH_3$ | H | 88–90 |
| 717 | F | Br | $CH_3$ | $CF_3$ | H | $CH(CH_3)SO_2H_3$ | H | 107–109 |
| 718 | F | Br | $CH_3$ | $CF_3$ | H | $CH(CH_3)SC_2H_5$ | H | |
| 719 | F | Br | $CH_3$ | $CF_3$ | H | $CH(CH_3)SOC_2H_5$ | H | 1.5561 |
| 720 | F | Br | $CH_3$ | $CF_3$ | H | $CH(CH_3)SO_2C_2H_5$ | H | 1.5382 |
| 721 | F | Br | $CH_3$ | $CF_3$ | H | $CH(C_2H_5)SCH_3$ | H | |
| 722 | F | Br | $CH_3$ | $CF_3$ | H | $CH(C_2H_5)SOCH_3$ | H | |
| 723 | F | Br | $CH_3$ | $CF_3$ | H | $CH(C_2H_5)SO_2CH_3$ | H | |
| 724 | F | Br | $CH_3$ | $CF_3$ | H | $CH_3$ | $COCH_3$ | 1.5500 |
| 725 | F | Br | $CH_3$ | $CF_3$ | H | $C_2H_5$ | $COCH_3$ | 1.5460 |
| 726 | F | Br | $CH_3$ | $CF_3$ | H | $C_3H_7$ | $COCH_3$ | 1.5408 |
| 727 | F | H | $CH_3$ | $CF_3$ | H | $C_2H_5$ | H | 129–130 |
| 728 | F | Cl | $NH_2$ | $CF_3$ | H | H | H | |
| 729 | F | Cl | $NH_2$ | $CF_3$ | H | $CH_3$ | H | |
| 730 | F | Cl | $NH_2$ | $CF_3$ | H | $C_2H_5$ | H | 145–147 |
| 731 | F | Cl | $NH_2$ | $CF_3$ | H | $C_3H_7$ | H | |
| 732 | F | Cl | $NH_2$ | $CF_3$ | H | $CH(CH_3)OH$ | H | |
| 733 | F | Cl | $NH_2$ | $CF_3$ | H | $CH(CH_3)SCH_3$ | H | |
| 734 | F | Cl | $NH_2$ | $CF_3$ | H | $CH(CH_3)SO_2CH_3$ | H | |
| 735 | F | Cl | $NH_2$ | $CF_3$ | H | $CH(C_2H_5)SCH_3$ | H | |
| 736 | F | Cl | $NH_2$ | $CF_3$ | H | $CH(C_2H_5)SO_2H_3$ | H | |
| 737 | F | Cl | $NH_2$ | $CF_3$ | H | $CH(CH_3)OCH_3$ | H | |
| 738 | F | Cl | $NH_2$ | $CF_3$ | H | $COCH_3$ | H | |
| 739 | F | F | $NH_2$ | $CF_3$ | H | H | H | |
| 740 | F | F | $NH_2$ | $CF_3$ | H | $CH_3$ | H | |
| 741 | F | F | $NH_2$ | $CF_3$ | H | $C_2H_5$ | H | |
| 742 | F | F | $NH_2$ | $CF_3$ | H | $C_3H_7$ | H | |
| 743 | F | F | $NH_2$ | $CF_3$ | H | $COCH_3$ | H | |
| 744 | F | F | $NH_2$ | $CF_3$ | H | $CH(CH_3)OH$ | H | |

TABLE 24

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 745 | F | F | $NH_2$ | $CF_3$ | H | $CH(CH_3)SCH_3$ | H | |
| 746 | F | F | $NH_2$ | $CF_3$ | H | $CH(CH_3)SO_2CH_3$ | H | |
| 747 | F | F | $NH_2$ | $CF_3$ | H | $CH(C_2H_5)SCH_3$ | H | |
| 748 | F | F | $NH_2$ | $CF_3$ | H | $CH(C_2H_5)SO_2CH_3$ | H | |
| 749 | F | F | $NH_2$ | $CF_3$ | H | $CH(CH_3)OCH_3$ | H | |
| 750 | Cl | F | $CH_3$ | $CF_3$ | H | $C_2H_5$ | H | Unmeasurable |
| 751 | F | Cl | $CH_3$ | $CF_3$ | H | $CH_3$ | NHOH | 107–109 |
| 752 | F | Cl | $CH_3$ | $CF_3$ | H | $CH(CH_3)SCH_2CF_3$ | H | 1.5351 |
| 753 | F | Cl | $CH_3$ | $CF_3$ | H | $CH(CH_3)SOCH_2CF_3$ | H | 73–75 |
| 754 | F | Cl | $CH_3$ | $CF_3$ | H | $CH(CH_3)SO_2CH_2CF_3$ | H | 128–129 |
| 755 | F | Cl | $CH_3$ | $CF_3$ | H | $CH(C_2H_5)SCH_2CF_3$ | H | |
| 756 | F | Cl | $CH_3$ | $CF_3$ | H | $CH(C_2H_5)SOCH_2CF_3$ | H | |
| 757 | F | Cl | $CH_3$ | $CF_3$ | H | $CH(C_2H_5)SO_2CH_2CF_3$ | H | Unmeasurable |

TABLE 24-continued

| Comp. Nos. | X | Y | $R^1$ | $R^2$ | $R^3$ | $R^4$ | $R^5$ | m.p. (° C.) RI $n_D^{20}$ |
|---|---|---|---|---|---|---|---|---|
| 758 | F | Cl | $CH_3$ | $CF_3$ | H | $CH(CH=CH_2)SCH_2CF_3$ | H | |
| 759 | F | Cl | $CH_3$ | $CF_3$ | H | $CH(CH=CH_2)SOCH_2CF_3$ | H | |
| 760 | F | Cl | $CH_3$ | $CF_3$ | H | $CH(CH=CH_2)SO_2CH_2CF_3$ | H | |
| 761 | F | Cl | $CH_3$ | $CF_3$ | H | $CH(C≡CH)SCH_2CF_3$ | H | |
| 762 | F | Cl | $CH_3$ | $CF_3$ | H | $CH(C≡CH)SOCH_2CF_3$ | H | |
| 763 | F | Cl | $CH_3$ | $CF_3$ | H | $CH(C≡CH)SO_2CH_2CF_3$ | H | |
| 764 | F | Cl | $CH_3$ | $CF_3$ | H | $CH(C_2H_5)OCH_3$ | H | 1.5158 |
| 765 | F | Cl | $CH_3$ | $CF_3$ | H | $CH(CH_2)OCH_2CF_3$ | H | 1.5165 |
| 766 | F | Cl | $CH_3$ | $CF_3$ | H | $CH(CH_2)OCH_2CH_2F$ | H | 1.5312 |
| 767 | F | Cl | $CH_3$ | $CF_3$ | H | $CH(CH=CH_2)OCH_2CF_3$ | H | |
| 768 | F | Cl | $CH_3$ | $CF_3$ | H | $CH(C≡CH)OCH_2CF_3$ | H | |
| 769 | F | Cl | $CH_3$ | $CF_3$ | H | $CH(C_2H_5)OCH_2CF_3$ | H | |
| 770 | F | Cl | $CH_3$ | $CF_3$ | H | $CH(CH_3)SCSN(C_2H_5)_2$ | H | 1.5537 |
| 771 | F | F | $CH_3$ | $CF_3$ | H | $CH(C_2H_5)OCH_3$ | H | 1.5216 |
| 772 | F | Cl | $CH_3$ | $CF_3$ | H | $CBr_2C_2H_5$ | H | 197–199 |

Now, common processes for producing the compounds of the present invention will be described.

Process 1

Among compounds represented by the general formula (1), a compound of the present invention wherein $R^4$ is an alkyl group, a cycloalkyl group or a benzyl group which may be substituted, and $R^5$ is a hydrogen atom, an alkyl group, a benzyl group which may be substituted, or a phenyl group which may be substituted, can be produced as follows.

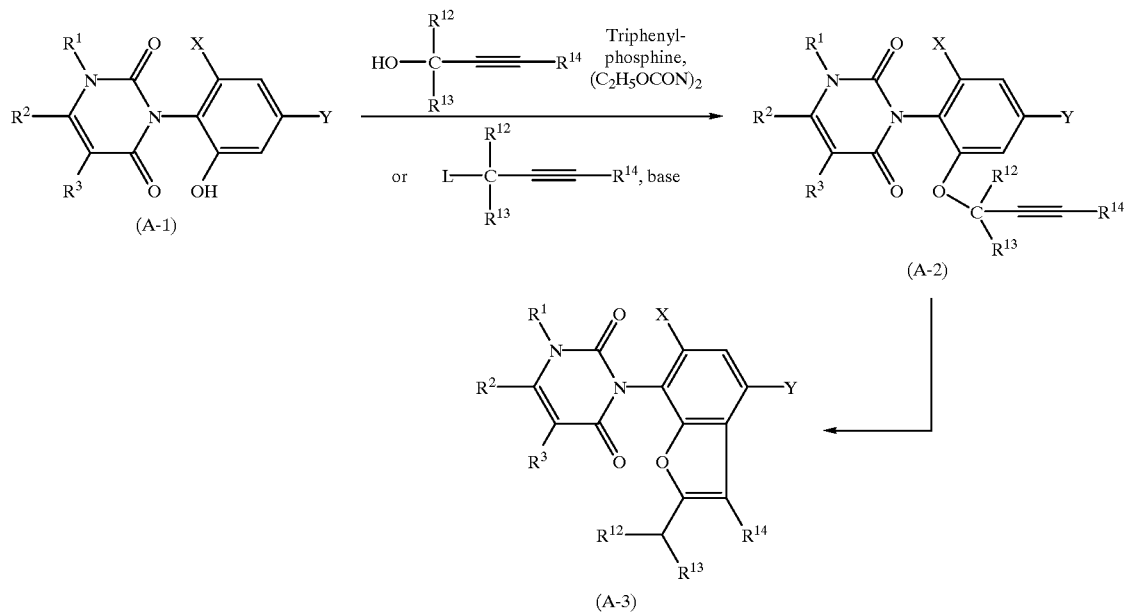

(In the formulae, each of $R^1$, $R^2$, $R^3$, X and Y is as defined above, L represents a leaving group, each of $R^{12}$ and $R^{13}$ is a hydrogen atom, an alkyl group or a phenyl group which may be substituted, or $R^{12}$ and $R^{13}$ are mutually connected to represent a carbon ring, and $R^{14}$ is a hydrogen atom, an alkyl group, a benzyl group which may be substituted, or a phenyl group which may be substituted.)

The compound (A-2) can be obtained by a known method (Synthesis, 1981, 1–28) wherein the compound (A-1) is reacted with the propargyl alcohol derivative in the presence of an azo compound and triphenylphosphine, or by a conventional method wherein it is condensed with the propargyl derivative containing the leaving group in the presence of a base. Further, the compound (A-3) can be produced by cyclizing the compound (A-2) in a solvent in the presence of a base.

Here, as the solvent, an aromatic hydrocarbon such as toluene, xylene or mesitylene, an ether such as 1,4-dioxane or tetrahydrofuran, an amide such as N,N-dimethylformamide, a sulfur compound such as dimethylsulfoxide or sulfolane, an aromatic nitrogen-containing compound such as quinoline or pyridine, or an aniline derivative such as N,N-diethylaniline or N,N-dimethylaniline, may be mentioned. Especially for the ring closure reaction of the compound (A-2), N,N-diethylaniline is preferred. Further, as the azo compound, diethyl azodicarboxylate is preferred. As the base, a hydride, hydroxide, carbonate, hydrogencarbonate or organic acid salt of an alkali metal or an alkaline earth metal, a metal fluoride compound such as cesium fluoride or potassium fluoride, or an organic base such as triethylamine, 1,8-diazabicyclo[5.4.0]-7-undecene or pyridine, may be mentioned. The reaction can be carried out at a temperature from ice temperature to the refluxing temperature of the solvent.
Process 2
Among compounds represented by the general formula (1), compounds (B-7) and (C-3) of the present invention wherein $R^1$ is a hydrogen atom, can be produced as follows.
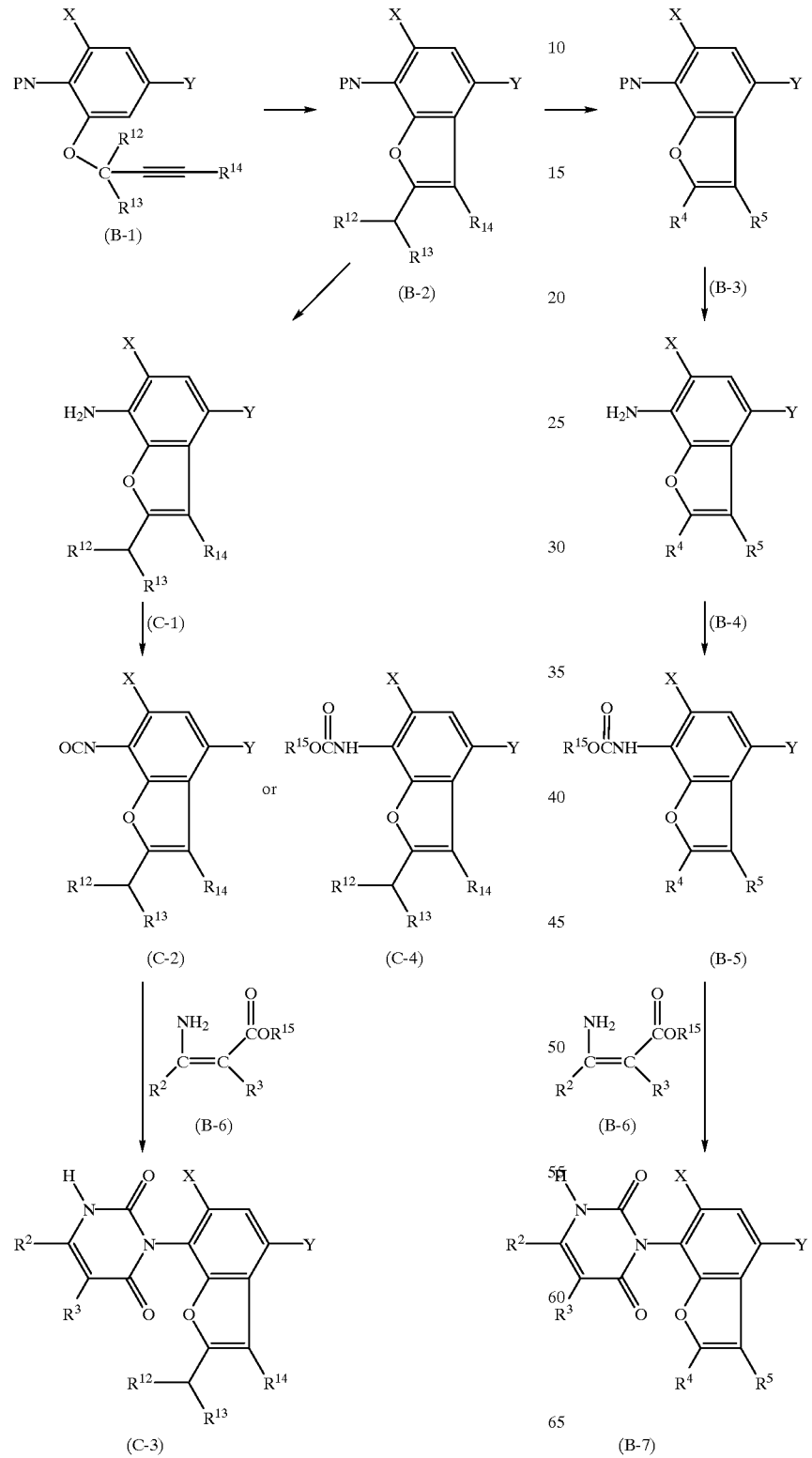

(In the formulae, each of $R^2$, $R^3$, $R^4$, $R^5$. $R^{12}$, $R^{13}$, $R^{14}$, X and Y, is as defined above, $R^{15}$ is an alkyl group, a phenyl group which may be substituted, or a benzyl group which may be substituted, and PN represents an amino group having a protecting group such as a mono- or di-acylamino group, a mono- or di-haloalkylcarbonylamino group, a mono- or di-alkylsulfonylamino group, a mono-or di-haloalkylsulfonylamino group, a tetrahydrophthalimino group or a phthalimino group.)

The compound (B-2) can be produced by ring-closing the compound (B-1) in the same manner as in the method described in Process 1. Then, the compound (B-2) is converted to the compound (B-3) in accordance with e.g. the after-mentioned processes (Processes 5 to 35) for producing uracil derivatives or a method disclosed in a literature (Methoden del Organitien Chemie, vol. E6b1, p.33–162, 1994), and its protecting group is removed to produce the aniline compound (B-4). The aniline compound (B-4) is reacted with e.g. phenyl chlorocarbonate by a conventional method to obtain a carbamate compound (B-5), which is then reacted with the compound (B-6), whereupon the product is subjected to acid treatment to obtain the desired compound (B-7).

Otherwise, the aniline compound (C-1) can be produced by removing the protecting group of the compound (B-2). The aniline compound (C-1) is reacted with e.g. phosgene to obtain a compound (C-2), or it is reacted with e.g. phenyl chlorocarbonate to obtain a compound (C-4), and then these compounds are, respectively, reacted with the compound (B-6), whereupon the obtained products are subjected to acid treatment to obtain the desired compound (C-3).

A method for removing the protecting group P may be by means of hydrolysis in the presence of a base, or in a case where the protecting group is a tetrahydrophthalimino group or a phthalimino group, it can be removed by reacting with hydrazine.

Production of the compound (B-5) or the compound (C-4), is carried out usually by a reaction in a solvent in the presence of a base at a reaction temperature of from 0 to 120° C., preferably from 20 to 80° C. for from 0.5 to 24 hours. The amounts of the reagents used for the reaction are from 1 to 2 equivalents of the chlorocarbonate derivative and from 1 to 1.5 equivalents of the base, per equivalent of the compound (B-4) or the compound (C-1). As the base, an inorganic base such as potassium carbonate or sodium hydride, or an organic base such as triethylamine, 1,8-diazabicyclo[5.4.0]-7-undecene or pyridine, may be mentioned. As the solvent, an ether such as diethyl ether or tetrahydrofuran, a halogenated hydrocarbon such as chloroform or carbon tetrachloride, an amide such as N,N-dimethylformamide, a sulfur compound such as dimethylsulfoxide or sulfolane, an aromatic hydrocarbon such as benzene or toluene, or a mixture thereof, may be mentioned.

Production of the compound (C-2) is carried out usually by a reaction in a solvent at a reaction temperature of from 0 to 120° C., preferably from 20 to 100° C., for from 0.5 to 24 hours. The amounts of the reagents used for the reaction are from 2 to 10 equivalents of phosgene and from 1 to 1.5 equivalents of the base, per equivalent of the compound (C-1). As the solvent, a halogenated hydrocarbon such as chloroform or carbon tetrachloride, an aromatic hydrocarbon such as benzene or toluene, an aliphatic hydrocarbon such as hexane or heptane, or a mixture thereof, may be mentioned.

Production of the compound (B-7) from the compound (B-5), or production of the compound (C-3) from the compound (C-4), is carried out usually by a reaction in a solvent in the presence of a base at a reaction temperature of from 0 to 150° C., preferably from 20 to 120° C., for from 0.5 to 24 hours. The amounts of the reagents used for the reaction are from 1 to 10 equivalents of the compound (B-6) and from 1 to 10 equivalents of the base, per equivalent of the compound (B-5) or the compound (C-4). As the base, an inorganic base such as potassium hydride or sodium hydride, or an organic base such as 1,8-diazabicyclo[5.4.0]-7-undecene, may be mentioned. As the solvent, an ether such as diethyl ether or tetrahydrofuran, an aromatic hydrocarbon such as benzene or toluene, an aliphatic hydrocarbon such as hexane or heptane, an amide such as N,N-dimethylformamide, a sulfur compound such as dimethylsulfoxide or sulfolane, or a mixture thereof, may be mentioned.

Production of the compound (C-3) from the compound (C-2) is carried out usually by a reaction in a solvent in the presence of a base at a reaction temperature of from 0 to 60° C., preferably from 5 to 30° C., for from 0.5 to 24 hours. The amounts of the reagents used for the reaction are from 1 to 1.5 equivalents of the compound (B-6) and from 1 to 1.5 equivalents of the base, per equivalent of the compound (C-2). As the base, an inorganic base such as potassium hydride or sodium hydride, may, for example, be mentioned. As the solvent, an ether such as diethyl ether or tetrahydrofuran, an aromatic hydrocarbon such as benzene or toluene, an aliphatic hydrocarbon such as hexane or heptane, an amide such as N,N-dimethylformamide, a sulfur compound such as dimethylsulfoxide or sulfolane, or a mixture thereof, may be mentioned.

The starting material compound (B-1) can be produced as follows.

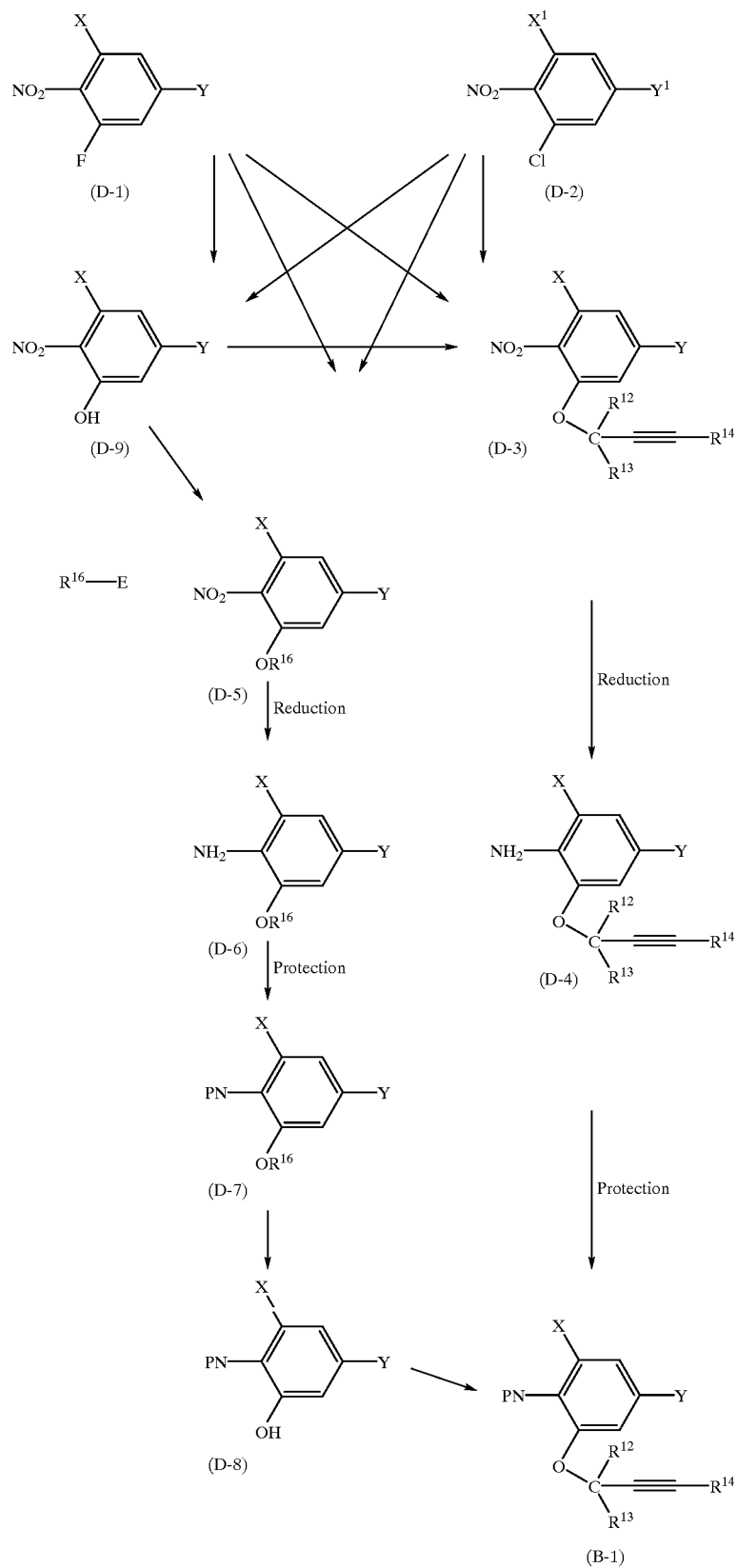

(In the formulae, each of $R^{12}$, $R^{13}$, $R^{14}$, PN, X and Y is as defined above, $R^{16}$ is an alkyl group or a benzyl group which may be substituted, $X^1$ and $Y^1$ represent X and Y other than a fluorine atom, respectively, and E is a chlorine atom, a bromine atom, an iodine atom or a methanesulfonyloxy group.)

The compound (D-3) can be produced by reacting the compound (D-1) or the compound (D-2) with the corresponding alkynyl alcohol in the presence of a base. Otherwise, the compound (D-3) can be produced in accordance with the method described in Process 1, after producing the compound (D-9) by hydrolyzing the compound (D-1) or the compound (D-2) in the presence of a base. Then, the obtained (D-3) is reduced to produce the compound (D-4), and then the nitrogen atom is protected by a protecting group, to obtain the compound (B-1).

Further, the compound (D-5) can be produced by reacting the compound (D-1) or the compound (D-2) with the corresponding alcohol in the presence of a base, or by reacting the compound (D-9) with the compound $R^{16}$-E. Then, the compound (D-5) is reduced to obtain the compound (D-6), and then the nitrogen atom is protected by a protecting group, to obtain the compound (D-7). Further, $R^{16}$ is removed from the compound (D-7) to obtain the compound (D-8), and then the compound (B-1) can be produced in accordance with the method described in Process 1.

When $R^{16}$ is an alkyl group, it can be removed by means of a dealkylating agent such as boron tribromide, and when $R^{16}$ is a benzyl group which may be substituted, it can be removed by hydrogenation under atmospheric pressure.

Further, a compound [which corresponds to (D-1)] wherein X is a fluorine atom, and Y is a chlorine atom or a bromine atom, can be produced by chlorinating or brominating the 4-position of the phenyl ring of 2,6-difluoroaniline, with a halogenating agent such as N-chlorosuccinic imide (NCS) or N-bromosuccinic imide (NBS), followed by oxidation with an oxidizing agent such as metachloroperbenzoic acid.

For example, a compound [which corresponds to (D-1)] wherein X is a fluorine atom, and Y is a cyano group, can be produced by oxidizing 2,6-difluoro-4-cyanoaniline, with an oxidizing agent such as metachloroperbenzoic acid.

Process 3

Among compounds represented by the general formula (1), a compound (E-2) or (E-3) of the present invention wherein $R^1$ is an alkyl group or a haloalkyl group, can be produced as follows.

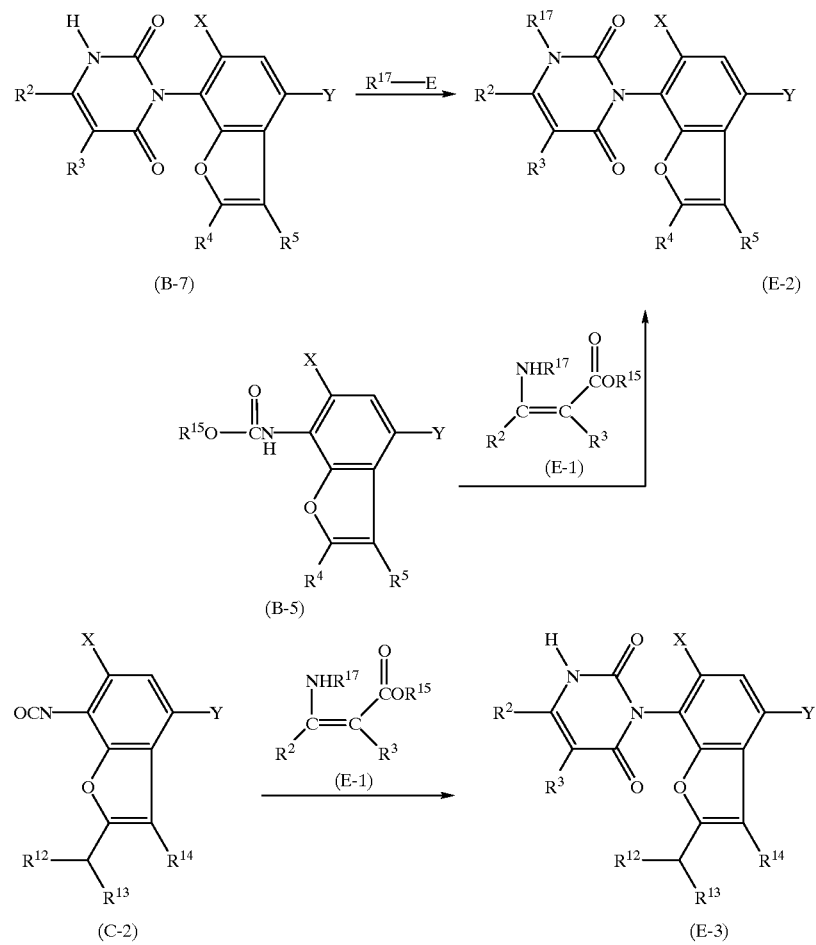

(In the formulae, each of $R^2$, $R^3$, $R^4$, $R^5$, $R^{12}$, $R^{13}$, $R^{14}$, $R^{15}$, E, X and Y, is as defined above, and $R^{17}$ is an alkyl group or a haloalkyl group.)

The compound (E-2) can be produced by reacting the compound $R^{17}$-E with the compound (B-7) of the present invention produced by the above Process 2 or with the compound (B-7) of the present invention which corresponds to the compound (A-3) produced by the above Process 1, wherein $R^1$ is a hydrogen atom, or by reacting the compound (B-5) with the compound (E-1) in accordance with the method shown in Process 2.

Further, the compound (E-3) can be produced by reacting the compound (C-2) with the compound (E-1) in accordance with the method shown in Process 2.

Production of the compound (E-2) from the compound (B-7) is carried out usually by a reaction in a solvent in the presence of a base at a reaction temperature of from 0 to 100° C. for from 0.5 to 24 hours. The amounts of the reagents used for the reaction are from 1 to 10 equivalents of the compound ($R^1$-E) and from 1 to 1.5 equivalents of the base, per equivalent of the compound (B-7). As the base, an inorganic base such as potassium carbonate, potassium hydride or sodium hydride, or an alkali metal alkoxide such as sodium ethoxide or sodium methoxide, may, for example, be mentioned. As the solvent, a halogenated hydrocarbon such as chloroform or carbon tetrachloride, an ether such as diethyl ether or tetrahydrofuran, an aromatic hydrocarbon such as benzene or toluene, an aliphatic hydrocarbon such as hexane or heptane, a ketone such as acetone or methyl isobutyl ketone, an ester such as ethyl acetate, an amide such as N,N-dimethylformamide, a sulfur compound such as dimethylsulfoxide or sulfolane, or a mixture thereof, may be mentioned.

Process 4

Among compounds represented by the general formula (1), the compound (G-1) of the present invention wherein $R^1$ is an amino group, can be prepared as follows.

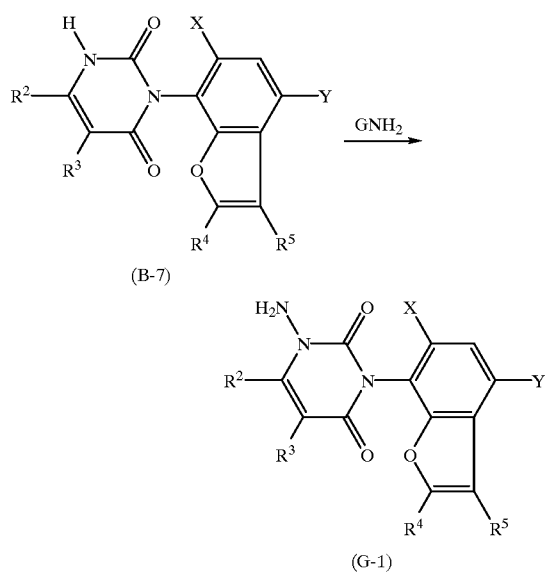

(in the formulae, each of $R^2$, R3 $R^4$, $R^5$, X and Y, is as defined above, G is a methanesulfonyloxy group, a p-toluenesulfonyloxy group, or a 2,4-dinitrophenoxy group.)

The compound (G-1) can be prepared by reacting the compound G-NH$_2$ with the compound (B-7) of the present invention produced by the above Process 2, or with the compound (B-7) of the present invention which corresponds to the compound (A-3) produced by the above Process 1 wherein $R^1$ is a hydrogen.

This reaction is carried out usually in a solvent in the presence of a base at a reaction temperature of from 0 to 100° C. for from 0.5 to 24 hours. The amounts of the reagents used for the reaction are from 1 to 10 equivalents of the compound (G-NH$_2$) and from 1 to 1.5 equivalents of the base, per equivalent of the compound (B-7). As the base, an inorganic base such as potassium carbonate, potassium hydride or sodium hydride, or an alkali metal alkoxide such as sodium ethoxide or sodium methoxide, may, for example, be mentioned. As the solvent, a halogenated hydrocarbon such as chloroform or carbon tetrachloride, an ether such as diethyl ether or tetrahydrofuran, an aromatic hydrocarbon such as benzene or toluene, an aliphatic hydrocarbon such as hexane or heptane, a ketone such as acetone or methyl isobutyl ketone, an ester such as ethyl acetate, an amide such as N,N-dimethylformamide, a sulfur compound such as dimethylsulfoxide or sulfolane, or a mixture thereof, may be mentioned.

Process 5

Among compounds represented by the general formula (1), a compound of the present invention wherein R4 is a haloalkyl group, can be prepared by reacting a compound represented by the general formula (I-1):

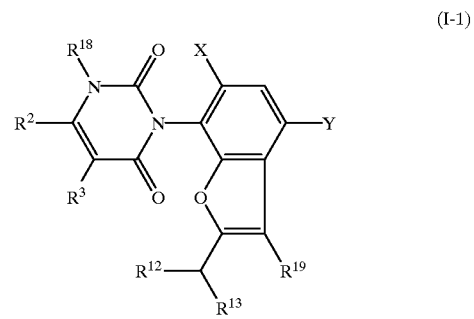

(wherein, each of $R^2$, $R^3$, $R^{12}$, $R^{13}$, X and Y, is as defined above, $R^{18}$ is an amino group, an alkyl group or a haloalkyl group, and $R^{19}$ is a hydrogen atom, an alkoxy group, a haloalkoxy group, a phenylsulfonyl group which may be substituted, a halogen atom, a phenyl group which may be substituted, a nitro group, an alkoxycarbonyl group or a benzyl group which may be substituted), with a halogenating agent, as a mixture of compounds represented by the general formulae:

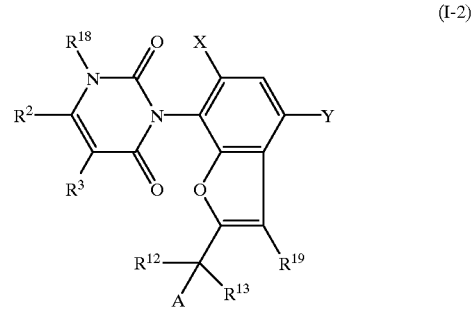

-continued

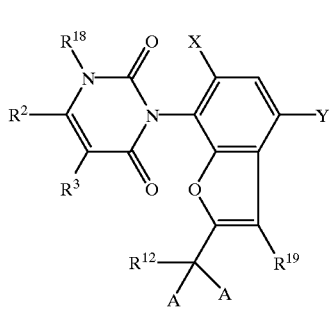

(I-3)

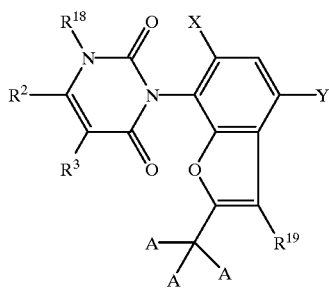

(I-4)

(wherein each of $R^1$, $R^2$, $R^3$, $R^{12}$, $R^{13}$, $R^{18}$, $R^{19}$, X and Y, is as defined above, and A is a halogen atom). [However, the compound (I-3) can be produced only when $R^{13}$ of the compound (I-1) is a hydrogen atom, and the compound (I-4) can be produced only when $R^{12}$ and $R^{13}$ in the compound (I-1) are both hydrogen atoms.] The desired compound can be obtained by isolating and purifying the mixture of these compounds.

This reaction is carried out in a solvent in the presence or absence of a catalyst at a reaction temperature of from 0 to 150° C., preferably from 30 to 100° C., for from 0.5 to 24 hours. The amounts of the reagents used for the reaction are from 1 to 10 equivalents of the halogenating agent and from 0.01 to 0.5 equivalent of the catalyst, per equivalent of the compound (I-1). As the halogenating agent, a halogen such as bromine or chlorine, an N-halosuccinic imide such as N-bromosuccinic imide, or a pyridine salt such as pyridinium perbromide, may, for example, be mentioned. As the solvent, a halogenated hydrocarbon such as chloroform or carbon tetrachloride, a carboxylic acid such as formic acid or acetic acid, an amide such as N,N-dimethylformamide, or a sulfur compound such as dimethylsulfoxide or sulfolane, may, for example, be mentioned. As the catalyst, benzoyl peroxide, α, α'-azobisisobutyronitrile, or a mixture thereof, may be mentioned.

Process 6

Among compounds represented by the general formula (1), a compound of the present invention wherein $R^4$ is a formyl group, can be prepared by hydrolyzing a compound which is the compound (I-3) produced by the above Process 5 wherein $R^{12}$ is a hydrogen atom, by a conventional method.

Process 7

Among compounds represented by the general formula (1), a compound of the present invention wherein $R^4$ is a carboxyl group, can be prepared by hydrolyzing the compound (I-4) produced by the above Process 5, or by oxidizing a compound of the present invention wherein $R^4$ is a formyl group, produced by the above Process 6, with an oxidizing agent such as a Jones' reagent (a mixed solution comprising chromium trioxide, sulfuric acid and water; see Organic Syntheses col. Vol. 1).

Process 8

Among compounds represented by the general formula (I), a compound of the present invention wherein $R^4$ is a hydrogen atom, can be prepared by decarboxylating the compound of the present invention wherein $R^4$ is a carboxyl group, produced by the above Process 7, in the presence of a copper catalyst.

Process 9

Among compounds represented by the general formula (1), a compound of the present invention wherein $R^4$ is a group of —$COR^{20}$, can be prepared by subjecting the compound wherein $R^4$ is a hydrogen atom, produced by the above Process 8 and the corresponding acid anhydride ($R^{20}CO)_2O$ or acid halide $R^{20}$ $^{COL1}$, to a Friedel Crafts reaction in the presence of a Lewis acid. (In the formulae, $R^{20}$ is an alkyl group, a cycloalkyl group, a haloalkyl group or a phenyl group which may be substituted, and $L^1$ is a chlorine atom, a bromine atom or an iodine atom.)

Further, a compound of the present invention wherein $R^4$ is a group of —$COR^{12}$, can be produced by hydrolyzing the compound (I-3) produced by the above Process 5 wherein $R^{12}$ is an alkyl group or a phenyl group which may be substituted, in the same manner as in Process 6.

Process 10

Among compounds represented by the general formula (1), a compound of the present invention wherein $R^4$ is a hydroxyiminoalkyl group, a hydroxyiminohaloalkyl group, an alkoxyiminoalkyl group or an alkoxyiminohaloalkyl group, can be prepared by reacting a compound of the present invention wherein $R^4$ is an acyl group or a haloalkylcarbonyl group, produced by the above Process 6 or 9, with a compound represented by the general formula $NH_2OR^{21}$ (wherein $R^{21}$ is a hydrogen atom or an alkyl group) or its sulfate or hydrochloride.

Process 11

Among compounds represented by the general formula (1), a compound of the present invention wherein $R^4$ is a hydrazonoalkyl group, an alkylhydrazonoalkyl group, a phenylhydrazonoalkyl group which may be substituted, an alkyliminoalkyl group or a phenyliminoalkyl group which may be substituted, can be prepared by reacting a compound of the present invention wherein $R^4$ is an acyl group, produced by the above Process 6 or 9, with a compound represented by the general formula $NH_2NR^{22}$ ($R^{23}$) (wherein each of $R^{22}$ and $R^{23}$ which are the same or different, is a hydrogen atom, an alkyl group or a phenyl group which may be substituted), or its sulfate or hydrochloride.

Process 12

Among compounds represented by the general formula (1), a compound of the present invention wherein R4 is a cyano group, can be prepared by dehydrating a compound of the present invention wherein $R^4$ is a hydroxyiminomethyl group, produced by the above Process 10, in the presence of an acid catalyst such as p-toluenesulfonic acid.

Process 13

Among compounds represented by the general formula (1), a compound of the present invention wherein $R^4$ is a group of —$C(R^6)$ ($R^7$)OH, can be prepared by reacting a compound of the present invention wherein $R^4$ is a group of —$COR^6$, produced by the above Process 6 or 9, with a Grignard reagent $R^7MgL^1$. (In the formulae, $R^6$, $R^7$ and $L^1$ are as defined above.)

Process 14

Among compounds represented by the general formula (1), a compound of the present invention wherein $R^4$ is a group of —$COR^7$, can be prepared by oxidizing a compound of the present invention wherein $R^4$ is a group of —$CH(R^7)$ OH, produced by the above Process 13, with e.g. a Jones' reagent. (In the formulae, $R^7$ is as defined above.)

Process 15

Among compounds represented by the general formula (1), a compound of the present invention wherein $R^4$ is a group of —CH($R^7$)OH, can be prepared by reducing a compound of the present invention wherein $R^4$ is a group of —COR$^7$, produced by the above Process 6, 9 or 14, with a reducing agent such as diisobutylaluminum hydride. (In the formulae, $R^7$ is as defined above.)

Process 16

Among compounds represented by the general formula (1), a compound of the present invention wherein $R^4$ is a group of —C($R^6$) ($R^7$)$L^1$, can be prepared by halogenating a compound of the present invention wherein $R^4$ is a group of —C($R^6$) ($R^7$)OH, produced by the above Process 13, with a halogenating agent such as [triphenylphosphine/chloranil (tetrachlorobenzoquinone)]. (In the formulae, $R^6$, $R^7$ and $L^1$ are as defined above.)

Process 17

Among compounds represented by the general formula (1), a compound of the present invention wherein $R^4$ is a group of —C($R^6$) ($R^7$)Z$R^9$ or a group of —C($R^6$) ($R^7$)N($R^6$)$R^{24}$, can be prepared by reacting the compound (I-2) produced by the above Process 5 or the compound produced by the above Process 16, with a compound represented by the general formula $R^9$SH, $R^9$OH or $R^6$($R^{24}$)NH (wherein each of $R^6$, $R^7$, $R^9$ and Z, is as defined above, and $R^{24}$ is a hydrogen atom or an alkyl group). This reaction is carried out in a solvent in the presence or absence of a base at a reaction temperature of from 0 to 100° C., preferably from 20 to 80° C. for from 0.5 to 24 hours. As the solvent to be used for this reaction, an ether such as diethyl ether or tetrahydrofuran, an amide such as N,N-dimethylformamide, a sulfur compound such as dimethylsulfoxide or sulfolane or an aromatic hydrocarbon such as benzene or toluene, may be mentioned. As the base, a metal hydride such as sodium hydride or potassium hydride, potassium carbonate, or sodium methoxide, may, for example, be mentioned.

Process 18

Among compounds represented by the general formula (1), a compound of the present invention wherein $R^4$ is a group of —C($R^6$)($R^7$)W$R^9$, can be prepared by oxidizing a compound wherein $R^4$ is a group of —C($R^6$) ($R^7$)S$R^9$, produced by the above Process 16, with an oxidizing agent such as metachloroperbenzoic acid or potassium peroxymonosulfate (tradename: Oxone). (In the formulae, each of $R^6$, $R^7$, $R^9$ and W is as defined above.)

Process 19

Among compounds represented by the general formula (1), a compound of the present invention wherein $R^4$ is a group of —COO$R^{25}$, can be prepared by reacting a compound wherein $R^4$ is a carboxyl group, produced by the above Process 7, with a compound represented by the general formula $R^{25}$OH, in the presence of an acid catalyst, or by reacting it with a compound represented by the general formula $R^{26}$-$L^1$, in the presence of a base. (In the formulae, $L^1$ is as defined above, $R^{25}$ is an alkyl group, a haloalkyl group, a benzyl group which may be substituted, or a phenyl group which may be substituted, and $R^{26}$ is an alkyl group, a haloalkyl group, or a benzyl group which may be substituted.)

Process 20

Among compounds represented by the general formula (1), a compound of the present invention wherein $R^4$ is a carbamoyl group (having the same or different hydrogen atoms, alkyl groups or phenyl groups which may be substituted, substituted on the nitrogen atom), can be prepared by reacting a compound of the present invention wherein $R^4$ is a carboxyl group, produced by the above Process 7, with thionyl chloride, and then reacting it with a compound represented by the general formula $R^{27}$($R^{28}$)NH (wherein each of $R^{27}$ and $R^{28}$ which may be the same or different, is a hydrogen atom, an alkyl group or a phenyl group which may be substituted).

Process 21

Among compounds represented by the general formula (1), a compound of the present invention wherein $R^4$ is a group of —C($R^6$) ($R^7$)SH, can be prepared by reacting the compound (I-2) produced by the above Process 5 or a compound of the present invention produced by the above Process 16 wherein R is a group of —C($R^6$)($R^7$) $L^1$, with a thiol-modifying agent such as sodium sulfide or sodium hydrogensulfide in the presence of a base, followed by acid treatment. (In the formulae, $R^6$, $R^7$ and $L^1$ are as defined above.)

Process 22

Among compounds represented by the general formula (1), a compound of the present invention wherein $R^4$ is a group of —C($R^6$) ($R^7$)Z$R^8$, can be prepared by reacting a compound of the present invention wherein $R^4$ is a group of —CH($R^7$)OH, produced by the above Process 15, a compound of the present invention wherein $R^4$ is a group of —C($R^6$) ($R^7$)OH, produced by the above Process 13, or a compound of the present invention wherein $R^4$ is a group of —C($R^6$) ($R^7$)SH, produced by the above Process 21, with a compound represented by the general formula $R^{29}$-E or with a compound represented by the general formula $R^{30}$N=C=Z, in the presence of a base. (In the formulae, $R^6$, $R^7$, $R^8$, Z and E are as defined above, $R^{29}$ is an alkyl group, a cycloalkyl group, haloalkyl group, an alkoxycarbonylalkyl group, a hydroxycarbonylalkyl group, a monoalkylcarbamoylalkyl group, a dialkylcarbamoylalkyl group, an acyl group, an alkylsulfonyl group, a haloalkylsulfonyl group, a haloalkylcarbonyl group, a dialkylcarbamoyl group, a dialkylthiocarbamoyl group or a benzoyl group which may be substituted, and $R^{30}$ is an alkyl group.)

Process 23

Among compounds represented by the general formula (1), a compound of the present invention wherein $R^4$ is a group of —C($R^6$) ($R^7$)N($R^6$)$R^{31}$, can be prepared by reacting a compound of the present invention wherein $R^4$ is a group of —C($R^6$) ($R^7$)NH($R^6$), produced by the above Process 17, with a compound represented by the general formula $R^{31}$-E, in the presence of a base. (In the formulae, $R^6$, $R^7$ and E are as defined above, and $R^{31}$ is an alkyl group, an acyl group, an alkylsulfonyl group, a haloalkylsulfonyl group, or a haloalkylcarbonyl group.)

Process 24

Among compounds represented by the general formula (1), a compound of the present invention wherein $R^5$ is a group of —COR$^{20}$, can be prepared by subjecting a compound of the present invention wherein $R^5$ is a hydrogen atom and a corresponding acid hydride $R^{20}$CO$L^1$, to a Friedel Crafts reaction in the presence of a Lewis acid. (In the formulae, $R^{20}$ and $L^1$ are as defined above.)

Process 25

Among compounds represented by the general formula (1), a compound of the present invention wherein $R^5$ is a formyl group, can be prepared by e.g. a known method [Jikken Kagaku Kouza (4th edition), vol. 21, p. 110] which comprises reacting a compound of the present invention wherein $R^5$ is a hydrogen atom, with a dichloromethylalkyl ether in the presence of a Lewis acid.

Using compounds of the present invention wherein $R^5$ is an alkyl group, which can be produced by the above Processes 1 to 4, or compounds of the present invention wherein $R^5$ is an acyl group, which can be prepared by the above Process 24 or 25, as starting materials, compounds of the present invention having various substituents for $R^5$ can be prepared in the same manner as for $R^4$, in accordance with any suitable processes described in the foregoing.

Process 26

Among compounds represented by the general formula (1), a compound of the present invention wherein $R^4$ or $R^5$ is a group of —$CSR^{20}$, can be prepared by thiocarbonyl-modifying a compound of the present invention wherein $R^4$ or $R^5$ is a group of —$COR^{20}$, produced by the above process, with e.g. phosphorous pentasulfide, a Lawesson's reagent [(2,4-bis(4-methoxyphenyl)-1,3-dithia-2,4-diphosphethane-2,4-disulfide]. (In the formulae, $R^{20}$ is as defined above.)

Process 27

Among compounds represented by the general formula (1), a compound of the present invention wherein $R^4$ or $R^5$ is a halogen atom, can be prepared by halogenating a compound of the present invention wherein $R^4$ or $R^5$ is a hydrogen atom, produced by the above process, with a halogenating agent such as bromine.

Process 28

Among compounds represented by the general formula (1), a compound of the present invention wherein $R^4$ or $R^5$ is a nitro group, can be prepared by nitration of a compound of the present invention wherein $R^4$ or $R^5$ is a hydrogen atom, produced by the above process, by a conventional method.

Process 29

Among compounds represented by the general formula (1), a compound of the present invention wherein $R^4$ or $R^5$ is a cyanoalkyl group, can be prepared by cyano-modifying a compound of the present invention wherein $R^4$ or $R^5$ is a haloalkyl group, produced by the above process, with a cyano-modifying agent such as potassium cyanide.

Process 30

Among compounds represented by the general formula (1), a compound of the present invention wherein $R^4$ or $R^5$ is a carbamoylalkyl group, can be prepared by hydrolyzing a cyano group of a compound of the present invention wherein $R^4$ or $R^5$ is a cyanoalkyl group, produced by the above Process 29, under an acidic or basic condition.

Process 31

Among compounds represented by the general formula (1), a compound of the present invention wherein $R^4$ or $R^5$ is a thiocyanatealkyl group, can be prepared by thiocyanate-modifying a compound of the present invention wherein $R^4$ or $R^5$ is a haloalkyl group, produced by the above process, with a thiocyanate-modifying agent such as potassium thiocyanate.

Process 32

Among compounds represented by the general formula (1), a compound of the present invention wherein $R^4$ or $R^5$ is a group of —$CR^{32}$=$CR^{33}R^{34}$, can be prepared by a Witig reaction which comprises reacting a compound of the present invention wherein $R^4$ or $R^5$ is an acyl group of —$COR^{32}$, produced by the above process, with a phosphonium reagent $[Ph_3P^{30}CHR^{33}R^{34}]L^{1-}$, in the presence of a base. ($L^1$ is as defined above, and each of $R^{32}$, $R^{33}$ and $R^{34}$ which are the same or different, is a hydrogen atom or an alkyl group, and $Ph_3P$ represents a triphenylphosphine.)

Process 33

Among compounds represented by the general formula (1), a compound of the present invention wherein $R^4$ or $R^5$ is an oxiranyl group which may be substituted by an alkyl group, can be prepared by oxidizing a compound of the present invention wherein $R^4$ or $R^5$ is a group of —$CR^{32}$=$CR^{33}R^{34}$, produced by the above Process 32, with an oxidizing agent such as metachloroperbenzoic acid. (Each of $R^{32}$, $R^{33}$ and $R^{34}$ is as defined above.)

Process 34

Among compounds represented by the general formula (1), a compound of the present invention wherein $R^5$ is an alkoxy group, a haloalkoxy group, an alkenyloxy group, an alkynyloxy group or an alkoxycarbonylalkoxy group, can be produced by reacting a compound wherein $R^5$ is a hydroxyl group, with a compound represented by the general formula $R^{35}$-E (wherein E is as defined above, and $R^{35}$ is an alkyl group, an alkenyl group, an alkynyl group, an alkoxycarbonylalkyl group or a haloalkyl group) in the presence of a base. Further, the compound wherein $R^5$ is a hydroxyl group, can be prepared by reacting a compound of the present invention wherein $R^5$ is a nitro group, produced by the above process, with iron in the presence of e.g. an acetic acid catalyst in a solvent mixture of toluene-water.

Process 35

Among compounds represented by the general formula (1), a compound of the present invention wherein $R^5$ is a hydroxyamino group, can be prepared by reducing a compound of the present invention wherein $R^5$ is a nitro group, produced by the above process, with iron in the presence of e.g. an acetic acid catalyst in a solvent mixture of ethyl acetate-water.

Further, the compound (A-1) as the starting material in Process 1, can be produced as follows.

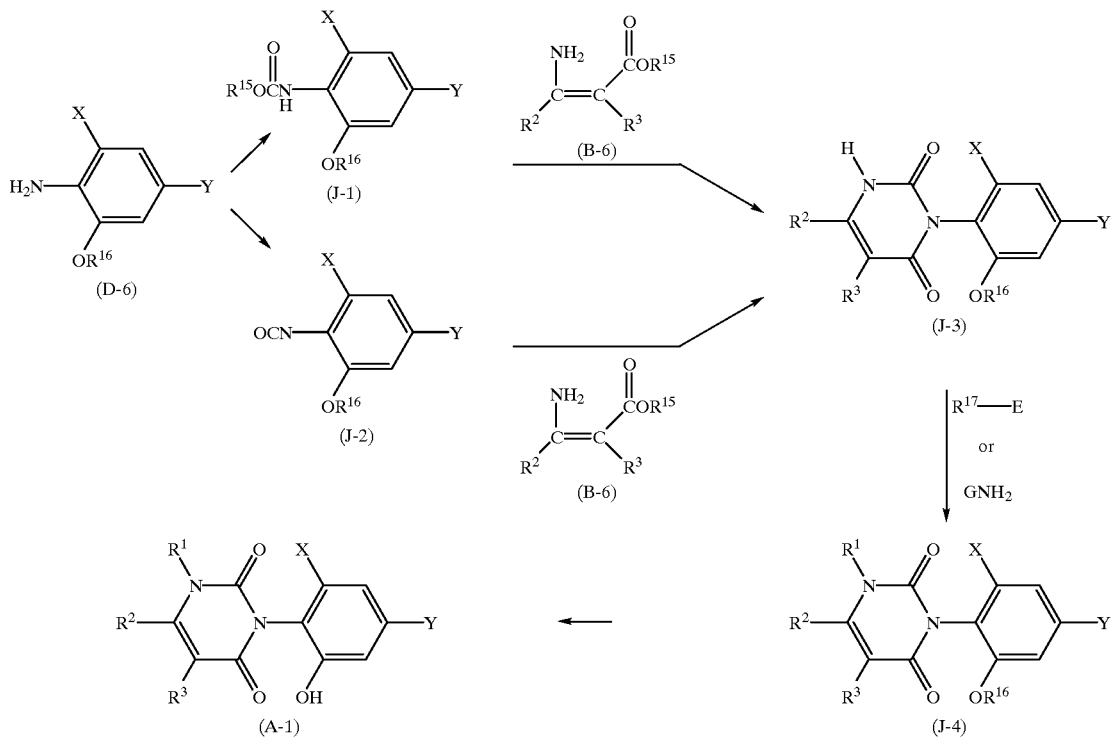

(In the formulae, each $R^1$, $R^2$, $R^3$, $R^{15}$, $R^{16}$, E, G, X and Y, is as defined above, and $R^{17}$ is an alkyl group or a haloalkyl group.)

The compound (J-1) or (J-2) is prepared from the compound (D-6) in accordance with the above Process 2, and then reacted with the compound (B-6) to obtain the compound (J-3). Further, in a case where $R^1$ is an alkyl group or a haloalkyl group, the compound (J-3) is reacted with a compound represented by the general formula $R^{17}$-E in the presence of a base, in accordance with the above Process 3, to obtain the compound (J-4), or in a case where $R^1$ is an amino group, the compound (J-3) is reacted with a compound represented by the general formula $G-NH_2$ in the presence of a base, in accordance with the above Process 4 to obtain the compound (J-4). The compound (J-4) is reacted with a dealkylating agent such as boron tribromide in a case where $R^{16}$ is an alkyl group, or it is hydrogenated under atmospheric pressure in a case where $R^{16}$ is a benzyl group which may be substituted, to obtain the compound (A-1).

Best Mode for Carrying out the Invention

Now, specific Preparation Examples will be described.

PREPARATION EXAMPLE 1

Preparation of 3-(4-chloro-6-fluoro-2-methylbenzofuran-7-yl)-1-methyl-6-trifluoromethyluracil (Compound No. 2)

100 ml of N,N-diethylaniline was added to 5.2 g (14 mmol) of 3-(4-chloro-2-fluoro-6-propargyloxyphenyl)-1-methyl-6-trifluoromethyluracil and 6.4 g (42 mmol) of cesium fluoride, followed by stirring at 180 to 190° C. for 3 hours. After completion of the reaction, the reaction solution was poured into water and extracted with ethyl acetate. The organic layer was washed sequentially with a 10% hydrochloric acid aqueous solution, water and a saturated sodium chloride aqueous solution and then dried over anhydrous magnesium sulfate. The solvent was distilled off under reduced pressure. Then, the obtained residue was purified by silica gel column chromatography to obtain 1.4 g (yield: 26.9%) of the desired product as white powder. Melting point: 196–197° C.

PREPARATION EXAMPLE 2

Preparation of 3-(4-chloro-2-methylbenzofuran-7-yl)-1-methyl-6-trifluoromethyluracil (Compound No. 196)

200 ml of N,N-diethylaniline was added to 20.0 g (55.8 mmol) of 3-(4-chloro-2-propargyloxyphenyl)-1-methyl-6-trifluoromethyluracil and 17.0 g (112 mmol) of cesium fluoride, followed by stirring at 180 to 190° C. for 2 hours. After completion of the reaction, the reaction solution was poured into water and extracted with ethyl acetate. The organic layer was washed sequentially with a 10% hydrochloric acid aqueous solution, water and a saturated sodium chloride aqueous solution and then dried over anhydrous magnesium sulfate. The solvent was distilled off under reduced pressure. Then, the obtained residue was purified by silica gel column chromatography to obtain 7.0 g (yield: 35.0%) of the desired product as white crystals. Melting point: 206–207° C.

PREPARATION EXAMPLE 3

Preparation of 3-(4-chloro-2,3-dimethylbenzofuran-7-yl)-1-methyl-6-trifluoromethyluracil (Compound No. 265)

2.0 g (6.2 mmol) of 3-(4-chloro-2-hydroxyphenyl)-1-methyl-6-trifluoromethyluracil and 1.3 g (7.5 mmol) of diethyl azodicarboxylate, were dissolved in 30 ml of tetrahydrofuran, and 20 ml of a tetrahydrofuran solution containing 2.0 g (7.6 mmol) of triphenylphosphine and 0.52 g (9.3 mmol) of 2-butyne-1-ol, was dropwise added thereto under cooling with ice. After completion of the dropwise addition, the mixture was stirred at room temperature for 30 minutes to obtain an ether compound. Then, 20 ml of N,N-diethylaniline was added to the purified ether compound and 0.94 g (6.2 mmol) of cesium fluoride, followed by heating at 190° C. for 15 hours. After completion of the reaction, the reaction mixture was purified by silica gel column chromatography to obtain 0.52 g (yield: 22.4%) of the desired product as white crystals. Melting point: 152–153° C.

PREPARATION EXAMPLE 4

Preparation of 3-(4,6-difluoro-2-methylbenzofuran-7-yl)-1-methyl-6-trifluoromethyluracil (Compound No. 375)

100 ml of N,N-diethylaniline was added to 4.7 g (13 mmol) of 3-(2,4-difluoro-6-propargyloxyphenyl)-1-methyl-6-trifluoromethyluracil and 5.9 g (39 mmol) of cesium fluoride, followed by stirring at 180 to 190° C. for 3 hours. After completion of the reaction, the reaction solution was poured into water and extracted with ethyl acetate. The organic layer was washed sequentially with a 10% hydrochloric acid aqueous solution, water and a saturated sodium chloride aqueous solution, and then dried over anhydrous magnesium sulfate. The solvent was distilled off under reduced pressure. Then, the obtained residue was purified by silica gel column chromatography to obtain 1.0 g (yield: 21.3%) of the desired product as white powder. Melting point: 176–178° C.

PREPARATION EXAMPLE 5

Preparation of 3-(4-chloro-2-ethylbenzofuran-7-yl)-1-methyl-6-trifluoromethyluracil (Compound No. 197)

50 ml of N,N-diethylaniline was added to 1.25 g (3.4 mmol) of 3-[4-chloro-2-(1-methyl-2-propynyloxy)phenyl]-1-methyl-6-trifluoromethyluracil and 1.0 g (6.8 mmol) of cesium fluoride, followed by stirring at 180 to 190° C. for 30 minutes. After completion of the reaction, the reaction mixture was purified directly by silica gel column chromatography to obtain 0.60 g (yield: 50.7%) of the desired product as white crystals. Melting point: 159–160° C.

PREPARATION EXAMPLE 6

Preparation of 3-(4-chloro-2-ethyl-6-fluorobenzofuran-7-yl)-6-trifluoromethyluracil (Compound No. 187)

80 ml of N,N-dimethylformamide was added to 5.8 g (32 mmol) of ethyl 3-amino-4,4,4-trifluorocrotonate and 6.6 g (43 mmol) of 1,8-diazabicyclo[5.4.0]-7-undecene, and 9.6 g (29 mmol) of 4-chloro-2-ethyl-6-fluoro-7-phenoxycarbonylaminobenzofuran was gradually added thereto at room temperature. After stirring at 60° C. for 8 hours, the reaction solution was poured into a 10% hydrochloric acid aqueous solution and acidified, and then extracted with ethyl acetate. The organic layer was washed sequentially with water and a saturated sodium chloride aqueous solution and then dried over anhydrous magnesium sulfate. The solvent was distilled off under reduced pressure.

Then, the obtained residue was purified by silica gel column chromatography to obtain 4.8 g (yield: 44%) of the desired product as white crystals. Melting point: 154–155° C.

PREPARATION EXAMPLE 7

Preparation of 3-(4-chloro-2-ethyl-6-fluorobenzofuran-7-yl)-1-methyl-6-trifluoromethyluracil (Compound No. 3)

0.50 g (1.3 mmol) of 3-(4-chloro-2-ethyl-6-fluorobenzofuran-7-yl)-6-trifluoromethyluracil and 0.30 g (2.3 mmol) of potassium carbonate, were suspended in 20 ml of N,N-dimethylformamide, and 0.23 g (1.6 mmol) of methyl iodide was dropwise added thereto under cooling with ice. After stirring at room temperature for 3 hours, the reaction solution was poured into water and extracted with ethyl acetate. The organic layer was washed sequentially with water and a saturated sodium chloride aqueous solution and then dried over anhydrous magnesium sulfate. The solvent was distilled off under reduced pressure. Then, the obtained residue was purified by silica gel column chromatography to obtain 0.48 g (yield: 92%) of the desired product as white crystals. Melting point: 142–143° C.

PREPARATION EXAMPLE 8

Preparation of 3-(4-chloro-2-ethyl-6-fluorobenzofuran-7-yl)-1-amino-6-trifluoromethyluracil (Compound No. 730)

80 ml of N,N-dimethylformamide was added to 3.4 g (9.0 mmol) of 3-(4-chloro-2-ethyl-6-fluorobenzofuran-7-yl)-6-trifluoromethyluracil, 2.7 g (14 mmol) of 2,4-dinitrophenoxyamine and 5.0 g (36 mmol) of potassium carbonate, followed by stirring at 60 to 70° C. for 1 hour. After completion of the reaction, the reaction solution was poured into water and extracted with ethyl acetate. The organic layer was washed sequentially with water and a saturated sodium chloride aqueous solution and then dried over anhydrous magnesium sulfate. The solvent was distilled off under reduced pressure. Then, the obtained residue was purified by silica gel column chromatography to obtain 2.0 g (yield: 58%) of the desired product as white crystals. Melting point: 145–147° C.

PREPARATION EXAMPLE 9

Preparation of 3-(2-bromomethyl-4-chloro-6-fluorobenzofuran-7-yl)-1-methyl-6-trifluoromethyluracil (A, Compound No. 8), 3-(4-chloro-2-dibromomethyl-6-fluorobenzofuran-7-yl)-1-methyl-6-trifluoromethyluracil (B, Compound No. 9) and 3-(4-chloro-6-fluoro-2-tribromomethylbenzofuran-7-yl)-1-methyl-6-trifluoromethyluracil (C, Compound No. 10)

400 ml of carbon tetrachloride was added to 20.0 g (53.1 mmol) of 3-(4-chloro-6-fluoro-2-methylbenzofuran-7-yl)-1-methyl-6-trifluoromethyluracil, 56.8 g (319.1 mmol) of N-bromosuccinimide, 0.2 g (1.4 mmol) of benzoyl peroxide and 0.2 g (1.2 mmol) of α, α'-azobisisobutyronitrile, followed by stirring for 24 hours under heating and refluxing. After completion of the reaction, the reaction solution was cooled, and precipitated crystals were filtered off. The filtrate was washed sequentially with an aqueous sodium hydrogensulfite, water and a saturated sodium chloride aqueous solution. After drying over anhydrous magnesium sulfate, the solvent was distilled off. The obtained residue was separated by silica gel column chromatography to obtain 5.0 g (yield: 20.6%) of (A) as white crystals, melting point: 168–172° C., 12.0 g (yield: 42.3%) of (B) as white crystals, melting point: 126–128° C. and 0.6 g (yield: 1.8%) of (C) as a dark brown viscous liquid, refractive index: unmeasurable, respectively. $^1$H-NMR of Compound No. 10 (solvent, CDCl$_3$): 3.61 (3H,bs), 6.42(1H,s), 7.26(1H,d)ppm.

PREPARATION EXAMPLE 10

Preparation of 3-(4-chloro-6-fluoro-2-formylbenzofuran-7-yl)-1-methyl-6-trifluoromethyluracil (Compound No. 33)

60 ml of concentrated sulfuric acid was added to 12.0 g (22.5 mmol) of 3-(4-chloro-2-dibromomethyl-6-fluorobenzofuran-7-yl)-1-methyl-6-trifluoromethyluracil, followed by stirring at 50° C. for 1 hour. After completion of the reaction, the reaction solution was poured into ice water and extracted with ethyl acetate. The organic layer was washed sequentially with a saturated sodium hydrogencarbonate aqueous solution, water and a saturated sodium chloride aqueous solution, and then dried over anhydrous sodium sulfate. The solvent was distilled off under reduced pressure. Then, the obtained residue was crystallized from isopropyl ether to obtain 7.6 g (yield: 88.4%) of the desired product as pale yellow crystals. Melting point: 180–183° C.

PREPARATION EXAMPLE 11

Preparation of 3-(2-carboxy-4-chloro-6-fluorobenzofuran-7-yl)-1-methyl-6-trifluoromethyluracil (Compound No. 42)

10 ml of concentrated sulfuric acid was added to 0.6 g (0.98 mmol) of 3-(4-chloro-6-fluoro-2-tribromomethylbenzofuran-7-yl)-1-methyl-6-trifluoromethyluracil, followed by stirring at 45° C. for 3 hours. After completion of the reaction, the reaction solution was poured into ice water and extracted with ethyl acetate. The organic layer was washed sequentially with water and a saturated sodium chloride aqueous solution, and then dried over anhydrous magnesium sulfate. The solvent was distilled off under reduced pressure. Then, the obtained residue was purified by silica gel column chromatography to obtain 0.21 g (yield: 53.7%) of the desired product as white crystals. Melting point: 267–268° C. (decomposed).

PREPARATION EXAMPLE 12

Preparation of 3-(2-carboxy-4-chloro-6-fluorobenzofuran-7-yl)-1-methyl-6-trifluoromethyluracil (Compound No. 42)

1.5 g (3.84 mmol) of 3-(4-chloro-6-fluoro-2-formylbenzofuran-7-yl)-1-methyl-6-trifluoromethyluracil was dissolved in 20 ml of acetone, and a Jones' reagent was dropwise added thereto at 5° C. until the orange color no longer disappeared. After completion of the reaction, the reaction solution was poured into water and extracted with ethyl acetate. The organic layer was washed sequentially with water and a saturated sodium chloride aqueous solution and then dried over anhydrous magnesium sulfate. The solvent was distilled off under reduced pressure. Then, the obtained residue was purified by silica gel column chromatography to obtain 1.2 g (yield: 76.9%) of the desired product as white crystals. Melting point: 267–268° C. (decomposed).

PREPARATION EXAMPLE 13

Preparation of 3-(4-chloro-6-fluorobenzofuran-7-yl)-1-methyl-6-trifluoromethyluracil (Compound No. 1)

7.0 g (17 mmol) of 3-(2-carboxy-4-chloro-6-fluorobenzofuran-7-yl)-1-methyl-6-trifluoromethyluracil and 5.0 g (79 mmol) of copper powder, were suspended in 50 ml of quinoline, followed by stirring at 200° C. for 1 hour. After completion of the reaction, the reaction solution was subjected to filtration. The filtrate was extracted with ethyl acetate. The organic layer was washed sequentially with a 10% hydrochloric acid aqueous solution and water and then dried over anhydrous sodium sulfate. The solvent was distilled off under reduced pressure. Then, the obtained residue was purified by silica gel column chromatography, to obtain 3.5 g (yield: 56%) of the desired product as white crystals. Melting point: 127–128° C.

PREPARATION EXAMPLE 14

Preparation of 3-(4-chloro-2-propionyl-6-fluorobenzofuran-7-yl)-1-methyl-6-trifluoromethyluracil (Compound No. 29)

1.3 g (1.4 mmol) of 3-(4-chloro-6-fluorobenzofuran-7-yl)-1-methyl-6-trifluoromethyluracil and 1.9 g (1.4 mmol) of aluminum chloride, were dissolved in 20 ml of nitromethane, and 0.5 g (1.4 mmol) of propionyl chloride was dropwise added thereto under cooling with ice. After completion of the dropwise addition, the mixture was stirred at room temperature for 12 hours. After completion of the reaction, the reaction solution was poured into a mixture of dilute hydrochloric acid and ice and extracted with ethyl acetate. The organic layer was washed sequentially with water and a saturated sodium chloride aqueous solution and then dried over anhydrous sodium sulfate. The solvent was distilled off under reduced pressure. Then, the obtained residue was purified by silica gel column chromatography to obtain 0.33 g (yield: 56%) of the desired product as a yellow glassy substance. Refractive index: unmeasurable, $^1$H-NMR (solvent, CDCl$_3$): 1.20(3H,m), 2.91(2H,q), 3.56(3H,s), 6.38 (1H,s), 7.28(1H,d), 7.58(1H,s)ppm

PREPARATION EXAMPLE 15

Preparation of 3-[4-chloro-6-fluoro-2-(1-methoxyiminoethyl) benzofuran-7-yl]-1-methyl-6-trifluoromethyluracil (Compound No. 37)

20 ml of methanol was added to 0.4 g (1 mmol) of 3-(2-acetyl-4-chloro-6-fluorobenzofuran-7-yl) -1-methyl-6-trifluoromethyluracil, 0.4 g (4 mmol) of potassium acetate and 0.33 g (4 mmol) of methoxyamine hydrochloride, followed by stirring at room temperature for 12 hours. After completion of the reaction, the solvent was distilled off under reduced pressure. The obtained residue was purified directly by silica gel column chromatography to obtain 0.28 g (yield: 64.6%) of the desired product as white powder. Melting point: 176–178° C.

PREPARATION EXAMPLE 16

Preparation of 3-(4-chloro- 2-methylhydrazonomethylbenzofuran-7-yl)-1-methyl-6-trifluoromethyluracil (Compound No. 231)

0.4 g (1.0 mmol) of 3-(4-chloro-2-formylbenzofuran-7-yl)-1-methyl-6-trifluoromethyluracil was dissolved in 5 ml of tetrahydrofuran, and 0.1 g (21.7 mmol) of monomethylhydrazine was added thereto under cooling with ice, followed by stirring at room temperature for 3 hours. After completion of the reaction, the reaction solution was poured into water and extracted with ethyl acetate. The organic layer was washed sequentially with water and a saturated sodium chloride aqueous solution and then dried over anhydrous sodium sulfate. The solvent was distilled off under reduced pressure. The obtained residue was purified by silica gel column chromatography to obtain 0.2 g (yield: 47.6%) of the desired product as a pale yellow glassy substance. Refractive index: unmeasurable, $^1$H-NMR (solvent, CDCl$_3$): 2.90(3H, s), 3.52(3H,s), 6.18(1H,bs), 6.40(1H,s), 6.85(1H,s), 7.05 (1H,d), 7.25(1H,s), 7.29(1H,d) ppm

PREPARATION EXAMPLE 17

Preparation of 3-[4-chloro-6-fluoro-2-(1-hydroxyethyl)benzofuran-7-yl]-1-methyl-6-trifluoromethyluracil (Compound No. 13)

4.0 g (10.2 mmol) of 3-(4-chloro-6-fluoro-2-formylbenzofuran-7-yl)-1-methyl-6-trifluoromethyluracil was dissolved in 20 ml of tetrahydrofuran, and 12.3 ml of methyl magnesium bromide (1.0M tetrahydrofuran solution) was dropwise added thereto at −65° C. After stirring at room temperature for 1 hour, the reaction solution was poured into water and extracted with ethyl acetate. The organic layer was washed sequentially with water and a saturated sodium chloride aqueous solution and then dried over anhydrous magnesium sulfate. The solvent was distilled off under reduced pressure. Then, the obtained residue was purified by silica gel column chromatography to obtain 2.3 g (yield: 55.3%) of the desired product as pale yellow crystals. Melting point: 154–157° C.

PREPARATION EXAMPLE 18

Preparation of 3-(2-acetyl-4-chloro-6-fluorobenzofuran-7-yl)-1-methyl-6-trifluoromethyluracil (Compound No. 28)

1.5 g (3.7 mmol) of 3-[4-chloro-6-fluoro-2-(1-hydroxyethyl) benzofuran-7-yl]-1-methyl-6-trifluoromethyluracil was dissolved in 20 ml of acetone, and a Jones' reagent was dropwise added thereto at 5° C. until the orange color no longer disappeared. After completion of the reaction, the reaction solution was poured into water and extracted with ethyl acetate. The organic layer was washed sequentially with water and a saturated sodium chloride aqueous solution and then dried over anhydrous magnesium sulfate. The solvent was distilled off under reduced pressure. Then, the obtained residue was purified by silica gel column chromatography to quantitatively obtain the desired product as pale orange crystals. Melting point: 193–194° C.

PREPARATION EXAMPLE 19

Preparation of 3-(4-chloro-6-fluoro-2-hydroxymethylbenzofuran-7-yl)-1-methyl-6-trifluoromethyluracil (Compound No. 12)

1.5 g (3.8 mmol) of 3-(4-chloro-6-fluoro-2-formylbenzofuran-7-yl)-1-methyl-6-trifluoromethyluracil was dissolved in 10 ml of tetrahydrofuran, and 4.5 ml of diisobutylaluminum hydride (0.94M hexane solution) was dropwise added thereto in a nitrogen stream at 5° C. After stirring at room temperature for 1 hour, the reaction solution was poured into water and extracted with ethyl acetate. The organic layer was washed sequentially with water and a saturated sodium chloride aqueous solution and then dried over anhydrous magnesium sulfate. The solvent was distilled off under reduced pressure. Then, the obtained residue was purified by silica gel column chromatography to obtain 1.4 g (yield: 90.7%) of the desired product as pale yellow crystals. Melting point: 198–199° C.

PREPARATION EXAMPLE 20

Preparation of 3-[4-chloro-2-(1-chloroethyl)-6-fluorobenzofuran-7-yl]-1-methyl-6-trifluoromethyluracil (Compound No. 393)

0.50 g (1.2 mmol) of 3-[4-chloro-2-(1-hydroxyethyl)-6-fluorobenzofuran-7-yl]-1-methyl-6-trifluoromethyluracil and 0.64 g (2.5 mmol) of triphenylphosphine were dissolved in 20 ml of acetonitrile, and 0.60 g (2.5 mmol) of chloranil was added thereto at room temperature. After stirring at room temperature for 2 hours, the reaction solution was poured into water and extracted with ethyl acetate. The organic layer was washed sequentially with water and a 5% potassium carbonate aqueous solution and then dried over anhydrous sodium sulfate. The solvent was distilled off under reduced pressure. Then, the obtained residue was purified by silica gel column chromatography to obtain 0.50 g (yield: 96.2%) of the desired product as a pale brown glassy substance. Refractive index: 1.5639 (20° C.).

PREPARATION EXAMPLE 21

Preparation of 3-(4-chloro-6-fluoro-2-methoxymethylbenzofuran-7-yl)-1-methyl-6-trifluoromethyluracil (Compound No. 14)

1.5 g (3.3 mmol) of 3-(2-bromomethyl-4-chloro-6-fluorobenzofuran-7-yl)-1-methyl-6-trifluoromethyluracil was dissolved in 30 ml of tetrahydrofuran, and 0.7 g (3.6 mmol) of sodium methoxide (28% methanol solution) was dropwise added thereto under cooling with ice. After stirring at room temperature for 5 minutes, the reaction solution was poured into water and extracted with ethyl acetate. The organic layer was washed sequentially with water and a saturated sodium chloride aqueous solution and then dried over anhydrous magnesium sulfate. The solvent was distilled off under reduced pressure. Then, the obtained residue was purified by silica gel column chromatography to obtain 0.75 g (yield: 56.0%) of the desired product as a yellowish brown glassy substance. Refractive index: 1.5389 (20° C.).

PREPARATION EXAMPLE 22

Preparation of 3-(4-chloro-2-ethylthiomethyl-6-fluorobenzofuran-7-yl)-1-methyl-6-trifluoromethyluracil (Compound No. 22)

1.5 g (3.3 mmol) of 3-(2-bromomethyl-4-chloro-6-fluorobenzofuran-7-yl)-1-methyl-6-trifluoromethyluracil and 0.7 g (5.1 mmol) of potassium carbonate were suspended in 20 ml of N,N-dimethylformamide, and 0.21 g (3.4 mmol) of ethylmercaptan was added thereto at room temperature, followed by stirring at room temperature for 1 hour. After completion of the reaction, the reaction solution was poured into water and extracted with ethyl acetate. The organic layer was washed sequentially with water and a saturated sodium chloride aqueous solution, and then dried over anhydrous magnesium sulfate. The solvent was distilled off under reduced pressure. Then, the obtained residue was purified by silica gel column chromatography to obtain 1.2 g (yield: 83.4%) of the desired product as a yellowish brown glassy substance. Refractive index: 1.5629 (20° C.).

PREPARATION EXAMPLE 23

Preparation of 3-(4-chloro-6-fluoro-2-methylsulfonylmethylbenzofuran-7-yl)-1-methyl-6-trifluoromethyluracil (Compound No. 21)

0.5 g (1.2 mmol) of 3-(4-chloro-6-fluoro-2-methylthiomethylbenzofuran-7-yl)-1-methyl-6- trifluoromethyluracil and 0.6 g (3.5 mmol) of metachloroperbenzoic acid were suspended in chloroform, followed by stirring at room temperature for 1 hour. After completion of the reaction, ethyl acetate was added to the reaction solution, and the mixture was washed sequentially with water and a 10% sodium hydrogensulfite aqueous solution. Then, the organic layer was dried over anhydrous sodium sulfate. The solvent was distilled off under reduced pressure. Then, the obtained residue was purified by silica gel column chromatography to obtain 0.5 g (yield: 92.9%) of the desired product as white crystals. Melting point: 209–211° C.

PREPARATION EXAMPLE 24

Preparation of 3-(4-chloro-6-fluoro-2-methoxycarbonylbenzofuran-7-yl)-1-methyl-6-trifluoromethyluracil (Compound No. 43)

0.21 g (0.5 mmol) of 3-(2-carboxy-4-chloro-6-fluorobenzofuran-7-yl)-1-methyl-6-trifluoromethyluracil and 0.16 g (1.1 mmol) of potassium carbonate were suspended in 10 ml of N,N-dimethylformamide, and 0.15 g (1.1 mmol) of methyl iodide was added thereto at room temperature, followed by stirring at room temperature for 3 hours. After completion of the reaction, the reaction solution was poured into water and extracted with ethyl acetate. The organic layer was washed sequentially with water and a saturated sodium chloride aqueous solution, and then dried over anhydrous magnesium sulfate. The solvent was distilled off under reduced pressure. Then, the obtained residue was purified by silica gel column chromatography to obtain 0.21 g (yield: 96.8%) of the desired product as yellowish brown crystals. Melting point: 194–196° C.

PREPARATION EXAMPLE 25

Preparation of 3-(4-chloro-2-ethylcarbamoylbenzofuran-7-yl)-1-methyl-6-trifluoromethyluracil (Compound No. 248)

10 ml of thionyl chloride was added to 0.37 g (0.96 mmol) of 3-(2-carboxy-4-chlorobenzofuran-7-yl)-1-methyl-6-trifluoromethyluracil, followed by stirring for 3 hours under heating and refluxing. After completion of the reaction, thionyl chloride was distilled off under reduced pressure. The obtained residue was dissolved in 20 ml of tetrahydrofuran. To this solution, 0.24 g (3.84 mmol) of ethylamine (70% aqueous solution) was added, followed by stirring for 10 minutes at room temperature. After completion of the reaction, the reaction solution was poured into water, and precipitated crystals were collected by filtration to obtain 0.31 g (yield: 78.3%) of the desired product as white crystals. Melting point: 225–226° C.

PREPARATION EXAMPLE 26

Preparation of 3-(2-acetoxymethyl-4-chlorobenzofuran-7-yl)-1-methyl-6-trifluoromethyluracil (Compound No. 210)

0.4 g (1.1 mmol) of 3-(4-chloro-2-hydroxymethylbenzofuran-7-yl)-1-methyl-6-trifluoromethyluracil and 0.13 g (1.2 mmol) of triethylamine were dissolved in 20 ml of tetrahydrofuran, and 0.1 g (1.2 mmol) of acetyl chloride was dropwise added thereto under cooling with ice. After completion of the reaction, the reaction solution was poured into water and washed with ethyl acetate. The organic layer was washed sequentially with a 10% hydrochloric acid aqueous solution, water and a saturated sodium chloride aqueous solution, and then, dried over anhydrous magnesium sulfate. The solvent was distilled off under reduced pressure. Then, the obtained residue was purified by silica gel column chromatography to obtain 0.2 g (yield: 45.5%) of the desired product as white solid. Melting point: 135–138° C.

PREPARATION EXAMPLE 27

Preparation of 3-[4-chloro-6-fluoro-2-(1-dimethylaminoethyl)benzofuran-7-yl]-1-methyl-6-trifluoromethyluracil (Compound No. 572)

0.5 g (1.2 mmol) of 3-[4-chloro-6-fluoro-2-(1-methylaminoethyl)benzofuran-7-yl]-1-methyl-6-trifluoromethyluracil and 0.40 g (2.9 mmol) of potassium carbonate were suspended in 50 ml of N,N-dimethylformamide, and 1.0 g (7.0 mmol) of methyl iodide was added thereto, followed by stirring at 60° C. for 2 hours. After completion of the reaction, the reaction solution was poured into water and extracted with ethyl acetate. The organic layer was washed sequentially with water and a saturated sodium chloride aqueous solution and then dried over anhydrous magnesium sulfate. The solvent was distilled off under reduced pressure. Then, the obtained residue was purified by silica gel column chromatography to obtain 0.35 g (yield: 68%) of the desired product as a purple glassy substance. Refractive index: 1.5341 (20° C.)

PREPARATION EXAMPLE 28

Preparation of 3-(3-acetyl-4-chloro-6-fluoro-2-methylbenzofuran-7-yl)-1-methyl-6-trifluoromethyluracil (Compound No. 101)

1.6 g (4.2 mmol) of 3-(4-chloro-6-fluoro-2-methylbenzofuran-7-yl)-1-methyl-6-trifluoromethyluracil was dissolved in 50 ml of nitromethane, and 5.6 g (42 mmol) of aluminum chloride was added thereto at room temperature. Further, 3.3 g (42 mmol) of acetyl chloride was dropwise added thereto. After completion of the dropwise addition, stirring was carried out for 5 hours under heating and ref refluxing. After completion of the reaction, the reaction solution was poured into a mixture of dilute hydrochloric acid and ice and extracted with ethyl acetate. The organic layer was washed sequentially with water and a saturated sodium chloride aqueous solution and then, dried over anhydrous sodium sulfate. The solvent was distilled off under reduced pressure. Then, the obtained residue was purified by silica gel column chromatography to obtain 1.2 g (yield: 66.7%) of the desired product as pale yellow crystals. Melting point: 138–140° C.

PREPARATION EXAMPLE 29

Preparation of 3-(4-chloro-6-fluoro-3-formyl-2-methylbenzofuran-7-yl)-1-methyl-6-trifluoromethyluracil (Compound No. 91)

2.0 g (53 mmol) of 3-(4-chloro-6-fluoro-2-methylbenzofuran-7-yl)-1-methyl-6-trifluoromethyluracil and 36.5 g (0.32 mol) of dichloromethyl methyl ether were dissolved in 100 ml of dichloromethane, and 200 ml (0.20 mol) of tin tetrachloride (1M dichloromethane solution) was dropwise added thereto at 0° C. After completion of the dropwise addition, stirring was carried out at room temperature for 2 hours. After completion of the reaction, the reaction solution was poured into a mixture of dilute hydrochloric acid and ice and extracted with dichloromethane.

The organic layer was washed with water and then dried over anhydrous sodium sulfate. The solvent was distilled off under reduced pressure. Then, the obtained residue was purified by silica gel column chromatography to obtain 19.5 g (yield: 90.7%) of the desired product as white crystals. Melting point: 148–150° C.

PREPARATION EXAMPLE 30

Preparation of 3-[4-chloro-6-fluoro-3-(1-methoxyiminoethyl)-2-methylbenzofuran-7-yl]-1-methyl-6-trifluoromethyluracil (Compound No. 111)

50 ml of methanol was added to 0.4 g (1 mmol) of 3-(3-acetyl-4-chloro-6-fluoro-2-methylbenzofuran-7-yl)-1-methyl-6-trifluoromethyluracil, 0.5 g (5 mmol) of potassium acetate and 0.5 g (6 mmol) of methoxyamine hydrochloride, followed by stirring at room temperature for 12 hours and further for 8 hours under heating and refluxing. After completion of the reaction, methanol was distilled off under reduced pressure, ethyl acetate was added to the obtained residue, and the mixture was washed sequentially with water and a saturated sodium chloride aqueous solution. The organic layer was dried over anhydrous sodium sulfate. Then, the solvent was distilled off under reduced pressure. The obtained residue was purified by silica gel column chromatography to obtain 0.4 g (yield: 100%) of the desired product as pale yellow crystals. Melting point: 65–67° C., $^1$H-NMR (solvent: $CDCl_3$): 1.54 (1H,s), 2.21(3H,s), 2.35 (3H,s), 3.59(3H,s), 3.91(3H,s), 6.41(1H,s), 7.16(1H,d)ppm

PREPARATION EXAMPLE 31

Preparation of 3-(4-chloro-6-fluoro-2-methyl-3-thioacetylbenzofuran-7-yl)-1-methyl-6-trifluoromethyluracil (Compound No. 631)

100 ml of toluene was added to 0.50 g (1.2 mmol) of 3-(3-acetyl-4-chloro-6-fluoro-2-methylbenzofuran-7-yl)-1-methyl-6-trifluoromethyluracil and 1.5 g (6.7 mmol) of phosphorus pentasulfide, followed by stirring for 2 hours under heating and refluxing. After completion of the reaction, 100 ml of toluene was further added to the reaction solution. The organic layer was washed sequentially with water and a saturated sodium chloride aqueous solution and then dried over anhydrous magnesium sulfate. The solvent was distilled off under reduced pressure. Then, the obtained residue was purified by silica gel column chromatography to obtain 47 mg (yield: 9%) of the desired product as an orange colored glassy substance. Refractive index: 1.5967 (20° C.).

PREPARATION EXAMPLE 32

Preparation of 3-(3-bromo-4-chloro-2-methylbenzofuran-7-yl)-1-methyl-6-trifluoromethyluracil (Compound No. 272)

1.0 g (2.8 mmol) of 3-(4-chloro-2-methylbenzofuran-7-yl)-1-methyl-6-trifluoromethyluracil was dissolved in 30 ml of acetic acid, and 0.9 g (5.6 mmol) of bromine was dropwise added thereto at room temperature. After completion of the dropwise addition, stirring was carried out at 40° C. for 6 hours. After completion of the reaction, the reaction solution was poured into water and extracted with ethyl acetate. The organic layer was washed sequentially with water and 10% aqueous ammonia and then dried over anhydrous sodium sulfate. The solvent was distilled off under reduced pressure. Then, the obtained residue was purified by silica gel column chromatography to obtain 0.6 g (yield: 50.0%) of a pale yellow glassy substance. Refractive index: 1.5632 (20° C.).

PREPARATION EXAMPLE 33

Preparation of 3-(4-chloro-2-methyl-3-nitrobenzofuran-7-yl)-1-methyl-6-trifluoromethyluracil (Compound No. 303)

0.5 g (1.4 mmol) of 3-(4-chloro-2-methylbenzofuran-7-yl)-1-methyl-6-trifluoromethyluracil was dissolved in 10 ml of concentrated sulfuric acid, and 0.1 g (1.1 mmol) of 60% nitric acid was dropwise added thereto at −20° C. After stirring at −20° C. for 10 minutes, the reaction solution was poured into ice water and extracted with 50 ml of chloroform. The organic layer was washed sequentially with water and a saturated sodium chloride aqueous solution and then dried over anhydrous magnesium sulfate. The solvent was distilled off under reduced pressure. Then, the obtained residue was purified by silica gel column chromatography to obtain 0.3 g (yield: 53.3%) of the desired product as a pale yellow crystals. Melting point: 174–175° C.

PREPARATION EXAMPLE 34

Preparation of 3-[4-chloro-2-(1-cyanoethyl)-3-ethoxycarbonyl-6-fluorobenzofuran-7-yl)-1-methyl-6-trifluoromethyluracil (Compound No. 671)

20 ml of N,N-dimethylformamide was added to 0.8 g (1.6 mmol) of 3-[4-chloro-2-(1-chloroethyl)-3-ethoxycarbonyl-6-fluorobenzofuran-7-yl]-1-methyl-6-trifluoromethyluracil, 0.16 g (2.5 mmol) of potassium cyanide and 0.40 g (2.9 mmol) of potassium carbonate, followed by stirring at room temperature for 3 hours. After completion of the reaction, the reaction solution was poured into water and extracted with ethyl acetate. The organic layer was washed sequentially with water and a saturated sodium chloride aqueous solution and then, dried over anhydrous magnesium sulfate. The solvent was distilled off under reduced pressure. Then, the obtained residue was purified by silica gel column chromatography to obtain 0.58 g (yield: 74%) of the desired product as a yellow glassy substance. Refractive index: 1.5348 (20° C.).

PREPARATION EXAMPLE 35

Preparation of 3-(3-carbamoylmethyl-4-chloro-6-fluoro-2-methylbenzofuran-7-yl)-1-methyl-6-trifluoromethyluracil (Compound No. 619)

0.50 g (1.2 mmol) of 3-(4-chloro-3-cyanomethyl-6-fluoro-2-methylbenzofuran-7-yl)-1-methyl-6-trifluoromethyluracil was dissolved in 30 ml of 50% sulfuric acid, followed by stirring at 60° C. for 2 hours. After completion of the reaction, the reaction solution was poured into water and extracted with ethyl acetate. The organic layer was washed sequentially with water and a saturated sodium chloride aqueous solution and then, dried over anhydrous magnesium sulfate. The solvent was distilled off under reduced pressure. Then, the obtained residue was purified by silica gel column chromatography to obtain 0.39 g (yield: 75%) of the desired product as white crystals. Melting point: 127–129° C.

PREPARATION EXAMPLE 36

Preparation of 3-[4-chloro-6-fluoro-2-(1-thiocyanate ethyl)benzofuran-7-yl]-1-methyl-6-trifluoromethyluracil (Compound No. 577)

30 ml of ethanol was added to 2.3 g (4.9 mmol) of 3-[2-(1-bromoethyl)-4-chloro-6-fluorobenzofuran-7-yl)-1- methyl-6-trifluoromethyluracil and 1.5 g (2.3 mmol) of potassium thiocyanate, followed by stirring at 60° C. for 2 hours. After completion of the reaction, the reaction solution was poured into water and extracted with ethyl acetate. The organic layer was washed sequentially with water and a saturated sodium chloride aqueous solution and then, dried over anhydrous magnesium sulfate. The solvent was distilled off under reduced pressure. Then, obtained residue was purified by silica gel column chromatography to obtain 1.1 g (yield: 50%) of the desired product as yellow crystals. Melting point: 60–63° C., $^1$H-NMR (solvent: CDCl$_3$): 1.93 (3H,d), 3.59(3H,s), 4.56(1H,q), 6.40(1H,d), 6.87(1H,s), 7.25 (1H,s)ppm

PREPARATION EXAMPLE 37

Preparation of 3-(4-chloro-6-fluoro-2-vinylbenzofuran- 7-yl)-1-methyl-6-trifluoromethyluracil (Compound No. 412)

50 ml of dioxane and 0.5 ml of water were added to 1.0 g (2.6 mmol) of 3-(4-chloro-6-fluoro-2-formylbenzofuran-7-yl)-1-methyl-6-trifluoromethyluracil, 0.94 g (2.6 mmol) of methyltriphenylphosphonium bromide and 0.43 g (3.1 mmol) of potassium carbonate, followed by stirring for 2 hours under heating and refluxing. After completion of the reaction, the reaction solution was poured into water and adjusted to pH 3 with an aqueous citric acid solution and then, extracted with ethyl acetate. The organic layer was washed sequentially with water and a saturated sodium chloride aqueous solution and then, dried over anhydrous magnesium sulfate. The solvent was distilled off under reduced pressure. Then, the obtained residue was purified by silica gel column chromatography to obtain 0.51 g (yield: 51%) of the desired product as yellow crystals. Melting point: 108–109° C.

PREPARATION EXAMPLE 38

Preparation of 3-[4-chloro-2-(2-oxiranyl)-6-fluorobenzofuran-7-yl]-1-methyl-6-trifluoromethyluracil (Compound No. 606)

50 ml of chloroform was added to 0.4 g (1.0 mmol) of 3-(4-chloro-6-fluoro-2-vinylbenzofuran-7-yl)-1-methyl-6-trifluoromethyluracil, and 10 ml of a chloroform solution containing 0.21 g (1.0 mmol) of 80% metachloroperbenzoic acid, was dropwise added thereto at room temperature. After stirring at room temperature for 12 hours, the reaction solution was poured into water and extracted with chloroform. The organic layer was washed sequentially with water, a 10% sodium hydrogensulfite aqueous solution and a saturated sodium chloride aqueous solution and then, dried over anhydrous magnesium sulfate. The solvent was distilled off under reduced pressure. Then, the obtained residue was purified by silica gel column chromatography to obtain 85 mg (yield: 21%) of the desired product as white crystals. Melting point: 109–111° C.

PREPARATION EXAMPLE 39

Preparation of 3-(4-chloro-6-fluoro-3-methoxy-2-methylbenzofuran-7-yl)-1-methyl-6-trifluoromethyluracil (Compound No. 427)

0.50 g (1.3 mmol) of 3-(4-chloro-6-fluoro-3-hdyroxy-2-methylbenzofuran-7-yl)-1-methyl-6-trifluoromethyluracil and 2.0 g (1.3 mmol) of cesium fluoride were suspended in 10 ml of N,N-dimethylformamide, and 0.3 g (2.1 mmol) of methyl iodide was added thereto, followed by stirring at 70° C. for 1 hour. After completion of the reaction, ethyl acetate was added to the reaction solution. The organic layer was washed with water and then dried over anhydrous sodium sulfate. The solvent was distilled off under reduced pressure. Then, the obtained residue was purified by silica gel column chromatography to obtain 0.19 g (yield: 35%) of the desired product as white crystals. Melting point: 57–60° C.

PREPARATION EXAMPLE 40

Preparation of 3-(4-chloro-3-hydroxyamino-2-methylbenzofuran-7-yl)-1-methyl-6-trifluoromethyluracil (Compound No. 305)

5 ml of acetic acid, 200 ml of ethyl acetate and 100 ml of water were added to 2.3 g (5.7 mmol) of 3-(4-chloro-2-methyl-3-nitrobenzofuran-7-yl)-1-methyl-6-trifluoromethyluracil and 1.6 g (28 mmol) of iron powder, followed by stirring for 2 hours under heating and refluxing. After completion of the reaction, insoluble matters were filtered off. The organic layer was washed sequentially with water and a sodium chloride aqueous solution and then, dried over anhydrous magnesium sulfate. The solvent was distilled off under reduced pressure. Then, the obtained residue was purified by silica gel column chromatography to obtain 1.2 g (yield: 54%) of the desired product as pale yellow crystals. Melting point: 134–136° C.

REFERENCE EXAMPLE 1

Preparation of 3-(4-chloro-2-fluoro-6-hydroxyphenyl)-1-methyl-6-trifluoromethyluracil 5.7 g (16 mmol) of 3-(4-chloro-2-fluoro-6-methoxyphenyl)-1-methyl-6-trifluoromethyluracil was dissolved in 100 ml of dichloromethane, and 27 ml (80 mmol) of boron tribromide (3.0M dichloromethane solution) was dropwise added at 0° C. After stirring at room temperature for 3 hours, the reaction solution was poured into ice water and neutralized with sodium hydrogencarbonate. It was extracted with dichloromethane. The organic layer was washed sequentially with water and a saturated sodium chloride aqueous solution and then dried over anhydrous magnesium sulfate. The solvent was distilled off under reduced pressure. Then, the obtained crude crystals were washed with isopropyl ether to obtain 5.4 g (yield: 98.2%) of the desired product as white crystals. Melting point: 143–144° C.

REFERENCE EXAMPLE 2

Preparation of 3-(4-chloro-2-fluoro-6-propargyloxyphenyl)-1-methyl-6-trifluoromethyluracil 5.4 g (16 mmol) of 3-(4-chloro-2-fluoro-6-hydroxyphenyl)-1-methyl-6-trifluoromethyluracil and 3.3 g (24 mmol) of potassium carbonate were suspended in 50 ml of N,N-dimethylformamide, and 2.7 g (22 mmol) of propargyl bromide was dropwise added at room temperature. After stirring at from 60 to 70° C. for 5 hours, the reaction solution was poured into water and extracted with ethyl acetate. The organic layer was washed sequentially with water and a saturated sodium chloride aqueous solution and then dried over anhydrous magnesium sulfate. The solvent was distilled off under reduced pressure. Then, the obtained crude crystals were washed with isopropyl ether to obtain 5.2 g (yield: 86.7%) of the desired product as white crystals. Melting point: 150–152° C.

REFERENCE EXAMPLE 3

Preparation of 3-(4-chloro-2-hydroxyphenyl)-1-methyl-6-trifluoromethyluracil 41.0 g (122.5 mmol) of 3-(4-chloro-2-methoxyphenyl)-1-methyl-6-trifluoromethyluracil was dissolved in 1000 ml of dichloromethane, and 470 ml (470.8 mmol) of boron tribromide (1.0M dichloromethane solution) was dropwise added at from −10° C. to −5° C. After stirring at room temperature for 3 hours, the reaction solution was poured into ice water and neutralized with sodium hydrogencarbonate. It was extracted with dichloromethane. The organic layer was washed sequentially with water and a saturated sodium chloride aqueous solution and then, dried over anhydrous magnesium sulfate. The solvent was distilled off under reduced pressure. Then, the obtained crude crystals were washed with isopropyl ether to obtain 27.6 g (yield: 70.3%) of the desired product as white crystals. Melting point: 198–202° C.

REFERENCE EXAMPLE 4

Preparation of 3-(4-chloro-2-propargyloxyphenyl)-1-methyl-6-trifluoromethyluracil 22.6 g (70.5 mmol) of 3-(4-chloro-2-hydroxyphenyl-1-methyl-6-trifluoromethyluracil and 14.5 g (105.1 mmol) of potassium carbonate were suspended in 150 ml of N,N-dimethylformamide, and 11.2 g (94.1 mmol) of propargyl bromide was dropwise added thereto at room temperature. After stirring at 70° C. for 2 hours, the reaction solution was poured into water and extracted with ethyl acetate. The organic layer was washed sequentially with water and a saturated sodium chloride aqueous solution and then, dried over anhydrous magnesium sulfate. The solvent was distilled off under reduced pressure. Then, the obtained crude crystals were washed with isopropyl ether to obtain 22.5 g (yield: 89.0%) of the desired product as pale brown powder. Melting point: 147–148° C.

REFERENCE EXAMPLE 5

Preparation of 3-(2,4-difluoro-6-hydroxyphenyl)-1-methyl-6-trifluoromethyluracil 13.6 g (40 mmol) of 3-(2,4-difluoro-6-methoxyphenyl)-1-methyl-6-trifluoromethyluracil was dissolved in 150 ml of dichloromethane, and 66.7 ml (200 mmol) of boron tribromide (3.0M dichloromethane solution) was dropwise added thereto at 0° C. After stirring at room temperature for 3 hours, the reaction solution was poured into ice water and neutralized with sodium hydrogencarbonate. It was extracted with dichloromethane. The organic layer was washed sequentially with water and a saturated sodium chloride aqueous solution and then, dried over anhydrous magnesium sulfate. The solvent was distilled off under reduced pressure. Then, the obtained crude crystals were washed with isopropyl ether to obtain 9.8 g (yield: 75.4%) of the desired product as white crystals. Melting point: 195–196° C.

REFERENCE EXAMPLE 6

Preparation of 3-(2,4-difluoro-6-propargyloxyphenyl)-1-methyl-6-trifluoromethyluracil 4.8 g (15 mmol) of 3-(2,4-difluoro-6-hydroxyphenyl)-1-methyl-6-trifluoromethyluracil and 3.2 g (23 mmol) of potassium carbonate were suspended in 50 ml of N,N-dimethylformamide, and 2.5 g (21 mmol) of propargyl bromide was dropwise added thereto at room temperature. After stirring at from 60 to 70° C. for 5 hours, the reaction solution was poured into water and extracted with ethyl acetate. The organic layer was washed sequentially with water and a saturated sodium chloride aqueous solution and then, dried over anhydrous magnesium sulfate. The solvent was distilled off under reduced pressure. Then, the obtained crude crystals were washed with isopropyl ether to obtain 5.0 g (yield: 92.63%) of the desired product as yellowish brown powder. Melting point: 159–162° C.

REFERENCE EXAMPLE 7

Preparation of 3-[4-chloro-2-(1-methyl-2-propynyloxy) phenyl]-1-methyl-6-trifluoromethyluracil 1.7 g (5.3 mmol) of 3-(4-chloro-2-hydroxyphenyl)-1-methyl-6-trifluoromethyluracil, 0.63 g (9.0 mmol) of 1-butyn-3-ol and 1.57 g (6.0 mmol) of triphenylphosphine were dissolved in 100 ml of tetrahydrofuran, and 1.0 g (6.0 mmol) of diethyl azodicarboxylate was dropwise added thereto under cooling with ice. After stirring at room temperature for 1 hour, the solvent was distilled off. Then, the obtained residue was purified by silica gel column chromatography to obtain 1.86 g (yield: 93.9%) of the desired product as white crystals. Melting point: 96–99° C.

Now, with respect of some of the compounds of the present invention, $^{1}$H-NMR data will be shown below.

TABLE 25

| Comp. Nos. | $^{1}$H-NMR δ value (ppm) Solvent CDCl$_3$ |
|---|---|
| 10 | 3.61(3H, bs) 6.42(1H, s) 7.26(1H, d) |
| 20 | 2.11(3H, s) 3.59(3H, s) 3.73(2H, s) 6.40(1H, s) 6.70(1H, s) 7.19(1H, d) |
| 29 | 1.20(3H, m) 2.91(2H, q) 3.56(3H, s) 6.38(1H, s) 7.28(1H, d) 7.58(1H, s) |
| 30 | 1.01(3H, t) 1.78(2H, m) 2.87(2H, t) 3.59(3H, s) 6.41(1H, s) 7.36(1H, d) 7.57(1H, s) |
| 35 | 3.60(3H, s) 4.02(3H, s) 6.42(1H, s) 7.07(1H, s) 7.24(1H, d) 8.00(1H, s) |
| 45 | 1.37(6H, d) 3.57(3H, s) 5.26(1H, m) 6.39(1H, s) 7.29(1H, d) 7.56(1H, s) |
| 79 | 2.29(1H, bs) 2.40(3H, s) 3.57(3H, s) 4.78(1H, s) 6.38(1H, s) 7.17(1H, d) |
| 80 | 2.05(3H, s) 2.43(3H, s) 3.57(3H, s) 5.27(2H, s) 6.35(1H, s) 7.15(1H, d) |
| 86 | 2.69(3H, s) 3.60(3H, s) 6.43(1H, s) 7.29(1H, d) 8.00(1H, bs) |
| 89 | 1.38(6H, d) 2.58(3H, s) 3.55(3H, s) 5.26(1H, m) 6.35(1H, s) 7.20(1H, d) |
| 111 | 1.54(1H, s) 2.21(3H, s) 2.35(3H, s) 3.59(3H, s) 3.91(3H, s) 6.41(1H, s) 7.16(1H, d) |
| 119 | 2.73(3H, s) 3.57(3H, s) 6.37(1H, s) 7.32(1H, d) |
| 141 | 1.30(3H, s) 3.16(2H, q) 3.61(3H, s) 6.42(1H, s) 7.31(1H, d) 10.73(1H, s) |
| 207 | 1.60(3H, d) 2.59(1H, m) 3.57(3H, s) 4.97(1H, m) 6.40(1H, s) 6.78(1H, s) 7.09(1H, d) 7.32(1H, d) |

TABLE 26

| Comp. Nos. | $^{1}$H-NMR δ value (ppm) Solvent CDCl$_3$ |
|---|---|
| 231 | 2.90(3H, s) 3.52(3H, s) 6.18(1H, bs) 6.40(1H, s) 6.85(1H, s) 7.05(1H, d) 7.25(1H, s) 7.29(1H, d) |
| 247 | 3.17(6H, dd) 3.57(3H, s) 6.39(1H, s) 7.25(1H, d) 7.39(1H, d) |
| 270 | 2.33(3H, s) 3.60(3H, bs) 6.40(1H, s) 7.0~7.5(7H, m) |

TABLE 26-continued

| Comp. Nos. | ¹H-NMR δ value (ppm) Solvent CDCl₃ |
|---|---|
| 334 | 1.23(6H, d) 3.43(1H, m) 3.57(3H, s) 6.37(1H, s) 7.18(1H, d) |
| 376 | 2.67(3H, s) 3.60(3H, s) 6.36(1H, s) 7.21(1H, d) 7.38(1H, d) |
| 401 | 0.97(3H, m) 1.92(2H, m) 2.34(1H, m) 3.57(3H, s) 4.66(1H, m) 6.37(1H, s) 6.72(1H, s) 7.19(1H, d) |
| 446 | 0.99(3H, t) 1.20(3H, d) 1.68(2H, m) 2.67(2H, t) 3.31(1H, m) 3.60(3H, s) 6.41(1H, s) 7.22(1H, d) |
| 460 | 1.16(3H, t) 1.30(3H, t) 2.89(2H, q) 3.29(2H, q) 3.61(3H, s) 6.42(1H, s) 7.24(1H, d) |
| 463 | 0.88(3H, m) 1.24(3H, t) 1.93(2H, m) 2.57, 2.73(1H, d) 2.81(2H, m) 3.52, 3.55(3H, s) 4.67(1H, m) 6.30, 6.36(1H, s) 7.15(1H, d) |
| 464 | 0.94(3H, t) 1.27(3H, t) 1.0~2.0(4H, m) 2.17(1H, m) 2.86(2H, m) 3.54, 3.57(3H, s) 4.79(1H, m) 6.35, 6.38(1H, s) 7.15(1H, d) |
| 471 | 1.33(3H, t) 1.74~1.78(3H, m) 2.48~2.74(2H, m) 3.60(3H, s) 3.99~4.13(1H, m) 6.40(1H, d) 6.82(1H, s) 7.24(1H, dd) |
| 472 | 1.30(3H, t) 1.80(3H, m) 3.0(2H, m) 3.55(3H, s) 4.40(1H, q) 6.45(1H, d) 7.00(1H, s) 7.24(1H, d) |

TABLE 27

| Comp. Nos. | ¹H-NMR δ value (ppm) Solvent CDCl₃ |
|---|---|
| 475 | 1.03(3H, t) 1.86(5H, m) 2.87(2H, m) 3.60(3H, m) 4.36(1H, q) 6.39(1H, d) 7.00(1H, s) 7.27(1H, d) |
| 483 | 1.10(3H, t) 2.20(1H, m) 2.50(1H, m) 2.80(3H, s) 3.60(3H, s) 4.20(1H, m) 6.45(1H, d) 7.05(1H, s) 7.20(1H, d) |
| 484 | 1.10(3H, t) 2.20(1H, m) 2.50(1H, m) 2.70(3H, s) 3.60(3H, s) 4.10(1H, m) 6.20(1H, d) 7.0(1H, s) 7.20(1H, d) |
| 485 | 1.09(3H, m) 1.19(3H, t) 1.96(2H, m) 2.45(2H, m) 3.58(3H, s) 3.82(1H, t) 6.40(1H, d) 6.68(1H, d) 7.17(1H, d) |
| 486 | 1.05(3H, t) 1.30(3H, t) 2.56(4H, m) 3.59(3H, s) 3.81(1H, m) 6.46(1H, d) 6.82(1H, d) 7.22(1H, d) |
| 505 | 1.15(6H, m) 1.28(3H, m) 2.81(2H, m) 3.59(3H, s) 4.16(1H, m) 6.40(1H, d) 7.09(1H, d) 7.26(1H, d) |
| 510 | 0.86(3H, t) 1.71(3H, s) 2.10(1H, m) 2.35(1H, m) 2.66(3H, d) 3.51(3H, s) 6.31(1H, s) 6.92(1H, s) 7.18(1H, d) |
| 511 | 0.97(3H, t) 1.17(1H, m) 1.43(1H, m) 1.80(3H, s) 2.09(1H, m) 2.32(1H, m) 2.73(3H, d) 3.59(3H, s) 6.39(1H, d) 6.97(1H, s) 7.24(1H, d) |
| 515 | 1.80(3H, d) 3.60(3H, s) 4.60(1H, m) 6.40(1H, s) 6.80(1H, s) 7.20(1H, d) |
| 549 | 1.59(6H, s) 2.91(1H, bs) 3.55(3H, s) 6.33(1H, s) 6.65(1H, s) 7.17(1H, d) |
| 551 | 1.42(3H, d) 3.58(3H, s) 5.35(1H, m) 6.39, 6.43(1H, s) 6.75(1H, s) 6.80(1H, bs) 7.25(1H, d) |

TABLE 28

| Comp. Nos. | ¹H-NMR δ value (ppm) Solvent CDCl₃ |
|---|---|
| 571 | 1.45(3H, d) 2.40(3H, s) 3.10(1H, s) 3.60(3H, s) 3.90(1H, q) 6.40(1H, s) 6.70(1H, s) 7.15(1H, d) |
| 577 | 1.93(3H, d) 3.59(3H, s) 4.56(1H, q) 6.40(1H, d) 6.87(1H, s) 7.25(1H, s) |
| 585 | 0.90(3H, t) 1.54(3H, d) 3.45(2H, m) 3.58(3H, s) 4.52(1H, m) 6.38(1H, d) 6.73(1H, s) 7.20(1H, d) |
| 586 | 0.88(3H, t) 1.5~1.6(6H, m) 3.38(2H, m) 3.56(3H, s) 4.55(1H, m) 6.39(1H, d) 6.73(1H, s) 7.18(1H, d) |
| 623 | 2.44(3H, s) 3.58(3H, s) 3.80(3H, s) 4.64(2H, s) 6.40(1H, s) 7.15(1H, d) |
| 624 | 1.62(3H, d) 2.41(3H, s) 3.59(3H, s) 3.75(3H, s) 4.73(1H, q) 6.40(1H, s) 7.15(1H, d) |
| 635 | 2.44(3H, s) 3.54(3H, s) 5.32~5.50(2H, dd) 6.36(1H, s) 7.00~7.15(2H, m) |
| 646 | 0.96(6H, d) 2.14(1H, m) 3.03(2H, m) 3.59(3H, s) 6.41(1H, s) 7.31(1H, d) 10.7(1H, s) |

TABLE 28-continued

| Comp. Nos. | ¹H-NMR δ value (ppm) Solvent CDCl₃ |
|---|---|
| 647 | 0.94(6H, d) 2.07(1H, m) 2.84(2H, d) 3.59(3H, s) 3.93(3H, s) 6.40(1H, s) 7.25(1H, d) |
| 649 | 0.91(3H, m) 1.33~1.38(4H, m) 1.66~1.73(2H, m) 3.12(2H, m) 3.60(1H, s) 6.41(1H, s) 7.30(1H, d) |
| 655 | 3.59(3H, s) 3.92(3H, s) 6.40(1H, s) 7.31(1H, d) 8.20(1H, s) |
| 656 | 2.56(3H, s) 3.56(3H, s) 4.03(3H, s) 6.41(1H, s) 7.32(1H, d) |

TABLE 29

| Comp. Nos. | ¹H-NMR δ value (ppm) Solvent CDCl₃ |
|---|---|
| 657 | 1.56(3H, d) 3.57(4H, m) 3.96(3H, s) 5.18(1H, m) 6.37(1H, d) 7.28(1H, d) |
| 661 | 1.44(3H, t) 2.96(3H, s) 3.58(3H, s) 4.46(2H, q) 4.73(2H, s) 6.39(1H, s) 7.34(1H, d) |
| 664 | 1.37(3H, t) 1.43(3H, t) 3.08(2H, q) 3.58(3H, s) 4.45(2H, q) 4.71(2H, s) 6.39(1H, s) 7.34(1H, d) |
| 666 | 1.46(3H, t) 3.58(3H, s) 4.53(2H, q) 6.40(1H, s) 7.39(1H, d) 10.04(1H, s) |
| 670 | 1.43(3H, t) 1.88(3H, d) 3.60(3H, s) 4.45(2H, q) 5.62(1H, q) 6.41(1H, s) 7.29(1H, d) |
| 678 | 1.50(3H, d) 3.30(3H, d) 3.60(3H, s) 4.40(1H, m) 6.40(1H, d) 6.80(1H, s) 6.90(1H, dd) |
| 684 | 1.8(3H, dd) 2.75(3H, s) 3.80(3H, s) 4.20(1H, q) 6.20(1H, d) 7.00(2H, m) |
| 688 | 1.38(3H, t) 1.80(3H, dd) 2.90(2H, m) 3.60(3H, d) 4.40(1H, q) 6.40(1H, d) 7.00(2H, m) 7.20(1H, s) |
| 691 | 0.89(3H, m) 1.84(2H, m) 3.27(3H, s) 3.53(3H, s) 4.13(1H, q) 6.35(1H, d) 6.72(1H, d) 6.87(1H, dd) |
| 694 | 1.04(3H, t) 1.31(3H, t) 2.17(1H, m) 2.45(1H, m) 2.87(2H, m) 3.58(3H, s) 4.19(1H, m) 6.39(1H, d) 6.96(1H, dd) 7.03(1H, d) |
| 712 | 1.00(2H, t) 1.90(2H, m) 2.60(1H, bs) 3.50(3H, s) 3.60(1H, q) 6.30(1H, s) 6.60(1H, s) 7.40(1H, d) |

TABLE 30

| Comp. Nos. | ¹H-NMR δ value (ppm) Solvent CDCl₃ |
|---|---|
| 713 | 1.53(3H, d) 3.31(3H, d) 3.58(3H, s) 4.45(1H, m) 6.39(1H, d) 6.70(1H, s) 7.35(1H, d) |
| 717 | 1.82(3H, dd) 2.82(3H, s) 3.57(3H, s) 4.37(1H, q) 6.39(1H, d) 6.96(1H, s) 7.41(1H, d) |
| 720 | 1.35(3H, m) 1.83(3H, dd) 2.92(2H, m) 3.59(3H, s) 4.39(1H, q) 6.39(1H, d) 6.95(1H, s) 7.40(1H, d) |
| 750 | 1.33(3H, t) 2.80(2H, q) 3.70(3H, s) 6.35(1H, s) 6.47(1H, s) 7.23(1H, d) |
| 752 | 1.63(3H, d) 3.07(2H, m) 3.56(3H, d) 4.27(1H, q) 6.37(1H, d) 6.71(1H, d) 7.19(1H, d) |
| 757 | 1.11(3H, m) 2.20(1H, m) 2.54(1H, m) 3.53~3.62(4H, m) 3.86(1H, m) 4.36(1H, m) 6.38(1H, d) 7.05(1H, s) 6.26(1H, d) |
| 764 | 0.85(3H, m) 1.82(2H, m) 3.24(3H, s) 3.51(3H, s) 4.11(1H, q) 6.32(1H, d) 6.98(1H, d) 7.12(1H, d) |
| 765 | 1.61(3H, d) 3.73(3H, s) 3.79(2H, m) 4.73(1H, m) 6.38(1H, s) 6.81(1H, s) 7.23(1H, d) |
| 766 | 1.54(3H, d) 3.58(3H, s) 3.71(2H, m) 4.45(1H, m) 4.64(2H, m) 6.39(1H, s) 6.78(1H, s) 7.19(1H, d) |
| 770 | 1.22~1.28(6H, m) 1.79(3H, dd) 3.59(3H, s) 3.66~4.07(4H, dd) 5.47(1H, q) 6.39(1H, d) 6.79(1H, s) 7.16(1H, d) |
| 771 | 0.93(3H, m) 1.84(2H, m) 3.31(3H, s) 3.57(3H, s) 4.17(1H, q) 6.38(1H, q) 6.75(1H, d) 6.90(1H, dd) |

The herbicide of the present invention comprises a benzofuran-7-yl uracil derivative of the formula (1) as an active ingredient.

For the compound of the present invention to be used as a herbicide, the compound of the present invention may be used by itself. However, it may be used in the form of a formulation such as a dust, a wettable powder, an emulsifiable concentrate, a microgranule or a granule by blending it with a carrier, a surfactant, a dispersant or an adjuvant, which is commonly used for formulations.

The carrier to be used for such formulations, may, for example, be a solid carrier such as talc, bentonite, clay, kaolin, diatomaceous earth, fine silica, vermiculite, calcium carbonate, slaked lime, silica sand, ammonium sulfate or urea, or a liquid carrier such as isopropyl alcohol, xylene, cyclohexane or methylnaphthalene.

As the surfactant and dispersant, a metal salt of alkylbenzenesulfonic acid, a metal salt of dinaphthylmethane disulfonic acid, a salt of alcohol sulfuric acid ester, an alkylaryl sulfonate, a lignin sulfonate, a polyoxyethylene glycol ether, a polyoxyethylene alkylaryl ether or a polyoxyethylene sorbitol monoalkylate may, for example, be mentioned. The adjuvant may, for example, be carboxymethyl cellulose, polyethylene glycol or gum arabic. In practical use, the herbicide may be diluted to a suitable concentration before application, or may be directly applied.

The herbicide of the present invention may be used for application to foliage, soil or water surface. The blending proportion of the active ingredient is suitably selected as the case requires. However, in a case of a dust or a granule, the proportion of the active ingredient is selected suitably within a range of from 0.01 to 10% by weight, preferably from 0.05 to 5% by weight. In a case of an emulsifiable concentrate or a wettable powder, the proportion is selected suitably within a range of from 1 to 50% by weight, preferably from 5 to 30% by weight.

The dose of the herbicide of the present invention varies depending upon the type of the compound, the weeds to be controlled, the germination tendency, the environmental conditions and the type of the formulation to be used. However, in the case of a dust or a granule which is used by itself, the dose of the active ingredient is selected suitably within a range of from 0.1 g to 5 kg, preferably from 1 g to 1 kg, per 10 ares. In a case of an emulsifiable concentrate or a wettable powder which is used in a liquid state, the dose of the active ingredient is selected suitably within a range of from 0.1 to 50,000 ppm, preferably from 10 to 10,000 ppm.

Further, the compound of the present invention may be used in combination with an insecticide, a fungicide, other herbicide, a plant growth controlling agent, a fertilizer or the like, as the case requires.

Now, the formulation method will be described with reference to typical Formulation Examples. The compounds, types of the additives and blending ratios are not limited to such specific Examples and may be changed within wide ranges. In the following description, "parts" means "parts by weight".

FORMULATION EXAMPLE 1
(Wettable powder)

To 10 parts of Compound (4), 0.5 part of polyoxyethyleneoctylphenyl ether, 0.5 part of sodium β-naphthalene sulfonate-formalin condensate, 20 parts of diatomaceous earth and 69 parts of clay were mixed and pulverized to obtain a wettable powder.

FORMULATION EXAMPLE 2
(Wettable powder)

To 10 parts of Compound (78), 0.5 part of polyoxyethyleneoctylphenyl ether, 0.5 part of sodium β-naphthalene sulfonate-formalin condensate, 20 parts of diatomaceous earth, 5 parts of fine silica and 64 parts of clay were mixed and pulverized to obtain a wettable powder.

FORMULATION EXAMPLE 3
(Wettable powder)

To 10 parts of Compound (201), 0.5 part of polyoxyethyleneoctylphenyl ether, 0.5 part of sodium β-naphthalene sulfonate-formalin condensate, 20 parts of diatomaceous earth, 5 parts of fine silica and 64 parts of calcium carbonate, were mixed and pulverized to obtain a wettable powder.

FORMULATION EXAMPLE 4
(Emulsifiable concentrate)

To 30 parts of Compound (8), 60 parts of a mixture comprising equal amounts of xylene and isophorone and 10 parts of a mixture comprising a polyoxyethylene sorbitol alkylate surfactant, a polyoxyethylenealkylaryl polymer and an alkylaryl sulfonate, were added, and the mixture was thoroughly stirred to obtain an emulsifiable concentrate.

FORMULATION EXAMPLE 5
(Granule)

10 Parts of Compound (44), 80 parts of a bulking agent comprising a 1:3 mixture of talc and bentonite, 5 parts of fine silica, 5 parts of a mixture comprising a polyoxyethylene sorbitol alkylate surfactant, a polyoxyethylenealkylaryl polymer and an alkylaryl sulfonate and 10 parts of water were mixed and thoroughly kneaded to obtain a paste, which was extruded from sieve apertures with a diameter of 0.7 mm. The extruded product was dried and then cut into a length of from 0.5 to 1 mm to obtain granules.

Now, the effects of the compounds of the present invention will be described with reference to Test Examples. Further, as comparative agents, the following compounds were used.

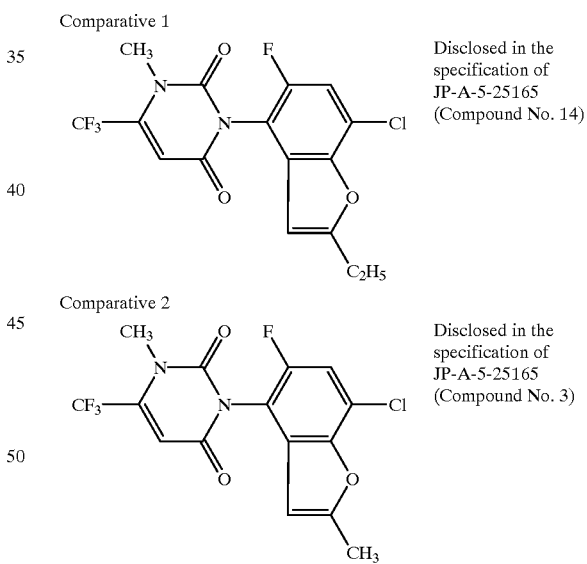

Test Example 1
(Test on herbicidal effects by paddy field soil treatment)

In a plastic pot (surface area: 100 cm$^2$) filled with paddy field soil, barnyardgrass (Ec), monochoria (Mo) and bulrush (Sc) were sown after puddling and leveling, and flooded to a water depth of 3 cm. Next day, a wettable powder prepared in accordance with Formulation Example 1 was diluted with water and applied dropwise to the water surface. The dose was 100 g of the active ingredient per 10 ares. The plants were then cultured in a green house, and the evaluation of the herbicidal effects was conducted on the 21st day after the application in accordance with the standards as identified in Table 31. The results are shown in Tables 32–40.

TABLE 31

| Index No. | Herbicidal effects (growth-controlling degree) or phytotoxicity |
|---|---|
| 5 | Herbicidal effect or phytotoxicity: at least 90% |
| 4 | Herbicidal effect or phytotoxicity: at least 70% and less than 90% |
| 3 | Herbicidal effect or phytotoxicity: at least 50% and less than 70% |
| 2 | Herbicidal effect or phytotoxicity: at least 30% and less than 50% |
| 1 | Herbicidal effect or phytotoxicity: at least 10% and less than 30% |
| 0 | Herbicidal effect or phytotoxicity: 0 to less than 10% |

TABLE 32

| Compound Nos. | Herbicidal effects | | |
|---|---|---|---|
| | Ec | Mo | Sc |
| 1 | 5 | 5 | 5 |
| 2 | 5 | 5 | 5 |
| 3 | 5 | 5 | 5 |
| 4 | 5 | 5 | 5 |
| 6 | 5 | 5 | 5 |
| 7 | 5 | 5 | 5 |
| 8 | 5 | 5 | 5 |
| 9 | 5 | 5 | 5 |
| 10 | 5 | 5 | 5 |
| 12 | 5 | 5 | 5 |
| 13 | 5 | 5 | 5 |
| 14 | 5 | 5 | 5 |
| 15 | 5 | 5 | 5 |
| 16 | 5 | 5 | 5 |
| 19 | 5 | 5 | 5 |
| 20 | 5 | 5 | 5 |
| 21 | 5 | 5 | 5 |
| 22 | 5 | 5 | 5 |
| 23 | 5 | 5 | 5 |
| 28 | 5 | 5 | 5 |
| 29 | 5 | 5 | 5 |
| 30 | 5 | 5 | 5 |
| 31 | 5 | 5 | 5 |
| 33 | 5 | 5 | 5 |
| 35 | 5 | 5 | 5 |
| 37 | 5 | 5 | 5 |
| 42 | 5 | 5 | 5 |
| 43 | 5 | 5 | 5 |
| 44 | 5 | 5 | 5 |

TABLE 33

| Compound Nos. | Herbicidal effects | | |
|---|---|---|---|
| | Ec | Mo | Sc |
| 45 | 5 | 5 | 5 |
| 70 | 5 | 5 | 5 |
| 71 | 5 | 5 | 5 |
| 72 | 5 | 5 | 5 |
| 75 | 5 | 5 | 5 |
| 78 | 5 | 5 | 5 |
| 83 | 5 | 5 | 5 |
| 84 | 5 | 5 | 5 |
| 95 | 5 | 5 | 5 |
| 98 | 5 | 5 | 5 |
| 101 | 5 | 5 | 5 |
| 111 | 5 | 5 | 5 |
| 140 | 5 | 5 | 5 |
| 141 | 5 | 5 | 5 |
| 142 | 5 | 5 | 5 |
| 143 | 5 | 5 | 5 |
| 147 | 5 | 5 | 5 |
| 152 | 5 | 5 | 5 |
| 153 | 5 | 5 | 5 |
| 165 | 5 | 5 | 5 |
| 166 | 5 | 5 | 5 |
| 187 | 5 | 5 | 4 |
| 195 | 5 | 5 | 5 |
| 196 | 5 | 5 | 5 |
| 197 | 5 | 5 | 5 |
| 198 | 5 | 5 | 5 |
| 200 | 5 | 5 | 5 |
| 201 | 5 | 5 | 5 |
| 202 | 5 | 5 | 5 |

TABLE 34

| Compound Nos. | Herbicidal effects | | |
|---|---|---|---|
| | Ec | Mo | Sc |
| 207 | 5 | 5 | 5 |
| 208 | 5 | 5 | 5 |
| 209 | 5 | 5 | 5 |
| 210 | 5 | 5 | 5 |
| 213 | 5 | 5 | 5 |
| 222 | 5 | 5 | 5 |
| 228 | 5 | 5 | 5 |
| 233 | 5 | 5 | 5 |
| 230 | 5 | 5 | 5 |
| 239 | 5 | 5 | 5 |
| 245 | 5 | 5 | 5 |
| 265 | 5 | 5 | 5 |
| 266 | 5 | 5 | 5 |
| 272 | 5 | 5 | 5 |
| 289 | 5 | 5 | 5 |
| 299 | 5 | 5 | 5 |
| 303 | 5 | 5 | 5 |
| 350 | 5 | 5 | 5 |
| 374 | 5 | 5 | 5 |
| 375 | 5 | 5 | 5 |
| 379 | 5 | 5 | 5 |
| 383 | 5 | 5 | 5 |
| 392 | 5 | 5 | 5 |
| 393 | 5 | 5 | 5 |
| 394 | 5 | 5 | 5 |
| 397 | 5 | 5 | 5 |
| 398 | 5 | 5 | 5 |
| 400 | 5 | 5 | 5 |
| 401 | 5 | 5 | 5 |

TABLE 35

| Compound Nos. | Herbicidal effects | | |
|---|---|---|---|
| | Ec | Mo | Sc |
| 402 | 5 | 5 | 5 |
| 404 | 5 | 5 | 5 |
| 405 | 5 | 5 | 5 |
| 406 | 5 | 5 | 5 |
| 407 | 5 | 5 | 5 |
| 409 | 5 | 5 | 5 |
| 410 | 5 | 5 | 5 |
| 411 | 5 | 5 | 5 |
| 412 | 5 | 5 | 5 |
| 417 | 5 | 5 | 5 |
| 418 | 5 | 5 | 5 |

TABLE 35-continued

| Compound | Herbicidal effects | | |
|---|---|---|---|
| Nos. | Ec | Mo | Sc |
| 421 | 5 | 5 | 5 |
| 423 | 5 | 5 | 5 |
| 424 | 5 | 5 | 5 |
| 427 | 5 | 5 | 5 |
| 432 | 5 | 5 | 5 |
| 433 | 5 | 5 | 5 |
| 435 | 5 | 5 | 5 |
| 436 | 5 | 5 | 5 |
| 439 | 5 | 5 | 5 |
| 440 | 5 | 5 | 5 |
| 441 | 5 | 5 | 5 |
| 442 | 5 | 5 | 5 |
| 443 | 5 | 5 | 5 |
| 444 | 5 | 5 | 5 |
| 445 | 5 | 5 | 5 |
| 446 | 5 | 5 | 5 |
| 447 | 5 | 5 | 5 |
| 448 | 5 | 5 | 5 |

TABLE 36

| Compound | Herbicidal effects | | |
|---|---|---|---|
| Nos. | Ec | Mo | Sc |
| 449 | 5 | 5 | 5 |
| 450 | 5 | 5 | 5 |
| 451 | 5 | 5 | 5 |
| 452 | 5 | 5 | 5 |
| 453 | 5 | 5 | 5 |
| 454 | 5 | 5 | 5 |
| 455 | 5 | 5 | 5 |
| 456 | 5 | 5 | 5 |
| 457 | 5 | 5 | 5 |
| 458 | 5 | 5 | 5 |
| 459 | 5 | 5 | 5 |
| 460 | 5 | 5 | 5 |
| 461 | 5 | 5 | 5 |
| 462 | 5 | 5 | 5 |
| 463 | 5 | 5 | 5 |
| 464 | 5 | 5 | 5 |
| 466 | 5 | 5 | 4 |
| 467 | 5 | 5 | 5 |
| 468 | 5 | 5 | 5 |
| 469 | 5 | 5 | 5 |
| 470 | 5 | 5 | 5 |
| 471 | 5 | 5 | 5 |
| 472 | 5 | 5 | 5 |
| 473 | 5 | 5 | 5 |
| 476 | 5 | 5 | 5 |
| 479 | 5 | 5 | 5 |
| 482 | 5 | 5 | 5 |
| 483 | 5 | 5 | 5 |
| 484 | 5 | 5 | 5 |

TABLE 37

| Compound | Herbicidal effects | | |
|---|---|---|---|
| Nos. | Ec | Mo | Sc |
| 508 | 5 | 5 | 5 |
| 510 | 5 | 5 | 5 |
| 511 | 5 | 5 | 5 |
| 513 | 5 | 5 | 5 |
| 515 | 5 | 5 | 5 |
| 521 | 5 | 5 | 5 |
| 524 | 5 | 5 | 5 |
| 539 | 5 | 5 | 5 |
| 571 | 5 | 5 | 5 |

TABLE 37-continued

| Compound | Herbicidal effects | | |
|---|---|---|---|
| Nos. | Ec | Mo | Sc |
| 572 | 5 | 5 | 5 |
| 577 | 5 | 5 | 5 |
| 578 | 5 | 5 | 5 |
| 584 | 5 | 5 | 5 |
| 591 | 5 | 5 | 5 |
| 592 | 5 | 5 | 5 |
| 605 | 5 | 5 | 5 |
| 606 | 5 | 5 | 5 |
| 607 | 5 | 5 | 5 |
| 610 | 5 | 5 | 5 |
| 612 | 5 | 5 | 5 |
| 617 | 5 | 5 | 5 |
| 618 | 5 | 5 | 5 |
| 619 | 5 | 5 | 5 |
| 622 | 5 | 5 | 5 |
| 623 | 5 | 5 | 5 |
| 624 | 5 | 5 | 5 |
| 630 | 5 | 5 | 5 |
| 631 | 5 | 5 | 5 |
| 634 | 5 | 5 | 5 |

TABLE 38

| Compound | Herbicidal effects | | |
|---|---|---|---|
| Nos. | Ec | Mo | Sc |
| 635 | 5 | 5 | 5 |
| 636 | 5 | 5 | 5 |
| 639 | 5 | 5 | 5 |
| 640 | 5 | 5 | 5 |
| 641 | 5 | 5 | 5 |
| 642 | 5 | 5 | 4 |
| 643 | 5 | 5 | 5 |
| 644 | 5 | 5 | 5 |
| 645 | 5 | 5 | 5 |
| 646 | 5 | 5 | 5 |
| 647 | 5 | 5 | 5 |
| 648 | 5 | 5 | 5 |
| 649 | 5 | 5 | 5 |
| 650 | 5 | 5 | 5 |
| 651 | 5 | 5 | 5 |
| 653 | 5 | 5 | 4 |
| 655 | 5 | 5 | 5 |
| 656 | 5 | 5 | 5 |
| 657 | 5 | 5 | 5 |
| 658 | 5 | 5 | 5 |
| 659 | 5 | 5 | 5 |
| 660 | 5 | 5 | 5 |
| 661 | 5 | 5 | 5 |
| 662 | 5 | 5 | 5 |
| 663 | 5 | 5 | 5 |
| 664 | 5 | 5 | 5 |
| 665 | 5 | 5 | 5 |
| 666 | 5 | 5 | 5 |
| 667 | 5 | 5 | 5 |

TABLE 39

| Compound | Herbicidal effects | | |
|---|---|---|---|
| Nos. | Ec | Mo | Sc |
| 668 | 5 | 5 | 5 |
| 669 | 5 | 5 | 5 |
| 670 | 5 | 5 | 5 |
| 671 | 5 | 5 | 5 |
| 672 | 5 | 5 | 5 |
| 674 | 5 | 5 | 5 |
| 676 | 5 | 5 | 5 |

TABLE 39-continued

| Compound Nos. | Herbicidal effects | | |
|---|---|---|---|
| | Ec | Mo | Sc |
| 677 | 5 | 5 | 5 |
| 680 | 5 | 5 | 5 |
| 681 | 5 | 5 | 5 |
| 682 | 5 | 5 | 5 |
| 684 | 5 | 5 | 5 |
| 685 | 5 | 5 | 5 |
| 686 | 5 | 5 | 5 |
| 688 | 5 | 5 | 5 |
| 698 | 5 | 5 | 5 |
| 699 | 5 | 5 | 5 |
| 700 | 5 | 5 | 5 |
| 701 | 5 | 5 | 5 |
| 702 | 5 | 5 | 5 |
| 703 | 5 | 5 | 5 |
| 704 | 5 | 5 | 4 |
| 705 | 5 | 5 | 5 |
| 706 | 5 | 5 | 5 |
| 707 | 5 | 5 | 5 |
| 708 | 5 | 5 | 5 |
| 709 | 5 | 5 | 5 |
| 710 | 5 | 5 | 5 |
| 711 | 5 | 5 | 5 |

TABLE 40

| Compound Nos. | Herbicidal effects | | |
|---|---|---|---|
| | Ec | Mo | Sc |
| 712 | 5 | 5 | 5 |
| 724 | 5 | 5 | 5 |
| 725 | 5 | 5 | 5 |
| 726 | 5 | 5 | 5 |
| 727 | 5 | 5 | 5 |

Test Example 2

(Test on herbicidal effects by upland field soil treatment)

In a plastic pot (surface area: 120 cm$^2$) filled with sand, pale smartweed (Po), slender amaranth (Am), common lambsquarters (Ch) and rice flatsedge (Ci) were sown and covered with soil. A wettable powder prepared in accordance with Formulation Example 1 was diluted with water and applied uniformly to the soil surface by a small-sized sprayer in an amount of 100 lit./10 ares so as to apply 100 g of the active ingredient per 10 ares. The plants were then cultured in a green house, and the evaluation of the herbicidal effects was conducted on the 21st day after the application in accordance with the standards as identified in Table 31. The results are shown in Tables 41–49. Symbol - represents "not tested".

TABLE 41

| Compound Nos. | Herbicidal effects | | | |
|---|---|---|---|---|
| | Po | Am | Ch | Ci |
| 1 | 5 | 5 | 5 | 5 |
| 2 | 5 | 5 | 5 | 5 |
| 3 | 5 | 5 | 5 | 5 |
| 4 | 5 | 5 | 5 | 5 |
| 6 | 5 | 5 | 5 | 5 |
| 7 | 5 | 5 | 5 | 5 |
| 8 | 5 | 5 | 5 | 5 |
| 9 | 5 | 5 | 5 | 5 |
| 10 | 5 | 5 | 5 | 5 |
| 12 | 5 | 5 | 5 | 5 |
| 13 | 5 | 5 | 5 | 5 |
| 14 | 5 | 5 | 5 | 5 |
| 15 | 5 | 5 | 5 | 5 |
| 16 | 5 | 5 | 5 | 5 |
| 19 | 5 | 5 | 5 | 5 |
| 20 | 5 | 5 | 5 | 5 |
| 21 | 5 | 5 | 5 | 5 |
| 22 | 5 | 5 | 5 | 5 |
| 23 | 5 | 5 | 5 | 5 |
| 25 | 5 | 5 | 5 | 5 |
| 28 | 5 | 5 | 5 | 5 |
| 29 | 5 | 5 | 5 | 5 |
| 30 | 5 | 5 | 5 | 5 |
| 31 | 5 | 5 | 5 | 5 |
| 33 | 5 | 5 | 5 | 5 |
| 35 | 5 | 5 | 5 | 5 |
| 37 | 5 | 5 | 5 | 5 |
| 42 | 5 | 5 | 5 | 5 |
| 43 | 5 | 5 | 5 | 5 |

TABLE 42

| Compound Nos. | Herbicidal effects | | | |
|---|---|---|---|---|
| | Po | Am | Ch | Ci |
| 44 | 5 | 5 | 5 | 5 |
| 45 | 5 | 5 | 5 | 5 |
| 70 | 5 | 5 | 5 | 5 |
| 71 | 5 | 5 | 5 | 5 |
| 72 | 5 | 5 | 5 | 5 |
| 74 | 5 | 5 | 5 | 5 |
| 75 | 5 | 5 | 5 | 5 |
| 78 | 5 | 5 | 5 | 5 |
| 83 | 5 | 5 | 5 | 5 |
| 84 | 5 | 5 | 5 | 5 |
| 95 | 5 | 5 | 5 | 5 |
| 98 | 5 | 5 | 5 | 5 |
| 101 | 5 | 5 | 5 | 5 |
| 111 | 5 | 5 | 5 | 5 |
| 117 | 5 | 5 | 5 | 5 |
| 140 | 5 | 5 | 5 | 5 |
| 141 | 5 | 5 | 5 | 5 |
| 142 | 5 | 5 | 5 | 5 |
| 143 | 5 | 5 | 5 | 5 |
| 147 | 5 | 5 | 5 | 5 |
| 152 | 5 | 5 | 5 | 5 |
| 153 | 5 | 5 | 5 | 5 |
| 165 | 5 | 5 | 5 | 5 |
| 166 | 5 | 5 | 5 | 5 |
| 195 | 5 | 5 | 5 | 5 |
| 196 | 5 | 5 | 5 | 5 |
| 197 | 5 | 5 | 5 | 5 |
| 198 | 5 | 5 | 5 | 5 |
| 200 | 5 | 5 | 5 | 5 |

TABLE 43

| Compound Nos. | Herbicidal effects | | | |
|---|---|---|---|---|
| | Po | Am | Ch | Ci |
| 201 | 5 | 5 | 5 | 5 |
| 202 | 5 | 5 | 5 | 5 |
| 206 | 5 | 5 | 5 | 5 |
| 207 | 5 | 5 | 5 | 5 |
| 208 | 5 | 5 | 5 | 5 |
| 209 | 5 | 5 | 5 | 5 |
| 210 | 5 | 5 | 5 | 5 |

TABLE 43-continued

| Compound Nos. | Herbicidal effects | | | |
|---|---|---|---|---|
| | Po | Am | Ch | Ci |
| 213 | 5 | 5 | 5 | 5 |
| 219 | 5 | 5 | 5 | 5 |
| 222 | 5 | 5 | 5 | 5 |
| 227 | 5 | 5 | 5 | 5 |
| 228 | 5 | 5 | 5 | 5 |
| 230 | 5 | 5 | 5 | 5 |
| 231 | 5 | 5 | 5 | 5 |
| 233 | 5 | 5 | 5 | 5 |
| 238 | 5 | 5 | 5 | 5 |
| 239 | 5 | 5 | 5 | 5 |
| 240 | 5 | 5 | 5 | 5 |
| 241 | 5 | 5 | 5 | 5 |
| 245 | 5 | 5 | 5 | 5 |
| 246 | 5 | 5 | 5 | 5 |
| 247 | 5 | 5 | 5 | 5 |
| 248 | 5 | 5 | 5 | 5 |
| 265 | 5 | 5 | 5 | 5 |
| 266 | 5 | 5 | 5 | 5 |
| 267 | 5 | 5 | 5 | 5 |
| 269 | 5 | 5 | 5 | 5 |
| 270 | 5 | 5 | 5 | 5 |
| 272 | 5 | 5 | 5 | 5 |

TABLE 44

| Compound Nos. | Herbicidal effects | | | |
|---|---|---|---|---|
| | Po | Am | Ch | Ci |
| 289 | 5 | 5 | 5 | 5 |
| 299 | 5 | 5 | 5 | 5 |
| 301 | 5 | 5 | 5 | 5 |
| 303 | 5 | 5 | 5 | 5 |
| 305 | 5 | 5 | 5 | 5 |
| 349 | 5 | 5 | 5 | 5 |
| 350 | 5 | 5 | 5 | 5 |
| 374 | 5 | 5 | 5 | 5 |
| 375 | 5 | 5 | 5 | 5 |
| 379 | 5 | 5 | 5 | 5 |
| 383 | 5 | 5 | 5 | 5 |
| 392 | 5 | 5 | 5 | 5 |
| 393 | 5 | 5 | 5 | 5 |
| 394 | 5 | 5 | 5 | 5 |
| 397 | 5 | 5 | 5 | 5 |
| 398 | 5 | 5 | 5 | 5 |
| 400 | 5 | 5 | 5 | 5 |
| 401 | 5 | 5 | 5 | 5 |
| 402 | 5 | 5 | 5 | 5 |
| 404 | 5 | 5 | 5 | 5 |
| 405 | 5 | 5 | 5 | 5 |
| 406 | 5 | 5 | 5 | 5 |
| 407 | 5 | 5 | 5 | 5 |
| 409 | 5 | 5 | 5 | 5 |
| 410 | 5 | 5 | 5 | 5 |
| 411 | 5 | 5 | 5 | 5 |
| 412 | 5 | 5 | 5 | 5 |
| 417 | 5 | 5 | 5 | 5 |
| 418 | 5 | 5 | 5 | 5 |

TABLE 45

| Compound Nos. | Herbicidal effects | | | |
|---|---|---|---|---|
| | Po | Am | Ch | Ci |
| 421 | 5 | 5 | 5 | 5 |
| 423 | 5 | 5 | 5 | 5 |
| 424 | 5 | 5 | 5 | 5 |
| 427 | 5 | 5 | 5 | 5 |
| 432 | 5 | 5 | 5 | 5 |

TABLE 45-continued

| Compound Nos. | Herbicidal effects | | | |
|---|---|---|---|---|
| | Po | Am | Ch | Ci |
| 433 | 5 | 5 | 5 | 5 |
| 435 | 5 | 5 | 5 | 5 |
| 436 | 5 | 5 | 5 | 5 |
| 439 | 5 | 5 | 5 | — |
| 440 | 5 | 5 | 5 | 5 |
| 441 | 5 | 5 | 5 | — |
| 442 | 5 | 5 | 5 | 5 |
| 443 | 5 | 5 | 5 | 5 |
| 444 | 5 | 5 | 5 | 5 |
| 445 | 5 | 5 | 5 | 5 |
| 446 | 5 | 5 | 5 | 5 |
| 447 | 5 | 5 | 5 | 5 |
| 448 | 5 | 5 | 5 | 5 |
| 449 | 5 | 5 | 5 | 5 |
| 450 | 5 | 5 | 5 | 5 |
| 452 | 5 | 5 | 5 | — |
| 453 | 5 | 5 | 5 | 5 |
| 454 | 5 | 5 | 5 | 5 |
| 455 | 5 | 5 | 5 | 5 |
| 456 | 5 | 5 | 5 | 5 |
| 457 | 5 | 5 | 5 | 5 |
| 458 | 5 | 5 | 5 | 5 |
| 459 | 5 | 5 | 5 | 5 |
| 460 | 5 | 5 | 5 | 5 |

TABLE 46

| Compound Nos. | Herbicidal effects | | | |
|---|---|---|---|---|
| | Po | Am | Ch | Ci |
| 461 | 5 | 5 | 5 | 5 |
| 462 | 5 | 5 | 5 | 5 |
| 463 | 5 | 5 | 5 | 5 |
| 464 | 5 | 5 | 5 | 5 |
| 466 | 5 | 5 | 5 | 5 |
| 467 | 5 | 5 | 5 | 5 |
| 468 | 5 | 5 | 5 | 5 |
| 469 | 5 | 5 | 5 | 5 |
| 470 | 5 | 5 | 5 | — |
| 471 | 5 | 5 | 5 | 5 |
| 472 | 5 | 5 | 5 | — |
| 473 | 5 | 5 | 5 | 5 |
| 482 | 5 | 5 | 5 | 5 |
| 483 | 5 | 5 | 5 | 5 |
| 484 | 5 | 5 | 5 | 5 |
| 508 | 5 | 5 | 5 | 5 |
| 510 | 5 | 5 | 5 | 5 |
| 511 | 5 | 5 | 5 | 5 |
| 513 | 5 | 5 | 5 | 5 |
| 515 | 5 | 5 | 5 | 5 |
| 521 | 5 | 5 | 5 | 5 |
| 524 | 5 | 5 | 5 | 5 |
| 539 | 5 | 5 | 5 | 5 |
| 571 | 5 | 5 | 5 | 5 |
| 572 | 5 | 5 | 5 | 5 |
| 577 | 5 | 5 | 5 | 5 |
| 578 | 5 | 5 | 5 | 5 |
| 584 | 5 | 5 | 5 | 5 |
| 591 | 5 | 5 | 5 | 5 |

TABLE 47

| Compound Nos. | Herbicidal effects | | | |
|---|---|---|---|---|
| | Po | Am | Ch | Ci |
| 592 | 5 | 5 | 5 | 5 |
| 605 | 5 | 5 | 5 | 5 |
| 606 | 5 | 5 | 5 | 5 |

TABLE 47-continued

| Compound Nos. | Herbicidal effects | | | |
|---|---|---|---|---|
| | Po | Am | Ch | Ci |
| 607 | 5 | 5 | 5 | 5 |
| 610 | 5 | 5 | 5 | 5 |
| 612 | 5 | 5 | 5 | 5 |
| 617 | 5 | 5 | 5 | 5 |
| 618 | 5 | 5 | 5 | 5 |
| 619 | 5 | 5 | 5 | 5 |
| 622 | 5 | 5 | 5 | 5 |
| 623 | 5 | 5 | 5 | 5 |
| 624 | 5 | 5 | 5 | 5 |
| 630 | 5 | 5 | 5 | 5 |
| 631 | 5 | 5 | 5 | 5 |
| 632 | 5 | 5 | 5 | 5 |
| 634 | 5 | 5 | 5 | 5 |
| 635 | 5 | 5 | 5 | 5 |
| 636 | 5 | 5 | 5 | 5 |
| 639 | 5 | 5 | 5 | 5 |
| 640 | 5 | 5 | 5 | 5 |
| 643 | 5 | 5 | 5 | 5 |
| 644 | 4 | 5 | 5 | 5 |
| 645 | 5 | 5 | 5 | 5 |
| 646 | 5 | 5 | 5 | 5 |
| 647 | 5 | 5 | 5 | 5 |
| 648 | 5 | 5 | 5 | 5 |
| 649 | 5 | 5 | 5 | 5 |
| 651 | 5 | 5 | 5 | 5 |
| 652 | 5 | 5 | 5 | 5 |

TABLE 48

| Compound Nos. | Herbicidal effects | | | |
|---|---|---|---|---|
| | Po | Am | Ch | Ci |
| 653 | 5 | 5 | 5 | 5 |
| 655 | 5 | 5 | 5 | 5 |
| 656 | 5 | 5 | 5 | 5 |
| 657 | 5 | 5 | 5 | 5 |
| 658 | 5 | 5 | 5 | 5 |
| 659 | 5 | 5 | 5 | — |
| 660 | 5 | 5 | 5 | 5 |
| 661 | 5 | 5 | 5 | 5 |
| 662 | 5 | 5 | 5 | 5 |
| 663 | 5 | 5 | 5 | 5 |
| 664 | 5 | 5 | 5 | 5 |
| 665 | 5 | 5 | 5 | 5 |
| 666 | 5 | 5 | 5 | 5 |
| 667 | 5 | 5 | 5 | 5 |
| 668 | 5 | 5 | 5 | 5 |
| 669 | 5 | 5 | 5 | 5 |
| 670 | 5 | 5 | 5 | 5 |
| 671 | 5 | 5 | 5 | 5 |
| 672 | 5 | 5 | 5 | 5 |
| 673 | 5 | 5 | 5 | 5 |
| 674 | 5 | 5 | 5 | 5 |
| 675 | 5 | 5 | 5 | 5 |
| 676 | 5 | 5 | 5 | 5 |
| 677 | 5 | 5 | 5 | 5 |
| 680 | 5 | 5 | 5 | 5 |
| 681 | 5 | 5 | 5 | 5 |
| 682 | 5 | 5 | 5 | 5 |
| 684 | 5 | 5 | 5 | 5 |
| 685 | 5 | 5 | 5 | 5 |

TABLE 49

| Compound Nos. | Herbicidal effects | | | |
|---|---|---|---|---|
| | Po | Am | Ch | Ci |
| 686 | 5 | 5 | 5 | 5 |
| 688 | 5 | 5 | 5 | 5 |
| 698 | 5 | 5 | 5 | — |
| 699 | 5 | 5 | 5 | — |
| 700 | 5 | 5 | 5 | — |
| 701 | 5 | 5 | 5 | 5 |
| 702 | 5 | 5 | 5 | — |
| 703 | 5 | 5 | 5 | — |
| 704 | 5 | 5 | 5 | — |
| 705 | 5 | 5 | 5 | 5 |
| 706 | 5 | 5 | 5 | 5 |
| 707 | 5 | 5 | 5 | 5 |
| 708 | 5 | 5 | 5 | 5 |
| 709 | 5 | 5 | 5 | 5 |
| 710 | 5 | 5 | 5 | 5 |
| 711 | 5 | 5 | 5 | 5 |
| 712 | 5 | 5 | 5 | 5 |
| 724 | 5 | 5 | 5 | 5 |
| 725 | 5 | 5 | 5 | 5 |
| 726 | 5 | 5 | 5 | 5 |
| 727 | 5 | 5 | 5 | 5 |
| 730 | 5 | 5 | 5 | 5 |

Test Example 3

(Test on herbicidal effects by upland field foliage treatment)

In a plastic pot (surface area: 120 cm$^2$) filled with sand, pale smartweed (Po), slender amaranth (Am), common lambsquarters (Ch) and rice flatsedge (Ci) were sown and were cultured in a green house for 2 weeks. A wettable powder prepared in accordance with Formulation Example 1 was diluted with water and applied onto the entire foliages of the plants from above by a small-sized sprayer in an amount of 100 lit./10 ares so as to apply 100 g of the active ingredient per 10 ares. The plants were then cultured in the green house, and the evaluation of the herbicidal effects was conducted on the 14th day after the treatment in accordance with the standards as identified in Table 31. The results are shown in Tables 50–58.

TABLE 50

| Compound Nos. | Herbicidal effects | | | |
|---|---|---|---|---|
| | Po | Am | Ch | Ci |
| 1 | 5 | 5 | 5 | 5 |
| 2 | 5 | 5 | 5 | 5 |
| 3 | 5 | 5 | 5 | 5 |
| 4 | 5 | 5 | 5 | 5 |
| 6 | 5 | 5 | 5 | 5 |
| 7 | 5 | 5 | 5 | 5 |
| 8 | 5 | 5 | 5 | 5 |
| 9 | 5 | 5 | 5 | 5 |
| 10 | 5 | 5 | 5 | 5 |
| 12 | 5 | 5 | 5 | 5 |
| 13 | 5 | 5 | 5 | 5 |
| 14 | 5 | 5 | 5 | 5 |
| 15 | 5 | 5 | 5 | 5 |
| 16 | 5 | 5 | 5 | 5 |
| 19 | 5 | 5 | 5 | 5 |
| 20 | 5 | 5 | 5 | 5 |
| 21 | 5 | 5 | 5 | 5 |
| 22 | 5 | 5 | 5 | 5 |
| 23 | 5 | 5 | 5 | 5 |
| 25 | 5 | 5 | 5 | 5 |
| 28 | 5 | 5 | 5 | 5 |
| 29 | 5 | 5 | 5 | 5 |
| 30 | 5 | 5 | 5 | 5 |

TABLE 50-continued

| Compound Nos. | Herbicidal effects | | | |
|---|---|---|---|---|
| | Po | Am | Ch | Ci |
| 31 | 5 | 5 | 5 | 5 |
| 33 | 5 | 5 | 5 | 5 |
| 35 | 5 | 5 | 5 | 5 |
| 37 | 5 | 5 | 5 | 5 |
| 42 | 5 | 5 | 5 | 5 |
| 43 | 5 | 5 | 5 | 5 |

TABLE 51

| Compound Nos. | Herbicidal effects | | | |
|---|---|---|---|---|
| | Po | Am | Ch | Ci |
| 44 | 5 | 5 | 5 | 5 |
| 45 | 5 | 5 | 5 | 5 |
| 70 | 5 | 5 | 5 | 5 |
| 71 | 5 | 5 | 5 | 5 |
| 72 | 5 | 5 | 5 | 5 |
| 74 | 5 | 5 | 5 | 5 |
| 75 | 5 | 5 | 5 | 5 |
| 78 | 5 | 5 | 5 | 5 |
| 83 | 5 | 5 | 5 | 5 |
| 84 | 5 | 5 | 5 | 5 |
| 95 | 5 | 5 | 5 | 5 |
| 98 | 5 | 5 | 5 | 5 |
| 101 | 5 | 5 | 5 | 5 |
| 111 | 5 | 5 | 5 | 5 |
| 116 | 5 | 5 | 5 | 5 |
| 140 | 5 | 5 | 5 | 5 |
| 141 | 5 | 5 | 5 | 5 |
| 142 | 5 | 5 | 5 | 5 |
| 143 | 5 | 5 | 5 | 5 |
| 147 | 5 | 5 | 5 | 5 |
| 152 | 5 | 5 | 5 | 5 |
| 153 | 5 | 5 | 5 | 5 |
| 165 | 5 | 5 | 5 | 5 |
| 166 | 5 | 5 | 5 | 5 |
| 195 | 5 | 5 | 5 | 5 |
| 196 | 5 | 5 | 5 | 5 |
| 197 | 5 | 5 | 5 | 5 |
| 198 | 5 | 5 | 5 | 5 |
| 200 | 5 | 5 | 5 | 5 |

TABLE 52

| Compound Nos. | Herbicidal effects | | | |
|---|---|---|---|---|
| | Po | Am | Ch | Ci |
| 201 | 5 | 5 | 5 | 5 |
| 202 | 5 | 5 | 5 | 5 |
| 206 | 5 | 5 | 5 | 5 |
| 207 | 5 | 5 | 5 | 5 |
| 208 | 5 | 5 | 5 | 5 |
| 209 | 5 | 5 | 5 | 5 |
| 210 | 5 | 5 | 5 | 5 |
| 213 | 5 | 5 | 5 | 5 |
| 219 | 5 | 5 | 5 | 5 |
| 222 | 5 | 5 | 5 | 5 |
| 227 | 5 | 5 | 5 | 5 |
| 228 | 5 | 5 | 5 | 5 |
| 230 | 5 | 5 | 5 | 5 |
| 231 | 5 | 5 | 5 | 5 |
| 233 | 5 | 5 | 5 | 5 |
| 238 | 5 | 5 | 5 | 5 |
| 239 | 5 | 5 | 5 | 5 |
| 240 | 5 | 5 | 5 | 5 |
| 241 | 5 | 5 | 5 | 5 |
| 245 | 5 | 5 | 5 | 5 |
| 246 | 5 | 5 | 5 | 5 |

TABLE 52-continued

| Compound Nos. | Herbicidal effects | | | |
|---|---|---|---|---|
| | Po | Am | Ch | Ci |
| 247 | 5 | 5 | 5 | 5 |
| 248 | 5 | 5 | 5 | 5 |
| 265 | 5 | 5 | 5 | 5 |
| 266 | 5 | 5 | 5 | 5 |
| 267 | 5 | 5 | 5 | 5 |
| 269 | 5 | 5 | 5 | 5 |
| 272 | 5 | 5 | 5 | 5 |
| 289 | 5 | 5 | 5 | 5 |

TABLE 53

| Compound Nos. | Herbicidal effects | | | |
|---|---|---|---|---|
| | Po | Am | Ch | Ci |
| 299 | 5 | 5 | 5 | 5 |
| 301 | 5 | 5 | 5 | 5 |
| 303 | 5 | 5 | 5 | 5 |
| 305 | 5 | 5 | 5 | 5 |
| 349 | 5 | 5 | 5 | 5 |
| 350 | 5 | 5 | 5 | 5 |
| 374 | 5 | 5 | 5 | 5 |
| 375 | 5 | 5 | 5 | 5 |
| 379 | 5 | 5 | 5 | 5 |
| 383 | 5 | 5 | 5 | 5 |
| 392 | 5 | 5 | 5 | 5 |
| 393 | 5 | 5 | 5 | 5 |
| 394 | 5 | 5 | 5 | 5 |
| 397 | 5 | 5 | 5 | 5 |
| 398 | 5 | 5 | 5 | 5 |
| 400 | 5 | 5 | 5 | 5 |
| 401 | 5 | 5 | 5 | 5 |
| 402 | 5 | 5 | 5 | 5 |
| 404 | 5 | 5 | 5 | 5 |
| 405 | 5 | 5 | 5 | 5 |
| 406 | 5 | 5 | 5 | 5 |
| 407 | 5 | 5 | 5 | 5 |
| 409 | 5 | 5 | 5 | 5 |
| 410 | 5 | 5 | 5 | 5 |
| 411 | 5 | 5 | 5 | 5 |
| 412 | 5 | 5 | 5 | 5 |
| 417 | 5 | 5 | 5 | 5 |
| 418 | 5 | 5 | 5 | 5 |
| 421 | 5 | 5 | 5 | 5 |

TABLE 54

| Compound Nos. | Herbicidal effects | | | |
|---|---|---|---|---|
| | Po | Am | Ch | Ci |
| 423 | 5 | 5 | 5 | 5 |
| 424 | 5 | 5 | 5 | 5 |
| 427 | 5 | 5 | 5 | 5 |
| 432 | 5 | 5 | 5 | 5 |
| 433 | 5 | 5 | 5 | 5 |
| 435 | 5 | 5 | 5 | 5 |
| 436 | 5 | 5 | 5 | 5 |
| 439 | 5 | 5 | 5 | 5 |
| 440 | 5 | 5 | 5 | 5 |
| 441 | 5 | 5 | 5 | 5 |
| 442 | 5 | 5 | 5 | 5 |
| 443 | 5 | 5 | 5 | 5 |
| 444 | 5 | 5 | 5 | 5 |
| 445 | 5 | 5 | 5 | 5 |
| 446 | 5 | 5 | 5 | 5 |
| 447 | 5 | 5 | 5 | 5 |
| 448 | 5 | 5 | 5 | 5 |
| 449 | 5 | 5 | 5 | 5 |
| 450 | 5 | 5 | 5 | 5 |

TABLE 54-continued

| Compound Nos. | Herbicidal effects | | | |
|---|---|---|---|---|
| | Po | Am | Ch | Ci |
| 451 | 5 | 5 | 5 | 5 |
| 452 | 5 | 5 | 5 | 5 |
| 453 | 5 | 5 | 5 | 5 |
| 454 | 5 | 5 | 5 | 5 |
| 455 | 5 | 5 | 5 | 5 |
| 456 | 5 | 5 | 5 | 5 |
| 457 | 5 | 5 | 5 | 5 |
| 458 | 5 | 5 | 5 | 5 |
| 459 | 5 | 5 | 5 | 5 |
| 460 | 5 | 5 | 5 | 5 |

TABLE 55

| Compound Nos. | Herbicidal effects | | | |
|---|---|---|---|---|
| | Po | Am | Ch | Ci |
| 461 | 5 | 5 | 5 | 5 |
| 462 | 5 | 5 | 5 | 5 |
| 463 | 5 | 5 | 5 | 5 |
| 464 | 5 | 5 | 5 | 5 |
| 466 | 5 | 5 | 5 | 5 |
| 467 | 5 | 5 | 5 | 5 |
| 468 | 5 | 5 | 5 | 5 |
| 469 | 5 | 5 | 5 | 5 |
| 470 | 5 | 5 | 5 | 5 |
| 471 | 5 | 5 | 5 | 5 |
| 472 | 5 | 5 | 5 | 5 |
| 473 | 5 | 5 | 5 | 5 |
| 476 | 5 | 5 | 5 | 5 |
| 479 | 5 | 5 | 5 | 5 |
| 482 | 5 | 5 | 5 | 5 |
| 483 | 5 | 5 | 5 | 5 |
| 484 | 5 | 5 | 5 | 5 |
| 508 | 5 | 5 | 5 | 5 |
| 510 | 5 | 5 | 5 | 5 |
| 511 | 5 | 5 | 5 | 5 |
| 513 | 5 | 5 | 5 | 5 |
| 515 | 5 | 5 | 5 | 5 |
| 521 | 5 | 5 | 5 | 5 |
| 524 | 5 | 5 | 5 | 5 |
| 539 | 5 | 5 | 5 | 5 |
| 571 | 5 | 5 | 5 | 5 |
| 572 | 5 | 5 | 5 | 5 |
| 577 | 5 | 5 | 5 | 5 |
| 578 | 5 | 5 | 5 | 5 |

TABLE 56

| Compound Nos. | Herbicidal effects | | | |
|---|---|---|---|---|
| | Po | Am | Ch | Ci |
| 584 | 5 | 5 | 5 | 5 |
| 591 | 5 | 5 | 5 | 5 |
| 592 | 5 | 5 | 5 | 5 |
| 605 | 5 | 5 | 5 | 5 |
| 606 | 5 | 5 | 5 | 5 |
| 607 | 5 | 5 | 5 | 5 |
| 610 | 5 | 5 | 5 | 5 |
| 612 | 5 | 5 | 5 | 5 |
| 617 | 5 | 5 | 5 | 5 |
| 618 | 5 | 5 | 5 | 5 |
| 619 | 5 | 5 | 5 | 5 |
| 622 | 5 | 5 | 5 | 5 |
| 623 | 5 | 5 | 5 | 5 |
| 624 | 5 | 5 | 5 | 5 |
| 630 | 5 | 5 | 5 | 5 |
| 631 | 5 | 5 | 5 | 5 |
| 632 | 5 | 5 | 5 | 5 |

TABLE 56-continued

| Compound Nos. | Herbicidal effects | | | |
|---|---|---|---|---|
| | Po | Am | Ch | Ci |
| 634 | 5 | 5 | 5 | 5 |
| 635 | 5 | 5 | 5 | 5 |
| 636 | 5 | 5 | 5 | 5 |
| 639 | 5 | 5 | 5 | 5 |
| 640 | 5 | 5 | 5 | 5 |
| 641 | 5 | 5 | 5 | 5 |
| 643 | 5 | 5 | 5 | 5 |
| 644 | 5 | 5 | 5 | 5 |
| 645 | 5 | 5 | 5 | 5 |
| 646 | 5 | 5 | 5 | 5 |
| 647 | 5 | 5 | 5 | 5 |
| 648 | 5 | 5 | 5 | 5 |

TABLE 57

| Compound Nos. | Herbicidal effects | | | |
|---|---|---|---|---|
| | Po | Am | Ch | Ci |
| 649 | 5 | 5 | 5 | 5 |
| 651 | 5 | 5 | 5 | 5 |
| 653 | 5 | 5 | 5 | 5 |
| 655 | 5 | 5 | 5 | 5 |
| 656 | 5 | 5 | 5 | 5 |
| 657 | 5 | 5 | 5 | 5 |
| 658 | 5 | 5 | 5 | 5 |
| 659 | 5 | 5 | 5 | 5 |
| 660 | 5 | 5 | 5 | 5 |
| 661 | 5 | 5 | 5 | 5 |
| 662 | 5 | 5 | 5 | 5 |
| 663 | 5 | 5 | 5 | 5 |
| 664 | 5 | 5 | 5 | 5 |
| 665 | 5 | 5 | 5 | 5 |
| 666 | 5 | 5 | 5 | 5 |
| 667 | 5 | 5 | 5 | 5 |
| 668 | 5 | 5 | 5 | 5 |
| 669 | 5 | 5 | 5 | 5 |
| 670 | 5 | 5 | 5 | 5 |
| 671 | 5 | 5 | 5 | 5 |
| 672 | 5 | 5 | 5 | 5 |
| 674 | 5 | 5 | 5 | 5 |
| 676 | 5 | 5 | 5 | 5 |
| 677 | 5 | 5 | 5 | 5 |
| 680 | 5 | 5 | 5 | 5 |
| 681 | 5 | 5 | 5 | 5 |
| 682 | 5 | 5 | 5 | 5 |
| 684 | 5 | 5 | 5 | 5 |
| 685 | 5 | 5 | 5 | 5 |

TABLE 58

| Compound Nos. | Herbicidal effects | | | |
|---|---|---|---|---|
| | Po | Am | Ch | Ci |
| 686 | 5 | 5 | 5 | 5 |
| 688 | 5 | 5 | 5 | 5 |
| 698 | 5 | 5 | 5 | 5 |
| 699 | 5 | 5 | 5 | 5 |
| 701 | 5 | 5 | 5 | 5 |
| 702 | 5 | 5 | 5 | 5 |
| 703 | 5 | 5 | 5 | 5 |
| 704 | 5 | 5 | 5 | 5 |
| 705 | 5 | 5 | 5 | 5 |
| 706 | 5 | 5 | 5 | 5 |
| 707 | 5 | 5 | 5 | 5 |
| 708 | 5 | 5 | 5 | 5 |
| 709 | 5 | 5 | 5 | 5 |
| 710 | 5 | 5 | 5 | 5 |
| 711 | 5 | 5 | 5 | 5 |

TABLE 58-continued

| Compound | Herbicidal effects | | | |
|---|---|---|---|---|
| Nos. | Po | Am | Ch | Ci |
| 712 | 5 | 5 | 5 | 5 |
| 724 | 5 | 5 | 5 | 5 |
| 725 | 5 | 5 | 5 | 5 |
| 726 | 5 | 5 | 5 | 5 |
| 727 | 5 | 5 | 5 | 5 |
| 730 | 5 | 5 | 5 | 5 |

Test Example 4

(Test on crop plant selectivity by upland field soil treatment)

In a plastic pot (surface area: 600 cm$^2$) filled with sand, wheat (Tr), pale smartweed (Po), slender amaranth (Am), common lambsquarters (Ch) and velvetleaf (Ab) were sown and covered with soil. Next day, a prescribed amount of the active ingredient ($g^{ai}$/10a) of a wettable powder prepared in accordance with Formulation Example 1 was diluted with water and applied uniformly to the soil surface by a small-sized sprayer in an amount of 100 lit. per 10 ares. The plants were then cultured in a green house, and the evaluation of the herbicidal effects and phytotoxicity was conducted on the 21st day after the application in accordance with the standards as identified in Table 31. The results are shown in Tables 59–62. Symbol—represents "not tested".

TABLE 59

| Compound | Dose ai, g | Herbicidal effects | | | | Phytotoxicity |
|---|---|---|---|---|---|---|
| Nos. | /10a | Po | Am | Ch | Ab | Tr |
| 3 | 1.6 | 5 | 5 | 5 | 5 | 0 |
| 6 | 1.6 | 5 | 5 | 5 | 5 | 1 |
| 8 | 1.6 | 5 | 5 | 5 | 5 | 1 |
| 13 | 1.6 | 5 | 5 | 5 | 5 | 0 |
| 15 | 1.6 | 5 | 5 | 5 | 5 | 0 |
| 22 | 1.6 | 5 | 5 | 5 | 5 | 0 |
| 23 | 1.6 | 5 | 5 | 5 | 5 | 1 |
| 31 | 1.6 | 5 | 5 | 5 | 5 | 1 |
| 33 | 1.6 | 5 | 5 | 5 | 5 | 1 |
| 70 | 1.6 | 5 | 5 | 5 | 5 | 1 |
| 71 | 1.6 | 5 | 5 | 5 | 5 | 1 |
| 72 | 1.6 | 5 | 5 | 5 | 5 | 0 |
| 78 | 1.6 | 5 | 5 | 5 | 5 | 1 |
| 84 | 6.3 | 5 | 5 | 5 | 5 | 1 |
| 95 | 1.6 | 5 | 5 | 5 | 5 | 1 |
| 98 | 6.3 | 5 | 5 | 5 | 5 | 1 |
| 111 | 1.6 | 5 | 5 | 5 | 5 | 1 |
| 142 | 6.3 | 5 | 5 | 5 | 5 | 1 |
| 152 | 1.6 | 5 | 5 | 4 | 5 | 0 |
| 153 | 6.3 | 5 | 5 | 5 | 5 | 1 |
| 165 | 1.6 | 5 | 5 | 5 | 5 | 1 |
| 200 | 1.6 | 5 | 5 | 5 | 5 | 1 |
| 222 | 1.6 | 5 | 5 | 5 | 5 | 0 |
| 233 | 1.6 | 5 | 5 | 5 | 5 | 1 |
| 245 | 6.3 | 5 | 5 | 5 | 5 | 0 |
| 246 | 1.6 | 5 | 5 | 5 | 5 | 0 |
| 247 | 6.3 | 5 | 5 | 5 | 5 | 0 |
| 266 | 6.3 | 5 | 5 | 5 | 5 | 1 |
| 289 | 1.6 | 5 | 5 | 5 | 5 | 1 |

TABLE 60

| Compound | Dose ai, g | Herbicidal effects | | | | Phytotoxicity |
|---|---|---|---|---|---|---|
| Nos. | /10a | Po | Am | Ch | Ab | Tr |
| 374 | 1.6 | 5 | 5 | 5 | 5 | 1 |
| 379 | 1.6 | 5 | 5 | 5 | 5 | 1 |
| 383 | 1.6 | 5 | 5 | 5 | 5 | 1 |
| 392 | 1.6 | 5 | 5 | 4 | 5 | 1 |
| 394 | 1.6 | 5 | 5 | 5 | 5 | 1 |
| 397 | 1.6 | 5 | 5 | 5 | 5 | 1 |
| 398 | 1.6 | 5 | 5 | 5 | 4 | 1 |
| 402 | 6.3 | 5 | 5 | 5 | 5 | 1 |
| 406 | 1.6 | 5 | 5 | 5 | 5 | 1 |
| 407 | 1.6 | 5 | 5 | 5 | 5 | 1 |
| 409 | 1.6 | 5 | 5 | 5 | 5 | 1 |
| 410 | 1.6 | 5 | 5 | 5 | 5 | 1 |
| 411 | 1.6 | 5 | 5 | 5 | 5 | 1 |
| 417 | 1.6 | 5 | 5 | 5 | 5 | 1 |
| 421 | 1.6 | 5 | 5 | 5 | 5 | 1 |
| 423 | 1.6 | 5 | 5 | 5 | 5 | 1 |
| 432 | 1.6 | 5 | 5 | 5 | 5 | 1 |
| 435 | 6.3 | 5 | 5 | 5 | 5 | 1 |
| 436 | 1.6 | 5 | 5 | 5 | 5 | 1 |
| 439 | 1.6 | 5 | 5 | 5 | 5 | 1 |
| 440 | 1.6 | 5 | 5 | 5 | 5 | 1 |
| 441 | 1.6 | 5 | 5 | 5 | 5 | 1 |
| 444 | 6.3 | 5 | 5 | 5 | 5 | 1 |
| 447 | 6.3 | 5 | 5 | 5 | 5 | 1 |
| 448 | 6.3 | 5 | 5 | 5 | 5 | 1 |
| 454 | 1.6 | 5 | 5 | 5 | 5 | 1 |
| 458 | 1.6 | 5 | 5 | 5 | 5 | 0 |
| 459 | 1.6 | 5 | 5 | 5 | 5 | 1 |
| 462 | 1.6 | 5 | 5 | 5 | 5 | 1 |

TABLE 61

| Compound | Dose ai, g | Herbicidal effects | | | | Phytotoxicity |
|---|---|---|---|---|---|---|
| Nos. | /10a | Po | Am | Ch | Ab | Tr |
| 467 | 1.6 | 5 | 5 | 5 | 5 | 1 |
| 468 | 6.3 | 5 | 5 | 5 | 5 | 1 |
| 471 | 1.6 | 5 | 5 | 5 | 5 | 1 |
| 482 | 1.6 | 5 | 5 | 5 | — | 1 |
| 515 | 1.6 | 5 | 5 | 5 | 5 | 1 |
| 524 | 1.6 | 5 | 5 | 5 | 5 | 1 |
| 539 | 1.6 | 5 | 5 | 5 | 5 | 1 |
| 578 | 1.6 | 5 | 5 | 5 | 5 | 0 |
| 617 | 1.6 | 5 | 5 | 5 | 5 | 1 |
| 619 | 1.6 | 5 | 5 | 5 | 5 | 1 |
| 630 | 6.3 | 4 | 5 | 5 | 5 | 1 |
| 639 | 1.6 | 5 | 5 | 5 | 5 | 0 |
| 648 | 1.6 | 5 | 5 | 5 | 5 | 1 |
| 656 | 1.6 | 5 | 5 | 5 | 5 | 1 |
| 658 | 1.6 | 5 | 5 | 5 | 5 | 0 |
| 661 | 1.6 | 5 | 5 | 5 | 5 | 1 |
| 662 | 1.6 | 5 | 5 | 5 | 5 | 1 |
| 665 | 1.6 | 5 | 4 | 5 | 4 | 1 |
| 667 | 1.6 | 5 | 5 | 5 | 5 | 1 |
| 668 | 1.6 | 5 | 5 | 5 | 5 | 1 |
| 669 | 1.6 | 5 | 5 | 5 | 5 | 1 |
| 672 | 6.3 | 5 | 5 | 5 | 5 | 1 |
| 677 | 6.3 | 5 | 5 | — | 5 | 1 |
| 682 | 1.6 | 5 | 5 | 5 | 5 | 1 |
| 699 | 6.3 | 5 | 5 | 5 | 4 | 1 |
| 702 | 6.3 | 5 | 5 | 5 | 5 | 1 |
| 705 | 1.6 | 5 | 5 | — | 5 | 1 |
| 708 | 1.6 | 5 | 5 | 5 | 5 | 0 |
| 724 | 1.6 | 5 | 5 | 5 | 5 | 1 |

TABLE 62

| Compound Nos. | Dose ai, g /10a | Herbicidal effects | | | | Phytotoxicity |
|---|---|---|---|---|---|---|
| | | Po | Am | Ch | Ab | Tr |
| Comparative 1 | 1.6 | 5 | 5 | 5 | 5 | 5 |
| Comparative 2 | 1.6 | 5 | 5 | 5 | 5 | 5 |

Test Example 5

(Test on crop plant selectivity by upland field soil treatment)

In a plastic pot (surface area: 600 cm²) filled with sand, soybean (Gl), pale smartweed (Po), slender amaranth (Am), common lambsquarters (Ch) and velvetleaf (Ab) were sown and covered with soil. Next day, a prescribed amount of the active ingredient ($g^{ai}$/10a) of a wettable powder prepared in accordance with Formulation Example 1 was diluted with water and applied uniformly to the soil surface by a small-sized sprayer in an amount of 100 lit. per 10 ares. The plants were then cultured in a green house, and the evaluation of the herbicidal effects and phytotoxicity was conducted on the 21st day after the application in accordance with the standards as identified in Table 31. The results are shown in Tables 63–64. Symbol—represents "not tested".

TABLE 63

| Compound Nos. | Dose ai, g 10a | Herbicidal effects | | | | Phytotoxicity |
|---|---|---|---|---|---|---|
| | | Po | Am | Ch | Ab | Gl |
| 4 | 1.6 | 5 | 5 | 5 | 5 | 1 |
| 6 | 1.6 | 5 | 5 | 5 | 5 | 1 |
| 7 | 1.6 | 5 | 5 | 5 | 4 | 0 |
| 31 | 1.6 | 5 | 5 | 5 | 5 | 1 |
| 70 | 1.6 | 5 | 5 | 5 | 5 | 0 |
| 71 | 1.6 | 5 | 5 | 5 | 5 | 1 |
| 72 | 1.6 | 5 | 5 | 5 | 5 | 0 |
| 152 | 1.6 | 5 | 5 | 4 | 5 | 1 |
| 201 | 6.3 | 5 | 5 | 5 | 5 | 0 |
| 207 | 1.6 | 5 | 5 | 5 | 5 | 1 |
| 233 | 6.3 | 5 | 5 | 5 | 5 | 1 |
| 239 | 6.3 | 5 | 5 | 5 | 5 | 1 |
| 266 | 6.3 | 5 | 5 | 5 | 5 | 0 |
| 397 | 1.6 | 5 | 5 | 5 | 5 | 1 |
| 398 | 1.6 | 5 | 5 | 5 | 4 | 1 |
| 421 | 1.6 | 5 | 5 | 5 | 5 | 1 |
| 435 | 6.3 | 5 | 5 | 5 | 5 | 1 |
| 436 | 1.6 | 5 | 5 | 5 | 5 | 1 |
| 439 | 1.6 | 5 | 5 | 5 | 5 | 1 |
| 441 | 1.6 | 5 | 5 | 5 | 5 | 1 |
| 447 | 6.3 | 5 | 5 | 5 | 5 | 1 |
| 450 | 6.3 | 5 | 5 | 5 | 5 | 1 |
| 458 | 1.6 | 5 | 5 | 5 | 5 | 0 |
| 459 | 1.6 | 5 | 5 | 5 | 5 | 1 |
| 463 | 6.3 | 5 | 5 | 5 | 5 | 1 |
| 618 | 1.6 | 5 | 5 | 5 | 5 | 0 |
| 630 | 6.3 | 4 | 5 | 5 | 5 | 1 |
| 639 | 1.6 | 5 | 5 | 5 | 5 | 1 |
| 655 | 6.3 | 5 | 5 | 5 | 5 | 1 |

TABLE 64

| Compound Nos. | Dose ai, g 10a | Herbicidal effects | | | | Phytotoxicity |
|---|---|---|---|---|---|---|
| | | Po | Am | Ch | Ab | Gl |
| 656 | 1.6 | 5 | 5 | 5 | 5 | 0 |
| 658 | 1.6 | 5 | 5 | 5 | 5 | 0 |
| 661 | 1.6 | 5 | 5 | 5 | 5 | 1 |
| 662 | 1.6 | 5 | 5 | 5 | 5 | 1 |
| 665 | 1.6 | 5 | 4 | 5 | 4 | 0 |
| 667 | 1.6 | 5 | 5 | 5 | 5 | 1 |
| 668 | 1.6 | 5 | 5 | 5 | 5 | 1 |
| 669 | 1.6 | 5 | 5 | 5 | 5 | 0 |
| 680 | 1.6 | 5 | 5 | — | 4 | 1 |
| 702 | 6.3 | 5 | 5 | 5 | 5 | 1 |
| 707 | 1.6 | 5 | 5 | 5 | 5 | 1 |
| 708 | 1.6 | 5 | 5 | 5 | 5 | 0 |
| 724 | 1.6 | 5 | 5 | 5 | 5 | 1 |
| Comparative 1 | 6.3 | 5 | 5 | 5 | 5 | 5 |
| Comparative 1 | 1.6 | 5 | 5 | 5 | 5 | 5 |
| Comparative 2 | 6.3 | 5 | 5 | 5 | 5 | 5 |
| Comparative 2 | 1.6 | 5 | 5 | 5 | 5 | 5 |

Test Example 6

(Test on crop plant selectivity by upland field soil treatment)

In a plastic pot (surface area: 600 cm²) filled with sand, corn (Ze), pale smartweed (Po), slender amaranth (Am), common lambsquarters (Ch) and velvetleaf (Ab) were sown and covered with soil. Next day, a prescribed amount of the active ingredient ($g^{ai}$/10a) of a wettable powder prepared in accordance with Formulation Example 1 was diluted with water and applied uniformly to the soil surface by a small-sized sprayer in an amount of 100 lit. per 10 ares. The plants were then cultured in a green house, and the evaluation of the herbicidal effects and phytotoxicity was conducted on the 21st day after the application in accordance with the standards as identified in Table 31. The results are shown in Tables 65–66. Symbol - represents "not tested".

TABLE 65

| Compound Nos. | Dose ai, g 10a | Herbicidal effects | | | | Phytotoxicity |
|---|---|---|---|---|---|---|
| | | Po | Am | Ch | Ab | Ze |
| 3 | 1.6 | 5 | 5 | 5 | 5 | 0 |
| 6 | 1.6 | 5 | 5 | 5 | 5 | 0 |
| 7 | 1.6 | 5 | 5 | 5 | 4 | 0 |
| 43 | 1.6 | 5 | 5 | 5 | 5 | 0 |
| 70 | 1.6 | 5 | 5 | 5 | 5 | 0 |
| 72 | 1.6 | 5 | 5 | 5 | 5 | 0 |
| 152 | 1.6 | 5 | 5 | 4 | 5 | 1 |
| 239 | 6.3 | 5 | 5 | 5 | 5 | 1 |
| 246 | 1.6 | 5 | 5 | 5 | 5 | 0 |
| 266 | 6.3 | 5 | 5 | 5 | 5 | 0 |
| 374 | 1.6 | 5 | 5 | 5 | 5 | 1 |
| 397 | 1.6 | 5 | 5 | 5 | 5 | 1 |
| 406 | 1.6 | 5 | 5 | 5 | 5 | 1 |
| 432 | 1.6 | 5 | 5 | 5 | 5 | 1 |
| 441 | 1.6 | 5 | 5 | 5 | 5 | 1 |
| 454 | 1.6 | 5 | 5 | 5 | 5 | 1 |
| 458 | 1.6 | 5 | 5 | 5 | 5 | 1 |
| 515 | 1.6 | 5 | 5 | 5 | 5 | 1 |
| 524 | 1.6 | 5 | 5 | 5 | 5 | 1 |
| 618 | 1.6 | 5 | 5 | 5 | 5 | 1 |
| 630 | 6.3 | 4 | 5 | 5 | 5 | 1 |
| 658 | 1.6 | 5 | 5 | 5 | 5 | 1 |
| 661 | 1.6 | 5 | 5 | 5 | 5 | 1 |
| 665 | 1.6 | 5 | 4 | 5 | 4 | 1 |
| 699 | 6.3 | 5 | 5 | 5 | 4 | 1 |
| 705 | 1.6 | 5 | 5 | - | 5 | 1 |

TABLE 65-continued

| Compound Nos. | Dose ai, g 10a | Herbicidal effects Po | Am | Ch | Ab | Phytotoxicity Ze |
|---|---|---|---|---|---|---|
| 708 | 1.6 | 5 | 5 | 5 | 5 | 0 |
| Comparative 1 | 6.3 | 5 | 5 | 5 | 5 | 5 |
| | 1.6 | 5 | 5 | 5 | 5 | 5 |

TABLE 66

| Compound Nos. | Dose ai, g 10a | Herbicidal effects Po | Am | Ch | Ab | Phytotoxicity Ze |
|---|---|---|---|---|---|---|
| Comparative 2 | 6.3 | 5 | 5 | 5 | 5 | 5 |
| | 1.6 | 5 | 5 | 5 | 5 | 5 |

Test Example 7

(Test on crop plant selectivity by upland field soil treatment)

In a plastic pot (surface area: 600 cm$^2$) filled with sand, cotton (Go), pale smartweed (Po), slender amaranth (Am), common lambsquarters (Ch) and velvetleaf (Ab) were sown and covered with soil. Next day, a prescribed amount of the active ingredient (g$^{ai}$/10a) of a wettable powder prepared in accordance with Formulation Example 1 was diluted with water and applied uniformly to the soil surface by a small-sized sprayer in an amount of 100 lit. per 10 ares. The plants were then cultured in a green house, and the evaluation of the herbicidal effects and phytotoxicity was conducted on the 21st day after the application in accordance with the standards as identified in Table 31. The results are shown in Tables 67–69. Symbol—represents "not tested".

TABLE 67

| Compound Nos. | Dose ai, g 10a | Herbicidal effects Po | Am | Ch | Ab | Phytotoxicity Go |
|---|---|---|---|---|---|---|
| 3 | 1.6 | 5 | 5 | 5 | 5 | 0 |
| 7 | 1.6 | 5 | 5 | 5 | 4 | 0 |
| 10 | 1.6 | 5 | 5 | 5 | 5 | 1 |
| 15 | 1.6 | 5 | 5 | 5 | 5 | 1 |
| 30 | 1.6 | 5 | 5 | 5 | 5 | 0 |
| 31 | 1.6 | 5 | 5 | 5 | 5 | 0 |
| 33 | 1.6 | 5 | 5 | 5 | 5 | 1 |
| 70 | 1.6 | 5 | 5 | 5 | 5 | 0 |
| 71 | 1.6 | 5 | 5 | 5 | 5 | 0 |
| 72 | 1.6 | 5 | 5 | 5 | 5 | 1 |
| 111 | 1.6 | 5 | 5 | 5 | 5 | 1 |
| 147 | 1.6 | 5 | 5 | 5 | 5 | 1 |
| 152 | 1.6 | 5 | 5 | 4 | 5 | 0 |
| 153 | 6.3 | 5 | 5 | 5 | 5 | 0 |
| 166 | 6.3 | 5 | 5 | 5 | 5 | 1 |
| 197 | 1.6 | 5 | 5 | 5 | 5 | 0 |
| 201 | 1.6 | 5 | 5 | 5 | 4 | 0 |
| 233 | 1.6 | 5 | 5 | 5 | 5 | 1 |
| 237 | 6.3 | 5 | 5 | 5 | 5 | 1 |
| 266 | 6.3 | 5 | 5 | 5 | 5 | 1 |
| 272 | 6.3 | 5 | 5 | 5 | 5 | 1 |
| 299 | 1.6 | 5 | 5 | 5 | 5 | 1 |
| 374 | 1.6 | 5 | 5 | 5 | 5 | 1 |
| 383 | 1.6 | 5 | 5 | 5 | 5 | 1 |
| 397 | 1.6 | 5 | 5 | 5 | 5 | 0 |

TABLE 67-continued

| Compound Nos. | Dose ai, g 10a | Herbicidal effects Po | Am | Ch | Ab | Phytotoxicity Go |
|---|---|---|---|---|---|---|
| 398 | 1.6 | 5 | 5 | 5 | 4 | 1 |
| 405 | 1.6 | 5 | 5 | 5 | 5 | 1 |
| 406 | 1.6 | 5 | 5 | 5 | 5 | 1 |

TABLE 68

| Compound Nos. | Dose ai, g 10a | Herbicidal effects Po | Am | Ch | Ab | Phytotoxicity Go |
|---|---|---|---|---|---|---|
| 410 | 1.6 | 5 | 5 | 5 | 5 | 1 |
| 411 | 1.6 | 5 | 5 | 5 | 5 | 0 |
| 417 | 1.6 | 5 | 5 | 5 | 5 | 0 |
| 418 | 1.6 | 5 | 5 | 5 | 5 | 1 |
| 421 | 1.6 | 5 | 5 | 5 | 5 | 1 |
| 424 | 1.6 | 5 | — | 5 | 5 | 1 |
| 432 | 1.6 | 5 | 5 | 5 | 5 | 0 |
| 435 | 6.3 | 5 | 5 | 5 | 5 | 1 |
| 436 | 1.6 | 5 | 5 | 5 | 5 | 0 |
| 442 | 6.3 | 5 | 5 | 5 | 5 | 1 |
| 444 | 6.3 | 5 | 5 | 5 | 5 | 1 |
| 448 | 6.3 | 5 | 5 | 5 | 5 | 1 |
| 454 | 1.6 | 5 | 5 | 5 | 5 | 1 |
| 458 | 1.6 | 5 | 5 | 5 | 5 | 0 |
| 459 | 1.6 | 5 | 5 | 5 | 5 | 1 |
| 463 | 6.3 | 5 | 5 | 5 | 5 | 0 |
| 468 | 6.3 | 5 | 5 | 5 | 5 | 1 |
| 471 | 1.6 | 5 | 5 | 5 | 5 | 1 |
| 515 | 1.6 | 5 | 5 | 5 | 5 | 1 |
| 571 | 6.3 | 4 | 5 | 5 | 5 | 1 |
| 577 | 1.6 | 5 | 4 | 5 | 5 | 1 |
| 578 | 1.6 | 5 | 5 | 5 | 5 | 1 |
| 618 | 1.6 | 5 | 5 | 5 | 5 | 0 |
| 630 | 6.3 | 4 | 5 | 5 | 5 | 1 |
| 631 | 6.3 | 5 | 5 | 5 | 5 | 1 |
| 639 | 1.6 | 5 | 5 | 5 | 5 | 0 |
| 655 | 6.3 | 5 | 5 | 5 | 5 | 0 |
| 656 | 1.6 | 5 | 5 | 5 | 5 | 0 |
| 658 | 1.6 | 5 | 5 | 5 | 5 | 0 |

| Compound Nos. | Dose ai, g 10a | Herbicidal effects Po | Am | Ch | Ab | Phytotoxicity Go |
|---|---|---|---|---|---|---|
| 661 | 1.6 | 5 | 5 | 5 | 5 | 0 |
| 665 | 1.6 | 5 | 4 | 5 | 4 | 0 |
| 666 | 1.6 | 5 | 5 | 5 | 5 | 1 |
| 667 | 1.6 | 5 | 5 | 5 | 5 | 1 |
| 668 | 1.6 | 5 | 5 | 5 | 5 | 0 |
| 669 | 1.6 | 5 | 5 | 5 | 5 | 1 |
| 672 | 6.3 | 5 | 5 | 5 | 5 | 1 |
| 680 | 1.6 | 5 | 5 | — | 4 | 1 |
| 699 | 6.3 | 5 | 5 | 5 | 4 | 1 |
| 702 | 6.3 | 5 | 5 | 5 | 5 | 1 |
| 705 | 1.6 | 5 | 5 | — | 5 | 1 |
| 706 | 1.6 | 5 | 5 | 5 | 5 | 1 |
| 707 | 1.6 | 5 | 5 | 5 | 5 | 1 |
| 708 | 1.6 | 5 | 5 | 5 | 5 | 0 |
| 724 | 1.6 | 5 | 5 | 5 | 5 | 1 |
| Comparative 1 | 6.3 | 5 | 5 | 5 | 5 | 5 |
| | 1.6 | 5 | 5 | 5 | 5 | 5 |
| Comparative 2 | 6.3 | 5 | 5 | 5 | 5 | 5 |
| | 1.6 | 5 | 5 | 5 | 5 | 5 |

Test Example 8

(Test on crop plant selectivity by upland field foliage treatment)

In a plastic pot (surface area: 600 cm$^2$) filled with sand, rice (Or), pale smartweed (Po), slender amaranth (Am), common lambsquarters (Ch) and velvetleaf (Ab) were sown and cultured in a green house for 2 weeks. Then, a prescribed amount of the active ingredient (g$^{ai}$/10a) of a wettable powder prepared in accordance with Formulation Example 1 was diluted with water and applied onto the entire foliages of the plants from above by a small-sized sprayer in an amount of 100 lit. per 10 ares. The plants were then cultured in a green house, and the evaluation of the herbicidal effects and phytotoxicity was conducted on the 14th day after the treatment in accordance with the standards as identified in Table 31. The results are shown in Table 70.

TABLE 70

| Compound Nos. | Dose ai, g 10a | Herbicidal effects | | | | Phytotoxicity |
| --- | --- | --- | --- | --- | --- | --- |
| | | Po | Am | Ch | Ab | Or |
| 6 | 1.6 | 5 | 5 | 5 | 5 | 1 |
| 10 | 1.6 | 5 | 5 | 5 | 5 | 1 |
| 12 | 0.4 | 5 | 5 | 5 | 5 | 1 |
| 33 | 1.6 | 5 | 5 | 5 | 5 | 1 |
| 44 | 0.4 | 4 | 5 | 5 | 5 | 0 |
| 72 | 1.6 | 5 | 5 | 5 | 5 | 1 |
| 78 | 0.4 | 5 | 5 | 5 | 5 | 1 |
| 111 | 0.4 | 5 | 5 | 5 | 5 | 1 |
| 207 | 0.4 | 5 | 5 | 5 | 5 | 1 |
| 228 | 1.6 | 5 | 5 | 5 | 5 | 1 |
| Comparative 1 | 1.6 | 5 | 5 | 5 | 5 | 5 |
| Comparative 1 | 0.4 | 5 | 5 | 5 | 5 | 3 |
| Comparative 2 | 1.6 | 5 | 5 | 5 | 5 | 5 |
| Comparative 2 | 0.4 | 5 | 5 | 5 | 5 | 4 |

Test Example 9

(Test on crop plant selectivity by upland field foliage treatment)

In a plastic pot (surface area: 600 cm$^2$) filled with sand, wheat (Tr), pale smartweed (Po), slender amaranth (Am), common lambsquarters (Ch) and velvetleaf (Ab) were sown and cultured in a green house for 2 weeks. Then, a prescribed amount of the active ingredient (g$^{ai}$/10a) of a wettable powder prepared in accordance with Formulation Example 1 was diluted with water and applied onto the entire foliages of the plants from above by a small-sized sprayer in an amount of 100 lit. per 10 ares. The plants were then cultured in a green house, and the evaluation of the herbicidal effects and phytotoxicity was conducted on the 14th day after the treatment in accordance with the standards as identified in Table 31. The results are shown in Tables 71–73.

TABLE 71

| Compound Nos. | Dose ai, g 10a | Herbicidal effects | | | | Phytotoxicity |
| --- | --- | --- | --- | --- | --- | --- |
| | | Po | Am | Ch | Ab | Tr |
| 1 | 0.4 | 5 | 5 | 5 | 5 | 1 |
| 3 | 0.4 | 5 | 5 | 5 | 5 | 1 |
| 4 | 1.6 | 5 | 5 | 5 | 5 | 1 |
| 10 | 1.6 | 5 | 5 | 5 | 5 | 1 |
| 12 | 0.4 | 5 | 5 | 5 | 5 | 0 |
| 14 | 0.4 | 5 | 5 | 5 | 5 | 1 |
| 22 | 0.4 | 5 | 5 | 5 | 5 | 0 |
| 30 | 1.6 | 5 | 5 | 5 | 5 | 1 |
| 33 | 1.6 | 5 | 5 | 5 | 5 | 1 |
| 35 | 1.6 | 5 | 5 | 5 | 5 | 0 |
| 43 | 1.6 | 5 | 5 | 5 | 5 | 0 |
| 45 | 1.6 | 5 | 5 | 5 | 5 | 1 |
| 70 | 1.6 | 5 | 5 | 5 | 5 | 1 |
| 74 | 1.6 | 5 | 5 | 5 | 5 | 1 |
| 83 | 1.6 | 4 | 5 | 5 | 4 | 1 |
| 95 | 1.6 | 5 | 5 | 5 | 5 | 1 |
| 98 | 0.4 | 4 | 5 | 5 | 5 | 1 |
| 101 | 0.4 | 5 | 5 | 5 | 5 | 1 |
| 111 | 0.4 | 5 | 5 | 5 | 5 | 1 |
| 143 | 0.4 | 5 | 5 | 5 | 5 | 1 |
| 152 | 0.4 | 5 | 5 | 5 | 5 | 0 |
| 153 | 0.4 | 5 | 5 | 5 | 5 | 1 |
| 207 | 0.4 | 5 | 5 | 5 | 5 | 1 |
| 222 | 0.4 | 5 | 5 | 5 | 5 | 1 |
| 272 | 1.6 | 5 | 5 | 5 | 5 | 1 |
| 394 | 0.4 | 5 | 5 | 5 | 5 | 0 |
| 402 | 0.4 | 4 | 5 | 5 | 5 | 1 |
| 405 | 0.4 | 5 | 5 | 5 | 5 | 1 |
| 411 | 1.6 | 4 | 5 | 5 | 5 | 1 |

TABLE 72

| Compound Nos. | Dose ai, g /10a | Herbicidal effects | | | | Phytotoxicity |
| --- | --- | --- | --- | --- | --- | --- |
| | | Po | Am | Ch | Ab | Tr |
| 423 | 1.6 | 5 | 5 | 5 | 5 | 1 |
| 424 | 1.6 | 5 | 5 | 5 | 5 | 1 |
| 432 | 0.4 | 5 | 5 | 5 | 5 | 1 |
| 436 | 1.6 | 5 | 5 | 5 | 5 | 1 |
| 439 | 0.4 | 5 | 5 | 4 | 5 | 1 |
| 447 | 1.6 | 5 | 5 | 4 | 5 | 1 |
| 458 | 0.4 | 5 | 5 | 5 | 5 | 1 |
| 460 | 1.6 | 4 | 5 | 4 | 5 | 1 |
| 462 | 0.4 | 5 | 5 | 5 | 5 | 1 |
| 463 | 0.4 | 5 | 5 | 5 | 4 | 1 |
| 464 | 0.4 | 5 | 5 | 5 | 5 | 1 |
| 467 | 1.6 | 5 | 5 | 5 | 5 | 1 |
| 468 | 0.4 | 4 | 5 | 5 | 4 | 1 |
| 469 | 0.4 | 5 | 5 | 5 | 5 | 1 |
| 482 | 0.4 | 5 | 5 | 5 | 5 | 1 |
| 515 | 0.4 | 5 | 5 | 4 | 5 | 1 |
| 571 | 0.4 | 4 | 5 | 5 | 5 | 1 |
| 572 | 1.6 | 5 | 5 | 5 | 5 | 1 |
| 584 | 0.4 | 5 | 5 | 5 | 5 | 1 |
| 591 | 0.4 | 5 | 5 | 5 | 5 | 1 |
| 592 | 0.4 | 5 | 5 | 5 | 5 | 1 |
| 605 | 1.6 | 4 | 5 | 5 | 5 | 1 |
| 606 | 0.4 | 5 | 5 | 4 | 5 | 1 |
| 607 | 0.4 | 5 | 5 | 4 | 5 | 1 |
| 630 | 1.6 | 5 | 5 | 5 | 5 | 1 |
| 634 | 0.4 | 5 | 5 | 5 | 5 | 1 |
| 635 | 1.6 | 5 | 5 | 5 | 5 | 1 |
| 643 | 1.6 | 5 | 5 | 5 | 4 | 1 |
| 658 | 1.6 | 5 | 5 | 5 | 5 | 1 |

TABLE 73

| Compound Nos. | Dose ai, g /10a | Herbicidal effects | | | | Phytotoxicity |
| --- | --- | --- | --- | --- | --- | --- |
| | | Po | Am | Ch | Ab | Tr |
| 669 | 1.6 | 4 | 5 | 5 | 5 | 1 |
| 670 | 1.6 | 5 | 5 | 5 | 5 | 1 |
| 671 | 1.6 | 5 | 5 | 5 | 5 | 1 |

TABLE 73-continued

| Compound Nos. | Dose ai, g /10a | Herbicidal effects | | | | Phytotoxicity |
|---|---|---|---|---|---|---|
| | | Po | Am | Ch | Ab | Tr |
| 688 | 0.4 | 4 | 5 | 5 | 5 | 1 |
| 706 | 1.6 | 4 | 5 | 5 | 5 | 1 |
| 707 | 0.4 | 5 | 5 | 5 | 5 | 0 |
| 708 | 0.4 | 5 | 5 | 5 | 5 | 1 |
| 712 | 0.4 | 5 | 5 | 5 | 5 | 1 |
| Comparative | 1.6 | 5 | 5 | 5 | 5 | 5 |
| | 0.4 | 5 | 5 | 5 | 5 | 3 |
| Comparative | 1.6 | 5 | 5 | 5 | 5 | 5 |
| | 0.4 | 5 | 5 | 5 | 5 | 3 |

Test Example 10

(Test on crop plant selectivity by upland field foliage treatment)

In a plastic pot (surface area: 600 cm$^2$) filled with sand, corn (Ze), pale smartweed (Po), slender amaranth (Am), common lambsquarters (Ch) and velvetleaf (Ab) were sown and cultured in a green house for 2 weeks. Then, a prescribed amount of the active ingredient (g$^{ai}$/10a) of a wettable powder prepared in accordance with Formulation Example 1 was diluted with water and applied onto the entire foliages of the plants from above by a small-sized sprayer in an amount of 100 lit. per 10 ares. The plants were then cultured in a green house, and the evaluation of the herbicidal effects and phytotoxicity was conducted on the 14th day after the treatment in accordance with the standards as identified in Table 31. The results are shown in Tables 74–75.

TABLE 74

| Compound Nos. | Dose ai, g /10a | Herbicidal effects | | | | Phytotoxicity |
|---|---|---|---|---|---|---|
| | | Po | Am | Ch | Ab | Ze |
| 4 | 0.4 | 5 | 5 | 5 | 4 | 1 |
| 6 | 1.6 | 5 | 5 | 5 | 5 | 1 |
| 7 | 1.6 | 5 | 5 | 5 | 5 | 1 |
| 22 | 0.4 | 5 | 5 | 5 | 5 | 0 |
| 70 | 1.6 | 5 | 5 | 5 | 5 | 1 |
| 72 | 1.6 | 5 | 5 | 5 | 5 | 1 |
| 74 | 1.6 | 5 | 5 | 5 | 5 | 0 |
| 78 | 0.4 | 5 | 5 | 5 | 5 | 0 |
| 83 | 1.6 | 4 | 5 | 5 | 4 | 1 |
| 95 | 1.6 | 5 | 5 | 5 | 5 | 1 |
| 101 | 0.4 | 5 | 5 | 5 | 5 | 1 |
| 111 | 0.4 | 5 | 5 | 5 | 5 | 1 |
| 140 | 1.6 | 5 | 5 | 5 | 5 | 1 |
| 142 | 0.4 | 5 | 5 | 5 | 5 | 1 |
| 152 | 0.4 | 5 | 5 | 5 | 5 | 1 |
| 195 | 1.6 | 4 | 5 | 5 | 5 | 1 |
| 207 | 0.4 | 5 | 5 | 5 | 5 | 1 |
| 222 | 0.4 | 5 | 5 | 5 | 5 | 0 |
| 228 | 1.6 | 5 | 5 | 5 | 5 | 0 |
| 265 | 1.6 | 5 | 5 | 5 | 5 | 1 |
| 272 | 1.6 | 5 | 5 | 5 | 5 | 0 |
| 394 | 0.4 | 5 | 5 | 5 | 5 | 1 |
| 411 | 1.6 | 4 | 5 | 5 | 5 | 1 |
| 423 | 1.6 | 5 | 5 | 5 | 5 | 1 |
| 435 | 0.4 | 5 | 5 | 5 | 5 | 1 |
| 463 | 0.4 | 5 | 5 | 5 | 4 | 1 |
| 464 | 0.4 | 5 | 5 | 5 | 5 | 1 |
| 468 | 0.4 | 4 | 5 | 5 | 4 | 1 |
| 482 | 0.4 | 5 | 5 | 5 | 5 | 1 |

TABLE 75

| Compound Nos. | Dose ai, g /10a | Herbicidal effects | | | | Phytotoxicity |
|---|---|---|---|---|---|---|
| | | Po | Am | Ch | Ab | Ze |
| 515 | 0.4 | 5 | 5 | 4 | 5 | 1 |
| 577 | 0.4 | 5 | 5 | 4 | 5 | 1 |
| 578 | 0.4 | 5 | 5 | 5 | 4 | 1 |
| 584 | 0.4 | 5 | 5 | 5 | 5 | 1 |
| 606 | 0.4 | 5 | 5 | 4 | 5 | 1 |
| 607 | 0.4 | 5 | 5 | 4 | 5 | 1 |
| 617 | 1.6 | 5 | 5 | 5 | 5 | 1 |
| 623 | 0.4 | 5 | 5 | 5 | 5 | 1 |
| 634 | 0.4 | 5 | 5 | 5 | 5 | 1 |
| 635 | 1.6 | 5 | 5 | 5 | 5 | 1 |
| 647 | 0.4 | 5 | 5 | 5 | 5 | 1 |
| 662 | 0.4 | 5 | 5 | 5 | 5 | 1 |
| 663 | 0.4 | 5 | 5 | 5 | 5 | 1 |
| 666 | 1.6 | 5 | 5 | 5 | 5 | 1 |
| 669 | 1.6 | 4 | 5 | 5 | 5 | 1 |
| 671 | 1.6 | 5 | 5 | 5 | 5 | 1 |
| 682 | 1.6 | 5 | 5 | 5 | 5 | 1 |
| 688 | 0.4 | 4 | 5 | 5 | 5 | 1 |
| 706 | 1.6 | 4 | 5 | 5 | 5 | 1 |
| 707 | 0.4 | 5 | 5 | 5 | 5 | 1 |
| 708 | 0.4 | 5 | 5 | 5 | 5 | 1 |
| 712 | 0.4 | 5 | 5 | 5 | 5 | 1 |
| 724 | 1.6 | 5 | 5 | 5 | 5 | 1 |
| 725 | 1.6 | 5 | 5 | 5 | 5 | 1 |
| Comparative 1 | 1.6 | 5 | 5 | 5 | 5 | 5 |
| | 0.4 | 5 | 5 | 5 | 5 | 4 |
| Comparative 2 | 1.6 | 5 | 5 | 5 | 5 | 5 |
| | 0.4 | 5 | 5 | 5 | 5 | 3 |

Test Example 11

(Test on crop plant selectivity by upland field foliage treatment)

In a plastic pot (surface area: 600 cm$^2$) filled with sand, soybean (Gl), slender amaranth (Am) and velvetleaf (Ab) were sown and cultured in a green house for 2 weeks. Then, a prescribed amount of the active ingredient (g$^{ai}$/10a) of a wettable powder prepared in accordance with Formulation Example 1 was diluted with water and applied onto the entire foliages of the plants from above by a small-sized sprayer in an amount of 100 lit. per 10 ares. The plants were then cultured in a green house, and the evaluation of the herbicidal effects and phytotoxicity was conducted on the 14th day after the treatment in accordance with the standards as identified in Table 31. The results are shown in Table 76.

| Compound Nos. | Dose ai, g/10a | Herbicidal effects | | Phytotoxicity |
|---|---|---|---|---|
| | | Am | Ab | Gl |
| 7 | 1.6 | 5 | 5 | 1 |
| 8 | 1.6 | 5 | 5 | 1 |
| 74 | 1.6 | 5 | 5 | 0 |
| 463 | 0.4 | 5 | 4 | 1 |
| 464 | 0.4 | 5 | 5 | 1 |
| 468 | 0.4 | 5 | 4 | 1 |
| 635 | 0.4 | 5 | 5 | 1 |
| 669 | 0.4 | 4 | 5 | 1 |
| 686 | 0.4 | 5 | 5 | 1 |
| 701 | 1.6 | 5 | 4 | 1 |
| 726 | 0.4 | 5 | 5 | 1 |
| Comparative 1 | 1.6 | 5 | 5 | 5 |
| | 0.4 | 5 | 5 | 5 |
| Comparative 2 | 1.6 | 5 | 5 | 5 |
| | 0.4 | 5 | 5 | 5 |

Test Example 12
(Test on crop plant selectivity by upland field foliage treatment)

In a plastic pot (surface area: 600 cm$^2$) filled with sand, cotton (Go), pale smartweed (Po), slender amaranth (Am), common lambsquarters (Ch) and velvetleaf (Ab) were sown and covered with soil. Next day, a prescribed amount of the active ingredient (g$^{ai}$/10a) of a wettable powder prepared in accordance with Formulation Example 1 was diluted with water and applied uniformly to the soil surface by a small-sized sprayer in an amount of 100 lit. per 10 ares. The plants were then cultured in a green house, and the evaluation of the herbicidal effects and phytotoxicity was conducted on the 21st day after the treatment in accordance with the standards as identified in Table 31. The results are shown in Table

TABLE 77

| Compound Nos. | Dose ai, g /10a | Herbicidal effects | | | | Phytotoxicity |
| --- | --- | --- | --- | --- | --- | --- |
| | | Po | Am | Ch | Ab | Go |
| 666 | 1.6 | 5 | 5 | 5 | 5 | 1 |
| Comparative 1 | 1.6 | 5 | 5 | 5 | 5 | 5 |
| Comparative 2 | 1.6 | 5 | 5 | 5 | 5 | 5 |

What is claimed is:

1. A benzofran-7-yl uracil compound having the formula (1):

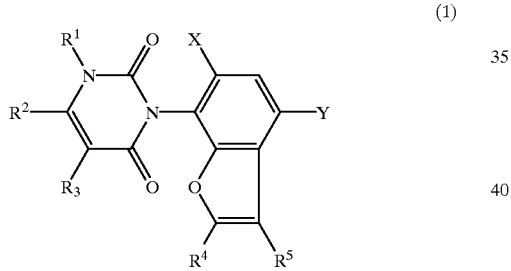

wherein

X is hydrogen or halogen;

Y is hydrogen, halogen, cyano, lower alkyl, lower haloalkyl, lower alkoxy or lower haloalkoxy;

R$^1$ is hydrogen, lower alkyl, amino or lower haloalkyl;

R$^2$ is lower alkyl or lower haloalkyl;

R$^3$ is hydrogen, halogen, lower alkyl or lower haloalkyl;

R$^5$ is hydrogen, lower alkyl, lower cycloalkyl, lower alkenyl, lower alkynyl, lower haloalkyl, lower alkoxy, lower haloalkoxy, lower alkenyloxy, lower alkynyloxy, lower alkoxycarbonylalkoxy, lower alkylthio, lower haloalkylthio, lower alkenylthio, lower alkynylthio, lower alkoxycarbonylalkylthio, lower alkylsulfonyl, lower haloalkylsulfonyl, phenylsulfonyl which is optionally substituted by halogen, halogen, hydroxyiminoalkyl, hydroxyiminohaloalkyl, lower alkoxyiminoalkyl, lower alkoxyiminohaloalkyl, lower alkyliminoalkyl, phenyliminoalkyl, hydrazonalkyl, lower alkylhydrazonoalkyl, phenylhydrazonoalkyl, cyano, carbamoyl having the same or different hydrogen atoms, lower alkyl, lower acyl, haloalkylcarbonyl, lower alkylsulfonyl, haloalkylsulfonyl or phenyl which is optionally substituted by alkyl, alkoxy or halogen, each of said carbamoyl substituents being on the nitrogen atom; phenyl which is optionally substituted by halogen, benzyl which is optionally substituted by alkyl, cyanoalkyl, carbamoylalkyl, thiocyanoalkyl, nitro, hydroxyamino, oxiranyl which is optionally substituted by alkyl; amino having the same or different hydrogen atoms, lower alkyl, haloalkyl, lower alkenyl, lower alkynyl, lower cycloalkyl, alkylsulfonyl, haloalkylsulfonyl, phenylsulfonyl which is optionally substituted by alkyl, alkoxy or halogen, acyl, haloalkylcarbonyl or benzoyl which is optionally substituted, by alkyl, alkoxy or halogen, each of said amino substituents being on the nitrogen atom, or a group of the formula:

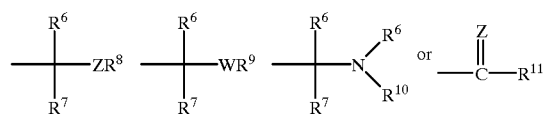

wherein Z is an oxygen atom or a sulfur atom, W is a group of the formula —SO— or a group of the formula —SO$_2$—;

R$^6$ is hydrogen or lower alkyl;

R$^7$ is hydrogen, lower alkyl, lower cycloalkyl, lower alkenyl, lower alkynyl, haloalkyl, lower alkoxyalkyl or lower alkylthioalkyl; or R$^6$ and R$^7$ bond to each other to form a 3- to 8-membered (carbon) ring together with the carbon atom to which they are bonded;

R$^8$ is a hydrogen atom, lower alkyl, lower cycloalkyl, lower haloalkyl, lower alkoxycarbonylalkyl, hydroxycarbonylalkyl, monoalkylcarbamoylalalkyl, dialkylcarbamoylalkyl, lower acyl, lower alkylsulfonyl, haloalkylsulfonyl, haloalkylcarbonyl, monoalkylcarbamoyl, monoalkylthiocarbamoyl, dialkylcarbamoyl, dialkylthiocarbamoyl or benzoyl;

R$^9$ is a hydrogen atom, lower alkyl, lower cycloalkyl, lower haloalkyl, lower alkoxycarbonylalkyl, hydroxycarbonylalkyl, monoalkylcarbamoylalkyl or dialkylcarbamoylalkyl;

R$^{10}$ is a hydrogen atom, lower alkyl, lower acyl, alkylsulfonyl, haloalkylsulfonyl or haloalkylcarbonyl, R$^{11}$ is a hydrogen atom, lower alkyl, lower cycloalkyl, lower alkenyl, lower alkynyl, haloalkyl, lower alkoxyalkyl, alkylthioalkyl, phenyl which is optionally substituted by halogen, alkoxy, haloalkoxy, benzyloxy which is optionally substituted by halogen, phenoxy which is optionally substituted by alkoxy, or hydroxyl; and R$^4$ is selected from the group consisting of hydrogen, methyl, ethyl, n-propyl, isopropyl, n-butyl, isobutyl, bromomethyl, dibromomethyl, tribromomethyl, difluoromethyl, hydroxymethyl,

—CH(CH$_3$)OH, —CH$_2$OCH$_3$, —CH$_2$OC$_2$H$_5$, —CH$_2$OC$_2$H$_5$,

—CH$_2$OCOCH$_3$, —CH$_2$OCOC$_2$H$_5$, —CH(CH$_3$)OCOCH$_3$,

107

—CH₂OCO—⟨phenyl⟩,

—CH₂SCH₃, —CH₂SO₂CH₃,
—CH₂SC₂H₅, —CH₂SO₂C₂H₅, —CH₂N(CH₃)₂,
—CH₂N(C₂H₅)₂, Cl, Br, —COCH₃, —COC₂H₅,
—CH₂N(C₂H₅)₂, Cl, Br, —COCH₃, —COC₂H₅,
—COC₃H₇, —COC₃H₇-i,

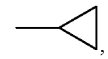

—CHO,
—C(CH₃)=NOH, —C(CH₃)=NOCH₃,
—C(CH₃)=NOC₂H₅, —C(CH₃)=NCH₃,
—C(CH₃)=NNHCH₃, —CN, —COOH, —COOCH₃,
—COOC₂H₅, —COOC₃H₇-i, —COOC₅—H₁₁,

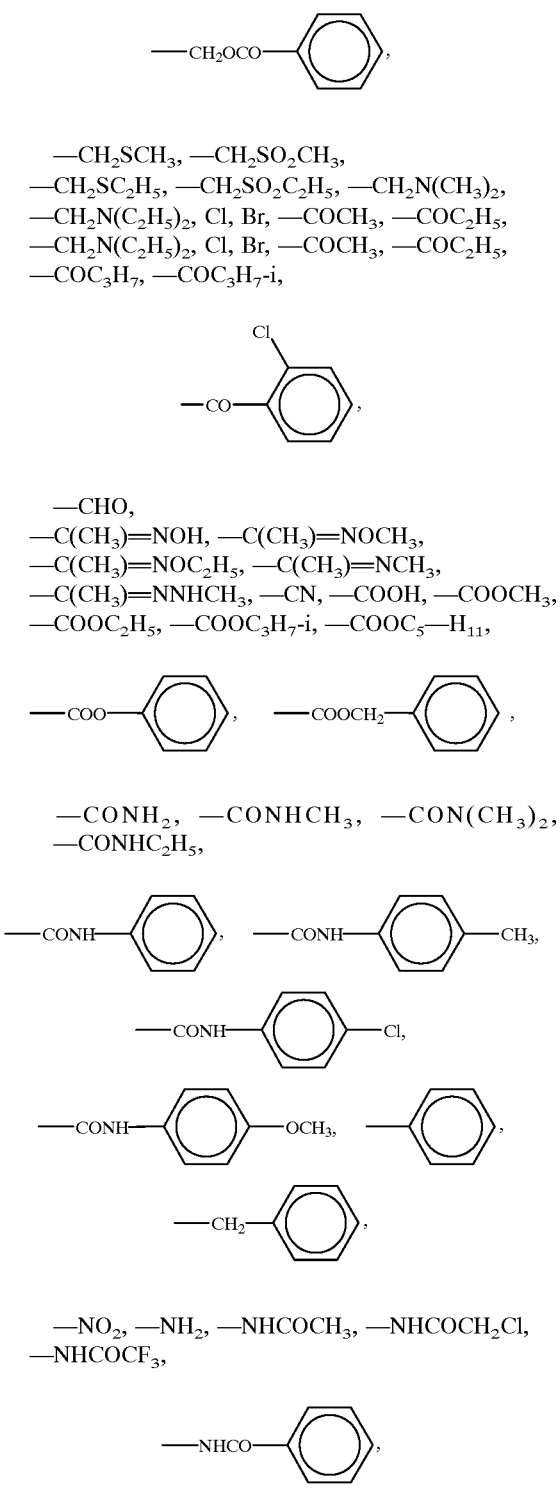

—CONH₂, —CONHCH₃, —CON(CH₃)₂,
—CONHC₂H₅,

—NO₂, —NH₂, —NHCOCH₃, —NHCOCH₂Cl,
—NHCOCF₃,

—NHSO₂CH₃—, —NHSO₂CF₃, —NHSO₂CH₂Cl,

108

—NHSO₂CHF₂,

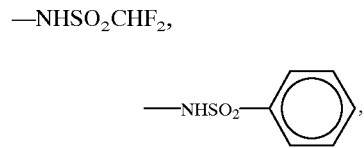

—CH₂N(C₂H₅)₂, —CH(CH₃)Cl, —CH(CH₃)Br,
—CH(CH₃)OCH₃, —CH(C₂H₅)Cl,

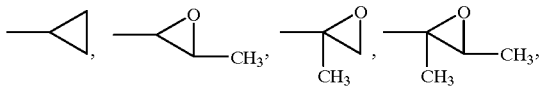

—COC₄H₉-n, —COCH₂Cl, —COCH₂Br,
—COCH₂Cl,
—COCH₂Br, —CH(OH)C₂H₅, —CH(OH)C₃H₇,
—CH(OH)C₃H₇-i, —CH(OH)C≡CH,
—CH(OH)CH=CH₂, —CH₂SC₃H₇, —CH₂SO₂C₃H₇,
—CH₂SC₃H₇-i, —CH₂SO₂C₃H₇-i, —CH₂SC₄H₉,
—CH₂SO₂C₄H₉, —CH=CH₂, —C≡CH,
—CH₂SO₂CH₂CF₃,

CH=CHCH₃,
C(CH₃)=CH₂, C(CH₃)=CHCH₃, C(C₂H₅)=CH₂,
C(C₂H₅)=CHCH₃,
C(CH₃)=C(CH₃)₂, CH=C(CH₃)₂, CH(CH₃)
₅CH₂CF₃, CH(C₂H₅)OCH₃,
CH(CH₃)OCH₂CH₂F, CH(CH=CH₂)OCH₂CF₃, and
CH(CH₃)SCSN(C₂H₅)₂.

2. The benzofiran-7-yl uracil compound of claim 1, wherein X is fluorine or chlorine.

3. The benzofuran-7-yl uracil compound of claim 1, wherein Y is fluorine, chlorine or bromine.

4. The benzofuran-7-yl uracil compound of claim 1, wherein $R^1$ is methyl, amino, ethyl, propyl, chloromethyl or difluoromethyl.

5. The benzofuran-7-yl uracil compound of claim 1, wherein $R^2$ is trifluoromethyl or chloromethyl.

6. The benzofuran-7-yl uracil compound of claim 1, wherein $R^3$ is hydrogen, methyl, chloromethyl or chloro.

7. The benzofuran-7-yl uracil compound of claim 1, wherein $R^5$ is hydrogen, lower alkyl, halogen, cyano, nitro, amino, carboxyl, or hydroxymethyl.

8. A herbicide composition, comprising an amount of one or more benzofuran-7-yl uracil compounds of claim 1, and a carrier.

9. A method of controlling weed growth, which comprises applying a herbicidally effective amount of one or more of the compounds of claim 1 to a soil area either before or during a growing stage in said soil area.

10. The method of claim 9, wherein said weed growth controlled is annual or perennial weed growth.

11. The method of claim 9, wherein said soil area is an upland field.

* * * * *

UNITED STATES PATENT AND TRADEMARK OFFICE
CERTIFICATE OF CORRECTION

PATENT NO.    : 6,130,187
DATED         : October 10, 2000
INVENTOR(S)   : Masahiro Miyazaki, et al.

It is certified that error appears in the above-identified patent and that said Letters Patent is hereby corrected as shown below:

Title page,
Item [45] is listed incorrectly. The Terminal Disclaimer Information should be deleted. Item [45] should read as follows:

-- [45] Date of Patent:      Oct. 10, 2000 -- .

Signed and Sealed this

Fourth Day of September, 2001

*Attest:*

*Attesting Officer*

NICHOLAS P. GODICI
*Acting Director of the United States Patent and Trademark Office*